(12) United States Patent
Barany et al.

(10) Patent No.: US 7,198,894 B2
(45) Date of Patent: Apr. 3, 2007

(54) DETECTION OF NUCLEIC ACID DIFFERENCES USING COMBINED ENDONUCLEASE CLEAVAGE AND LIGATION REACTIONS

(75) Inventors: Francis Barany, New York, NY (US); Weiguo Cao, Central, SC (US); Jianmin Huang, Jackson Heights, NY (US); Jing Lu, Central, SC (US)

(73) Assignee: Cornell Research Foundation, Inc., Ithaca, NY (US)

( * ) Notice: Subject to any disclaimer, the term of this patent is extended or adjusted under 35 U.S.C. 154(b) by 512 days.

(21) Appl. No.: 09/998,481

(22) Filed: Nov. 30, 2001

(65) Prior Publication Data

US 2003/0148283 A1 Aug. 7, 2003

Related U.S. Application Data

(60) Provisional application No. 60/250,435, filed on Dec. 1, 2000.

(51) Int. Cl.
*C12Q 1/68* (2006.01)
*C12P 19/34* (2006.01)

(52) U.S. Cl. .................. 435/6; 435/91.1; 435/91.2; 435/91.52; 204/450

(58) Field of Classification Search ............. 435/6, 435/91.1, 91.2, 91.52; 204/450
See application file for complete search history.

(56) References Cited

U.S. PATENT DOCUMENTS

| | | | |
|---|---|---|---|
| 5,877,280 | A | 3/1999 | Wetmur |
| 6,080,544 | A | 6/2000 | Weghorst et al. |
| 6,110,684 | A | 8/2000 | Kemper et al. |
| 6,294,325 | B1 | 9/2001 | Wetmur |
| 2001/0039014 | A1 | 11/2001 | Bass et al. |

OTHER PUBLICATIONS

Day et al., "Nucleotide Analogs and New Buffers Improve a Generalized Method to Enrich for Low Abundance Mutations," *Nucleic Acids Research* 27(8):1819-1827 (1999).

Khanna et al., "Multiplex PCR/LDR for Detection of K-*ras* Mutations in Primary Colon Tumors," *Oncogene* 18(1):27-38 (1999).

Wilson et al., "Needle-in-a-Haystack Detection and Identification of Base Substitution Mutations in Human Tissues," *Mutation Research Genomics* 406:79-100 (1999).

Khanna et al., "Ligase Detection Reaction for Identification of Low Abundance Mutations," *Clinical Biochemistry* 32(4):287-290 (1999).

Lyamichev et al., "Polymorphism Identification and Quantitative Detection of Genomic DNA by Invasive Cleavage of Oligonucleotide Probes," *Nature Biotechnology* 17(3):292-296 (1999).

Cao et al., "Cloning and Thermostability of *Taq*I Endonuclease Isoschizomers from *Thermus* Species SM32 and *Thermus filiformis* Tok6A1," *Biochem. J.* 333(Pt. 2):425-431 (1998).

Morgan et al., "Characterization of the Specific DNA Nicking Activity of Restriction Endonuclease N.BstNBI," *Biol. Chem.* 381(11):1123-1125 (2000).

Yao et al., "Cleavage of Insertion/Deletion Mismatches, Flap and Pseudo-Y DNA Structures by Deoxyinosine 3'-Endonuclease from *Escherichia coli*," *Journal of Biological Chemistry* 271(48):30672-30676 (1996).

Morikawa et al., "Three-Dimensional Structural Views of Damaged-DNA Recognition: T4 Endonuclease V, *E. coli* Vsr Protein, and Human Nucleotide Excision Repair Factor XPA," *Mutation Research* 460(3-4):257-275 (2000).

Huang et al., "An Endonuclease/Ligase Based Mutation Scanning Method Especially Suited for Analysis of Neoplastic Tissue," *Oncogene* 21(12):1909-1921 (2002).

*Primary Examiner*—Gary Benzion
*Assistant Examiner*—Joyce Tung
(74) *Attorney, Agent, or Firm*—Nixon Peabody LLP

(57) ABSTRACT

The present invention is a method for detecting DNA sequence differences including single nucleotide mutations or polymorphisms, one or more nucleotide insertions, and one or more nucleotide deletions. Labeled heteroduplex PCR fragments containing base mismatches are prepared. Endonuclease cleaves the heteroduplex PCR fragments both at the position containing the variation (one or more mismatched bases) and to a lesser extent, at non-variant (perfectly matched) positions. Ligation of the cleavage products with a DNA ligase corrects non-variant cleavages and thus substantially reduces background. This is then followed by a detection step in which the reaction products are detected, and the position of the sequence variations are determined.

83 Claims, 30 Drawing Sheets

Mismatch scanning Assay.
(Endo V / DNA Ligase)

1. PCR amplify gene using primers with different fluorescent labels and *Taq* DNA polymerase.

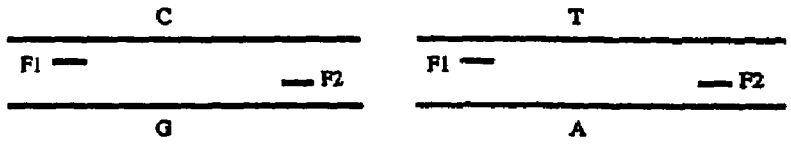

2. Denature and reanneal PCR products to form heteroduplexed DNA. (Homoduplexed products not shown).

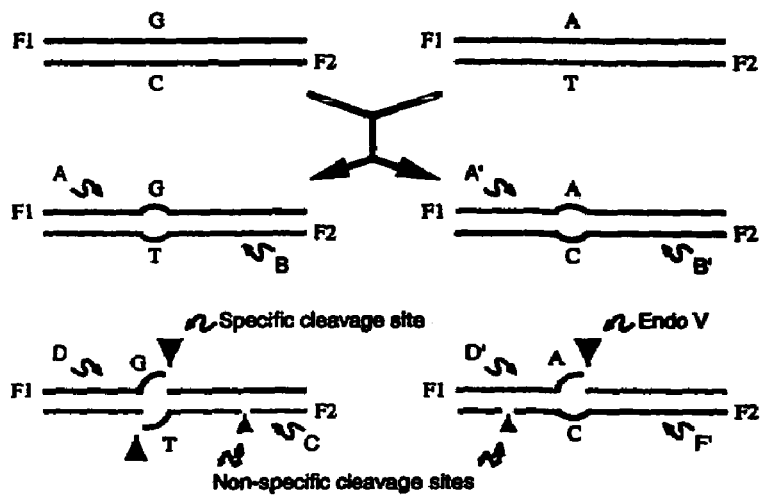

3. Preferentially nick DNA one base to the 3' side of mismatches using thermostable Endonuclease V.

4. Add thermostable ligase to re-seal background nicks at perfect match regions.

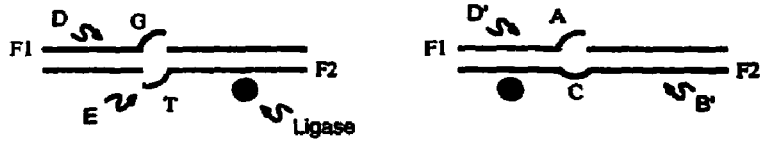

5. Separate fluorescent products on a DNA sequencer (using length standards) to approximate site of mismatch.

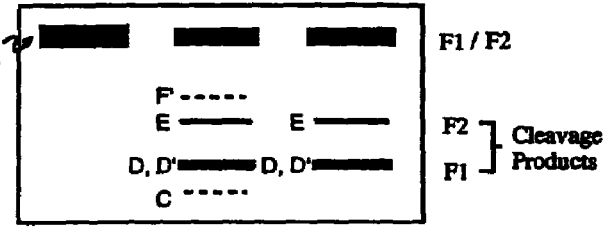

Figure 1

A
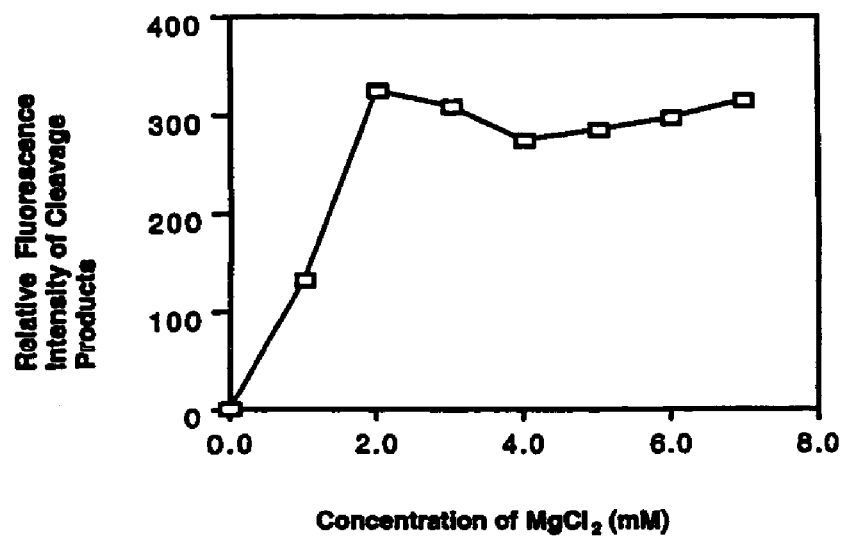
B
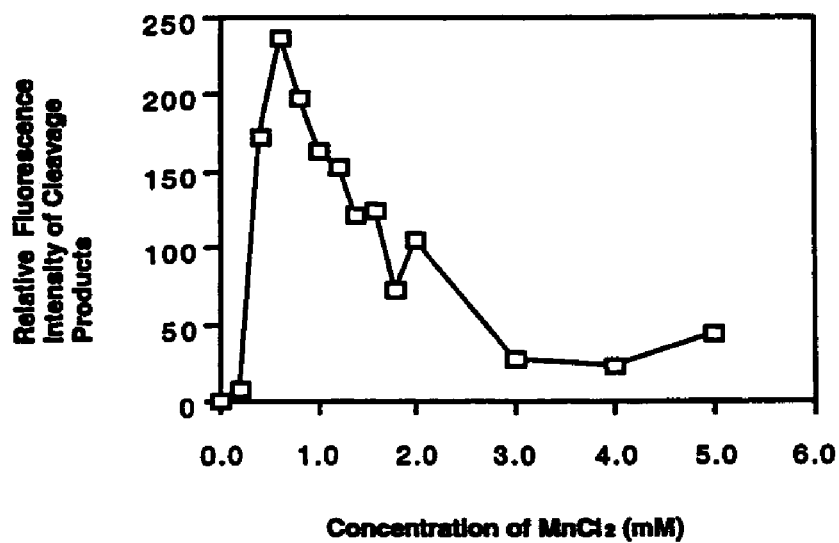
Figure 4

A
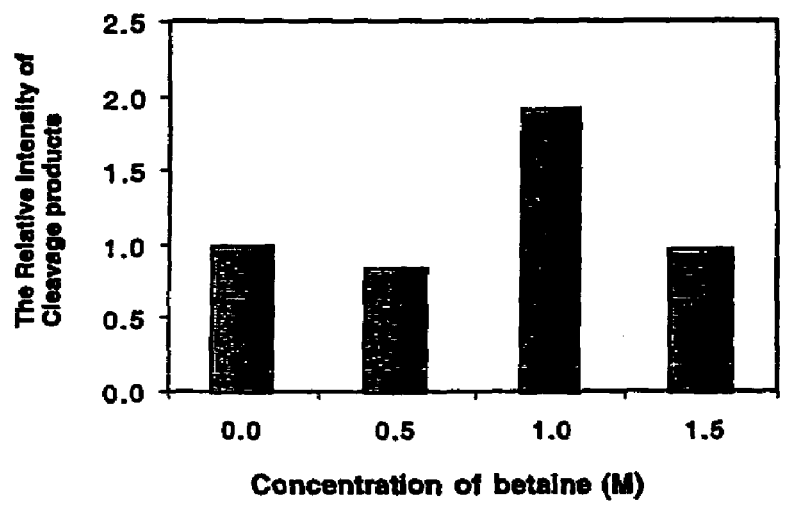
B
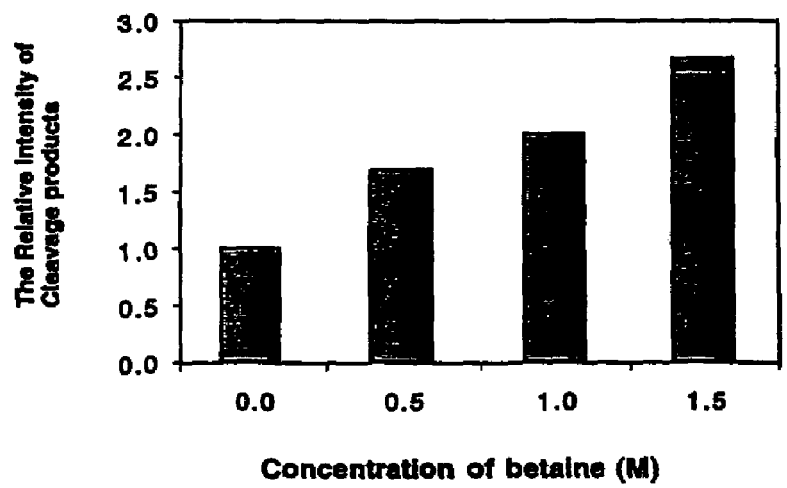
Figure 10

*k-ras* G12V (G->T)
A
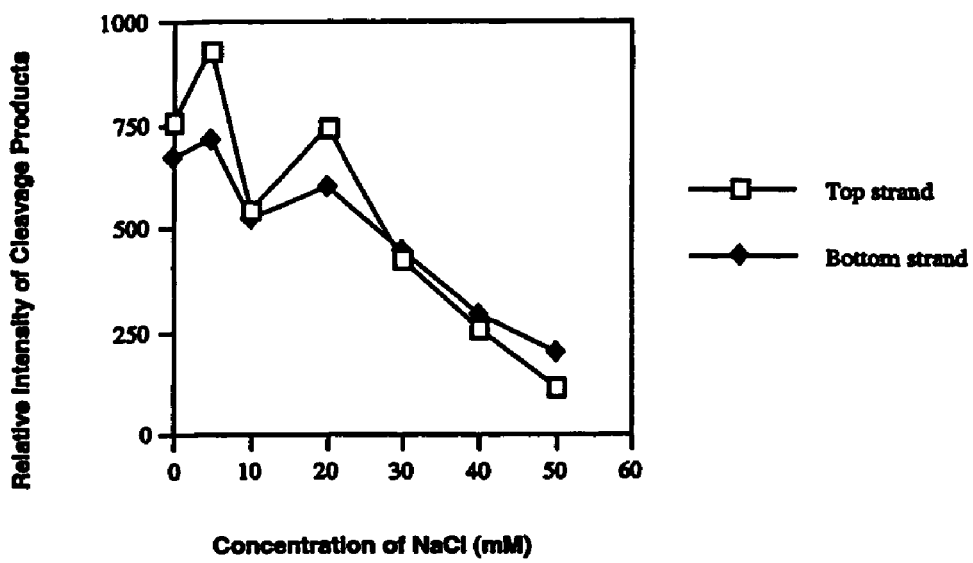
B
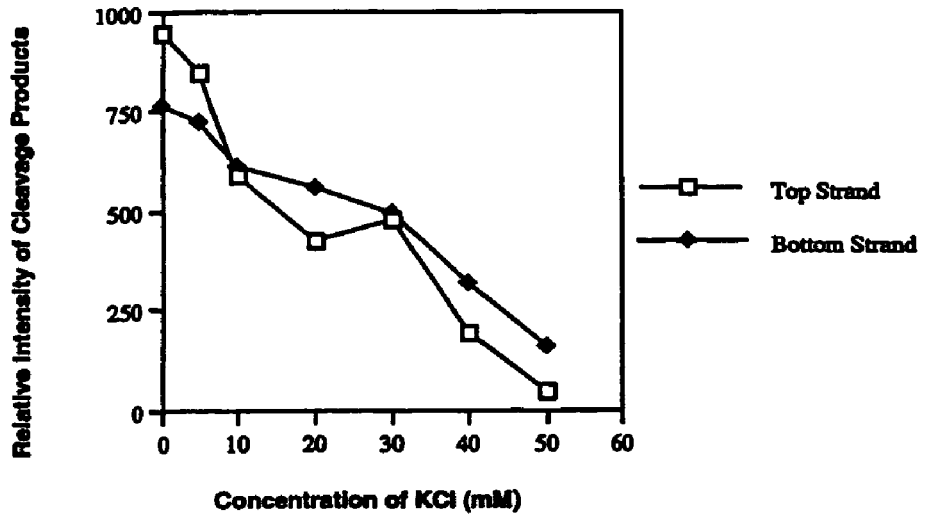
Figure 11

A
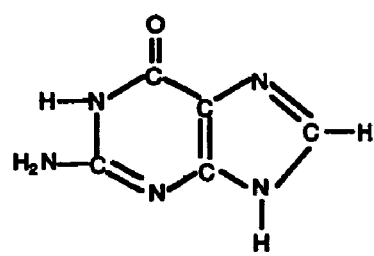
Guanine
B
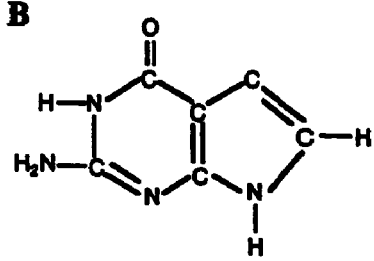
7-deaza-Guanine
C
dG  7deazaG
← PCR products
← Bottom strand cleavage products
← Top strand cleavage products
Figure 17

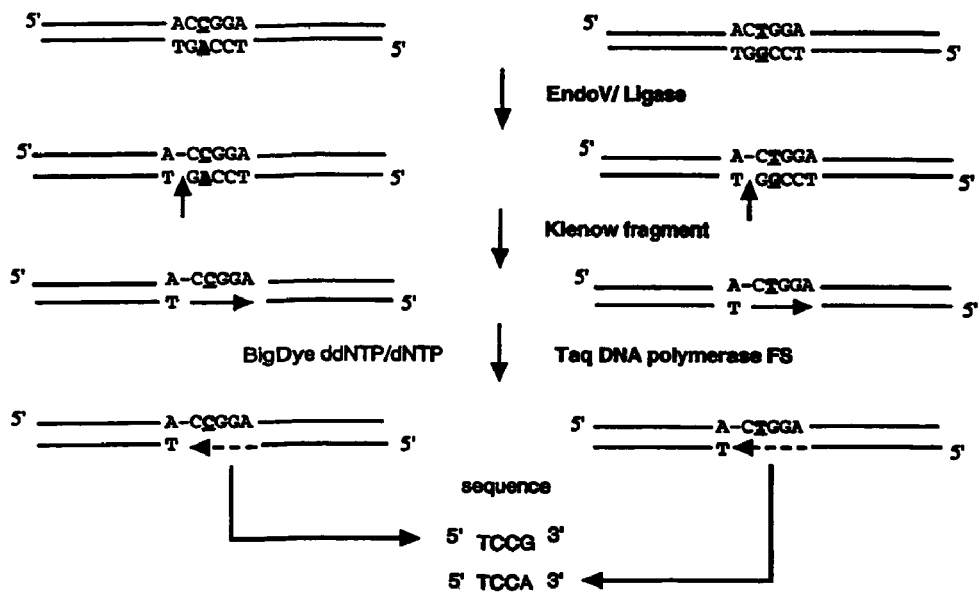
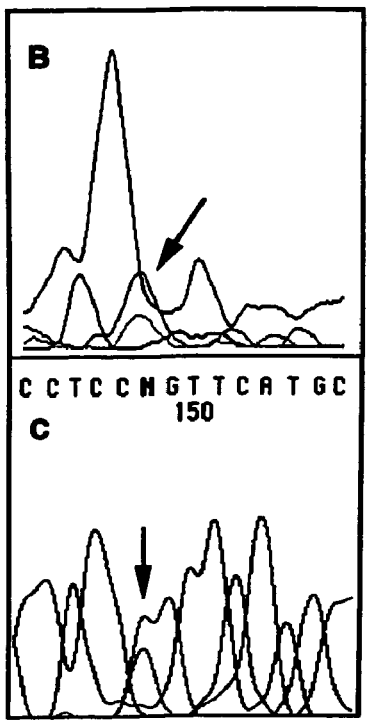
Figure 18

DETECTION OF NUCLEIC ACID DIFFERENCES USING COMBINED ENDONUCLEASE CLEAVAGE AND LIGATION REACTIONS

This application claims benefit of U.S. Provisional Patent Application Ser. No. 60/250,435, filed Dec. 1, 2000.

The present invention arose from research sponsored by the National Institutes of Health under Grant Nos. ROI-CA 65930 and ROI-CA 81467. The United States Government may have certain rights.

FIELD OF THE INVENTION

The present invention relates to detecting nucleic acid differences using combined endonuclease ("endo") cleavage and ligation reactions.

BACKGROUND OF THE INVENTION

Detection of DNA Sequence Variation

There is a great need in both basic and clinical research to identify DNA sequence variations with high efficiency and accuracy. The current techniques for detection of such variation can be divided into two groups: 1) detection of known mutations or polymorphisms and 2) detection of unknown mutations or polymorphisms (also referred to as mutation scanning). A variety of effective methods have been developed for detecting known mutations and polymorphisms and include techniques such as direct DNA sequencing, allele-specific oligonucleotide hybridization, allele-specific PCR, DNA arrays, and PCR/LDR. There are a variety of techniques for detecting unknown mutations, but their sensitivity and accuracy vary greatly.

Comparison of High-Throughput Techniques to Identify Unknown Mutations in Clinical Samples Identifying unknown mutations in clinical samples presents similar difficulties as screening for known mutations, as well as some novel complications. A mutation present in a tumor sample may represent as little as 15% of the DNA sequence for that gene due to stromal contamination. Therefore, screens for unknown mutations require high sensitivity in order to identify low abundance sequence. Since most cancer genes contain multiple exons which may be altered, even for commonly mutated genes (e.g. PTEN), most assay results of a single exon will be negative. However, by pooling samples together, the probability of finding a significant mutation in a given assay increases. In order to increase the capacity of a screen by pooling samples, the technique must have a high enough sensitivity to tolerate further mutation dilution which results from pooling. Further, for uncommon germline mutations, the ability to pool samples greatly improves the throughput of evaluating large numbers of samples in multiple exons.

Other significant complications associated with screening for unknown cancer mutations are the need to: (i) Identify either frameshift, nonsense, or missense mutations, and (ii) distinguish missense mutations from germline (i.e. silent) polymorphisms. The latter is of great significance, because it is estimated that polymorphisms exist approximately once every kb in the human genome. Wang, D. G., et al., *Science*, 280(5366):1077–82. (1998), Li, W. H., et al., *Genetics*, 129(2):513–23 (1991), Lai, E., et al., *Genomics*, 54(1): 31–38 (1998), Nickerson, D. A., et al., *Nat Genet*, 19(3): 233–40 (1998), Harding, R. M., et al., *Am. J. Hum. Genet.*, 60(4):772–89 (1997), Taillon-Miller, P. et al., *Genome Res.*, 8(7): 748–54 (1998), Halushka, M. K., et al., *Nat. Genet.*, 22(3): 239–47 (1999), and Cargill, M., et al., *Nat. Genet.*, 22(3):231–38 (1999). Separating out the apparently less interesting polymorphisms should significantly increase the efficiency in identifying informative mutations. Unfortunately, present methods of identifying additional low frequency mutations with clinical significance are restricted in their applications. Most methods to date lack either the accuracy to discriminate or the sensitivity to be an efficient technique. As a result, there is an urgent need for a scanning method with the potential to identify precise mutations and with the sensitivity to analyze tumors or germline DNA in pooled samples.

Direct Sequencing and Variation Detection Arrays

A variety of methods have been developed to scan for unknown mutations. Direct sequencing represents an ideal in that it can detect any mutation and its position, although high throughput is costly. Gyllensten, U. B. et al., *Proc. Natl. Acad. Sci. USA*, 85(20): 7652–56 (1988), Hultman, T., et al., *Nucleic Acids Res.*, 17(13):4937–46 (1989), Phear, G. A. et al., *Methods Mol. Biol.*, 31:247–56 (1994), Rao, V. B., *Anal. Biochem.*, 216(1):1–14 (1994), Kovach, J. S., et al., *J. Natl. Cancer Inst.*, 83(14):1004–9 (1991). This method has low sensitivity which prevents an accurate analysis of pooled samples, and, in regard to solid tumor samples, the technique is vulnerable to stromal contamination. In blinded studies, direct sequencing was unable to identify 20% of K-ras mutations in microdissected tumor samples. This number is consistent with other studies in which 24% of p53 mutations in lung tumor samples were not identified. Ahrendt, S., et al., *Proc. Natl. Acad. Sci. USA*, 96:7382–87 (1999). When automated sequence analysis was performed on these same lung tumor samples, this false negative value rose to 32%. Ahrendt, S., et al., *Proc. Natl. Acad. Sci. USA*, 96:7382–87 (1999). These results reflect the limits of sensitivity associated with direct sequencing and further demonstrate the difficulty of automating this approach. If a sample is known to have a mutation in a specific area, then repeated attempts of direct sequencing should be able to identify the mutation and its position. Therefore, direct sequencing may have utility as a second step to identify the exact base changed in a gene region previously identified as containing a mutation.

Variation detection arrays (VDA) use standard hybridization microarrays to scan large sequence blocks in given genes. Despite the high scanning capacity levels, this approach has some characteristics that limits its utility. VDA is unable to detect all mutations and has particular difficulty in detecting frameshift mutations, for example in the BRCA2 and p53 genes. Ahrendt, S., et al., *Proc. Natl. Acad. Sci. USA*, 96:7382–87 (1996), Hacia, J. G., et al., *Nature Genetics*, 14(4): 441–47 (1999). Primer extension arrays also fail to detect slippage of mononucleotide repeat sequences. Syvanen, A. C. et al., *Hum. Mutat.*, 3(3):172–79 (1994). High false positive rates of 11–21% have been observed using VDA. Halushka, M. K., et al., *Nat Genet.*, 22(3):239–47 (1999). One consequence of direct hybridization that may account for these inaccurate results involves the disruption of secondary structure. A perfect match PCR fragment may assume a secondary structure that is not present in variant fragments. Since a secondary structure is usually energetically unfavorable with respect to fragment/array hybridizations, the variant fragment may bind the perfect match complement on the array with higher binding affinity than the true perfect match fragment. Hacia, J., *Nature Genetics (Supplement)*, 21:42–47 (1999). Such illegitimate hybridizations would produce a false positive signal. Direct hybridization of mutation-containing PCR fragments to sequences on the array has the additional difficulty of simultaneously assaying sequence tracts with localized regions of both high G+C and A+T content. Hacia, J., *Nature Genetics (Supplement)*, 21:42–47 (1999). Certain mutations within these tracts can significantly decrease the Tm and thus lead to false negative signals.

Gel-Based Assays, Mismatch Cleavage Enzymes, and Protein Truncation Assays

Other methods that are widely used to detect unknown mutations resolve homoduplex and heteroduplex DNA based on their differing electrophoretic migration behavior. These methods include single-stranded conformational polymorphism (SSCP) (Suzuki, Y., et al., *Oncogene*, 5(7): 1037–43 (1990), Makino, R., et al., *PCR Methods Appl.*, 2(1):10–13 (1992), Hayashi, K., *PCR Methods Appl.*, 1(1): 34–38 (1991), Korn, S. et al., *J. Clin. Pathol.*, 46(7):621–23 (1993)), denaturing-gradient gel electrophoresis (DGGE) (Fahy, E., et al., *Nucleic Acids Research*, 25(15):3102–9 (1997), Fodde, R. et al., *Hum. Mutat.*, 3(2):83–94 (1994), Guldberg, P. et al., *Nucleic Acids Res.*, 22(5):880–81 (1994), Ridanpaa, M. et al., *Hum. Mol. Genet.*, 2(6):639–44 (1993), Ridanpaa, M., et al., *Mutat. Res.*, 334(3): 357–64 (1995) constant denaturing capillary electrophoresis (CDCE) (Chen, J. et al., *Environ. Health Perspect*, 3:227–29 (1994), Khrapko, K., et al., *Nucleic Acids Res.*, 22(3):364–69 (1994)), dideoxy fingerprinting (ddF) (Sarkar, G., et al., *Genomics*, 13:441–43 (1992)), and restriction endonuclease fingerprinting (REF) (Liu, Q. et al., *Biotechniques*, 18(3): 470–77 (1995)). A similar approach, denaturing high-performance liquid chromatography (DHPLC), also resolves homoduplex from heteroduplex DNA but is based on separation by ion-pair reverse-phase liquid chromatography on alkylated nonporous (styrene divinylbenzene) particles. Underhill, P. A., et al., *Genome Res.*, 7(10):996–1005 (1997). Although these techniques contain some very desirable characteristics, none of them are complete with respect to both previously-discussed throughput and sensitivity. The techniques which can identify the position of the polymorphism (ddF and REF), are not applicable for evaluating low level mutations in pooled samples. The rest of these techniques tend to be rapid and can detect low level mutations, but they cannot distinguish missense from silent polymorphisms. In addition, since these methods do not locate the position of the mutation, they are less compatible with follow up techniques such as direct sequencing.

A sophisticated approach for detecting frame-shifts or termination codons in the APC gene uses a coupled transcription translation assay referred to as the protein truncation test. Powell, S. M., et al., *Nature*, 359(6392):235–37 (1992), Powell, S. M., et al., *N. Engl. J. Med.*, 329:1982–87 (1993), Redston, M. S., et al., *Gastroenterology*, 108(2): 383–92 (1995), Petersen, G. M., et al., *Hum. Genet.*, 91(4): 307–11 (1993), Su, L. K., et al., *Cancer Res.*, 53(12): 2728–31 (1993). This is currently the most robust approach for finding mutations which generate truncated proteins in large genes; however, it does not detect missense mutations or polymorphisms. Polymorphisms may also be identified by cleavage of mismatches in DNA hybrids, such as DNA-RNA heteroduplexes via RNase A mismatch cleavage (Winter, E., *Proc. Natl. Acad. Sci. USA*, 82(22):7575–79 (1985), Perucho, M., et al., *Cancer Cells*, 7:137–41 (1989), Myers, R. M., et al., *Science*, 230(4731):1242–46 (1985)), as well as in DNA-DNA homoduplexes via chemical mismatch cleavage (CCM) (Cotton, R. G. H., et al., *Proc. Natl. Acad. Sci. USA*, 85:4397–401 (1988), Hansen, L. L., et al., "Sensitive and Fast Mutation Detection by Solid-Phase Chemical Cleavage", in *PCR Primer: A Laboratory Manual*, C. W. Diefenbach and G. S. Dveksler, Editors., Cold Spring Harbor Laboratory Press: New York. p. 275–86 (1995), Haris, I. I., et al., *PCR Methods Appl.*, 3(5):268–71 (1994)), T4 Endonuclease VII or MutY cleavage (Youil, R., et al., *Proc. Natl. Acad. Sci. USA*, 92(1):87–91 (1995), Xu, J. F., et al., *Carcinogenesis*, 17(2):321–26 (1996), Giunta, C., et al., *Diagn. Mol. Pathol.*, 5(4):265–70 (1996)), or via Cleavase. Recently, a plant endonuclease, CEL I, with similar activity to T4 endonuclease VII has been described. Oleykowski, C. A., et al., *Nucleic Acids Res.*, 26(20):4597–602 (1998). CEL I has similar activity to nuclease S1 and works at neutral pH. Its cleavage efficiency and background varies according to the mismatch and specific template examined, and further evaluation of other templates (e.g. in GC-rich regions) is still required. The most accepted mismatch cleavage approaches identify the approximate position of the polymorphism by using T4 Endonuclease VII or MutY to cleave a heteroduplex of normal and polymorphic substrate at a mismatch. Youil, R., et al., *Proc. Natl. Acad. Sci. USA*, 92(1):87–91 (1995), Xu, J. F., et al., *Carcinogenesis*, 17(2):321–26 (1996) Giunta, C., et al., *Diagn. Mol. Pathol.*, 5(4):265–70 (1996). These enzymatic cleavage approaches identify the approximate position of most polymorphisms; however, these enzymes often nick matched DNA causing a high background noise. This high background tends to limit their usefulness with respect to solid tumor studies.

The present invention is directed to overcoming the above deficiencies in the art.

SUMMARY OF THE INVENTION

One aspect of the present invention is directed to a method for identifying a mutant nucleic acid sequence differing by one or more single-base changes, insertions, or deletions, from a normal target nucleotide sequences. This method involves blending: (1) a sample potentially containing the normal target nucleotide sequence as well as the mutant nucleic acid sequence; (2) providing two labeled oligonucleotide primers suitable for hybridization on complementary strands of the target nucleotide sequence and the mutant nucleic acid sequence; and (3) providing a polymerase to form a polymerase chain reaction mixture. The polymerase chain reaction mixture is subjected to one or more polymerase chain reaction cycles comprising a hybridization treatment where oligonucleotide primers can hybridize to the target nucleotide sequence and/or the mutant nucleic acid sequence, an extension treatment where the hybridized oligonucleotide primer is extended to form an extension product complementary to the target nucleotide sequence and/or the mutant nucleic acid sequence to which the oligonucleotide primer is hybridized, and a denaturation treatment where hybridized nucleic acid sequences are separated. After the polymerase is inactivated, the polymerase chain reaction extension products are denatured and the polymerase chain reaction extension products are annealed to form heteroduplexed products potentially containing the normal target nucleotide sequence and the mutant nucleic acid sequence. An endonuclease, which preferentially nicks or cleaves heteroduplexed DNA at a location one base away from mismatched base pairs, is then blended with the heteroduplexed products to form an endonuclease cleavage reaction mixture. The endonuclease cleavage reaction mixture is blended so that the endonuclease preferentially nicks or cleaves heteroduplexed products at a location one base away from mismatched base pairs. A ligase and the potentially nicked or cleaved heteroduplexed products are blended to form a ligase resealing reaction mixture. The ligase resealing reaction mixture is incubated to seal the nicked heteroduplexed products at perfectly matched base pairs but with substantially no resealing of nicked heteroduplexed products at locations adjacent to mismatched base pairs. The products resulting from incubating the ligase resealing reaction mixture are separated by size or electrophoretic mobility, and the presence of the normal target nucleotide sequence and the mutant nucleic acid sequence target nucleotide are detected in the sample by distinguishing the separated products resulting from incubating the ligase resealing reaction mixture.

Another aspect of the present invention relates to a method for identifying a mutant nucleic sequence differing by one or more single-base changes, insertions, or deletions from a normal target nucleic acid sequence. In this method, a sample potentially containing the mutant nucleic acid sequence but not necessarily the normal target nucleic acid sequence, a standard containing the normal target nucleic acid sequence, two labeled oligonucleotide primers suitable for hybridization on complementary strands of the mutant nucleic acid sequence, and a polymerase are blended to form a first polymerase chain reaction mixture. The first polymerase chain reaction mixture is subjected to one or more polymerase chain reaction cycles which includes a hybridization treatment, where the labeled oligonucleotide primers can hybridize to the mutant nucleic acid sequence, an extension treatment, where the hybridized oligonucleotide primer is extended to form an extension product complementary to the mutant nucleic acid sequence to which the oligonucleotide primer is hybridized, and a denaturation treatment, where hybridized nucleic acid sequences are separated. The polymerase is then inactivated. The normal target nucleic acid sequence, the labeled oligonucleotide primers, and the polymerase are blended to form a second polymerase chain reaction mixture. The second polymerase chain reaction mixture is subjected to one or more polymerase chain reaction cycles comprising a hybridization treatment, where the labeled oligonucleotide primers can hybridize to the normal target nucleic acid sequence, an extension treatment, where the hybridized oligonucleotide primer is extended to form an extension product complementary to the normal target nucleic acid sequence to which the oligonucleotide primer is hybridized, and a denaturation treatment, where hybridized nucleic acid sequences are separated. The polymerase is then deactivated. The first and second polymerase chain reaction extension products are denatured and then annealed to form heteroduplexed products potentially containing the normal target nucleic acid sequence and the mutant nucleic acid sequence. An endonuclease which preferentially nicks or cleaves heteroduplexed DNA at a location one base away from mismatched base pairs is blended with the heteroduplexed products to form an endonuclease cleavage reaction mixture. The endonuclease cleavage reaction mixture is incubated so that the endonuclease preferentially nicks or cleaves heteroduplexed products at a location one base away from mismatched base pairs. A ligase and the potentially nicked or cleaved heteroduplexed products are blended to form a ligase resealing reaction mixture which is incubated to seal the nicked heteroduplexed products at perfectly matched base pairs but with substantially no resealing of nicked heteroduplexed products at locations adjacent to mismatched base pairs. The products resulting from incubating the ligase resealing reaction mixture by size or electrophoretic mobility are separated, and the presence of the normal target nucleic acid sequence and the mutant nucleic acid sequence target nucleotide in the sample is detected by distinguishing the separated products resulting from incubating the ligase resealing reaction mixture.

Another aspect of the present invention relates to a thermostable endonuclease which generates ends that are suitable for ligation when nicking perfectly matched DNA and preferentially nicks or cleaves heteroduplexed DNA as follows: (1) at a location where base pairs are mismatched or one base beyond the mismatch and (2) at A/A, G/G, T/T, A/G, A/C, G/A, G/T, T/G, T/C, C/A, or C/T mismatched base pairs at a location where the base pairs are mismatched or one base beyond the mismatch. In each of alternatives (1) and (2), ends are generated which are suitable for ligation when nicking perfectly matched DNA. A thermostable endonuclease in accordance with the present invention preferentially nicks or cleaves at least one heteroduplex formed for any single base mutation or polymorphism, except those having gRcg, rcRc, cgYc, or gYgy sequences, where the position of the mismatch is underlined and shown in upper case, and generates ends which are suitable for ligation when nicking perfectly matched DNA. Alternatively, the thermostable endonuclease, which preferentially nicks or cleaves heteroduplexed DNA, contains one, two, and three base insertions or deletions, at a location where the base pairs are mismatched or one base beyond the unpaired bases, and generates ends which are suitable for ligation when nicking DNA at perfect matched DNA.

Another aspect of the present invention is a mutant endonuclease V ("endo V") from *Thermotoga maritima* containing either: (1) a Y80A residue change; (2) a Y80F residue change; (3) either a Y80L, Y80I, Y80V or Y80M residue change; (4) an R88A residue change; (5) an R88L, R88I, R88V, or R88M residue change; (6) an R88K residue change; (7) an R88N or R88Q residue change; (8) an R88D or R88E residue change; (9) an R88T or R88S residue change; (10) a E89A residue change; (11) a E89L, E89I, E89V, or E89M residue change; (12) a E89D residue change; (13) a E89N or E89Q residue change; (14) a E89R or E89K residue change; (15) a E89T or E89S residue change; (16) a H116A residue change; (17) a H116L, H116I, H116V, or H116M residue change; (18) a H116K or H116R residue change; (19) a H116N or H116Q residue change; (20) a H116T or H116S residue change; (21) a K139A residue change; (22) a K139L, K139I, K139V, or K139M residue change; (23) a K139R residue change; (24) a K139N or K139Q residue change; (25) a K139D or K139E residue change; (26) a K139T or K139S residue change; (27) a D43A residue change; (28) a D43E residue change; (29) a D105A residue change; (30) a D105E residue change; (31) an F46A residue change; (32) an F46Y residue change; (33) an F46L, F46I, F46V, or F46M residue change; (34) an R118A residue change; (35) an R118L, R118I, R118V, or R118M residue change; (36) an R118K residue change; (37) an R118N or R118Q residue change; (38) an R118D or R118E residue change; (39) an R118T or R118S residue change; (40) a F180A residue change; (41) a F180Y residue change; (42) a F180L, F180I, F180V, or F180M residue change; (43) a G83A residue change; (44) a G83L, G83I, G83V, or G83M residue change; (45) a G83K or G83R residue change; (46) a G83N or G83Q residue change; (47) a G83D or G83E residue change; (48) a G83T or G83S residue change; (49) an I179A residue change; (50) an I179K or I179R residue change; (51) an I179N or I179Q residue change; (52) an I179D or I179E residue change; (53)

an I179T or I179S residue change; (54) a D110A residue change; or (55) an H125A residue change.

A further aspect of the present invention is directed to a mutant endonuclease V which preferentially nicks or cleaves at least one heteroduplexed DNA, containing mismatched bases, better than a wild-type endonuclease V.

A further aspect of the present invention is directed to a method for identifying a mutant nucleic acid sequence differing by one or more single-base changes, insertions, or deletions, from a normal target nucleic acid sequence. In this method, a sample potentially containing the normal target nucleic acid sequence as well as the mutant nucleic acid sequence, two labeled oligonucleotide primers suitable for hybridization on complementary strands of the target nucleic acid sequence and the mutant nucleic acid sequence, and a polymerase are blended to form a polymerase chain reaction mixture. The polymerase chain reaction mixture is subjected to one or more polymerase chain reaction cycles comprising a hybridization treatment, where aoligonucleotide primers can hybridize to the target nucleic acid sequence and/or the mutant nucleic acid sequence, an extension treatment, where the hybridized oligonucleotide primer is extended to form an extension product complementary to the target nucleic acid sequence and/or the mutant nucleic acid sequence to which the oligonucleotide primer is hybridized, and a denaturation treatment, where hybridized nucleic acid sequences are separated. After the polymerase is inactivated, the polymerase chain reaction extension products are denatured and annealed to form heteroduplexed products potentially containing the normal target nucleic acid sequence and the mutant nucleic acid sequence. An endonuclease which preferentially nicks or cleaves heteroduplexed DNA at a location one base away from mismatched base pairs and the heteroduplexed products are blended to form an endonuclease cleavage reaction mixture which is incubated so that the endonuclease preferentially nicks or cleaves heteroduplexed products at a location one base away from mismatched base pairs. A ligase and the potentially nicked or cleaved heteroduplexed products are blended to form a ligase resealing reaction mixture which is incubated to seal the nicked heteroduplexed products at perfectly matched base pairs but with substantially no resealing of nicked heteroduplexed products at locations adjacent to mismatched base pairs. A polymerase with 3'-5' exonuclease activity and the potentially nicked or cleaved heteroduplexed products are blended to form a polymerase exonucleolytic degradation reaction mixture which is incubated under conditions effective for the 3'-5' exonucleolytic activity to remove several bases 3' to the nick. After the polymerase with 3'-5' exonuclease activity is inactivated, a polymerase without 3'-5' activity and the incubated polymerase degradation reaction mixture, labeled dideoxyterminator triphosphate nucleotides, and deoxyribonucleotide triphsophates are blended to form a polymerase mini-sequencing reaction mixture which is incubated under conditions effective for the polymerase without 3'-5' activity to extend the 3' end of the nicked or cleaved heteroduplexed products to form mini-sequencing reaction products. The mini-sequencing products are separated by size or electrophoretic mobility, and the presence of normal target nucleic acid sequence and the mutant nucleic acid sequence are detected by distinguishing the separated mini-sequencing products resulting from incubating the polymerase mini-sequencing reaction mixture.

The present invention has proven effective in identifying unknown frameshift, nonsense, and missense mutations as demonstrated in tests screening for various mutations in six genes associated with the development of inherited or sporadic cancers. Furthermore, paired germline DNA can be evaluated side-by-side with tumor DNA, allowing this invention to even distinguish missense mutations from nearby or adjacent inherited polymorphisms. The assay also has broad applicability with respect to types of sequence variations that can be detected, and can identify 98% of the typical mutations or polymorphisms found in the human genome. In addition, it is capable of scanning for mutations in a region as long as 1.7 kb or greater. The present invention can detect mutations in a high background of normal sequence. The present invention can detect a mutation or polymorphism in a 1:20 dilution with wild-type DNA and can even detect mutations/polymorphisms in cases as low as 1:50 dilution with wild-type DNA. This high sensitivity makes the present invention amenable to pooled samples and, therefore, significantly increasing its throughput capabilities.

BRIEF DESCRIPTION OF THE DRAWING

FIG. 1 is a schematic diagram, illustrating the procedure for mutation scanning with the combination of *Thermotoga maritima* ("Tma") endo V and Tsp.AK16D DNA ligase.

FIG. 2A is a 12.5% SDS-PAGE, while FIG. 2B shows gel filtration of the purified endo V. Molecular weight markers were from Sigma Chemical (St. Louis, Mo.). Ve is the elution volume and $V_0$ is the void volume.

FIG. 3A is an assay design where the top strand (SEQ. ID. No. 1) is Fam labeled and the bottom strand (SEQ. ID. No. 2) is Tet labeled to allow fluorescence detection on a GeneScan gel (Perkin Elmer). The positions of nucleotide changes at both strands are underlined. The length of the substrates and predominant products are marked. The cleavage sites are marked by arrows. The cleavage reactions were performed as described in M&M in the presence of 5 mM $MgCl_2$ with different E:S (enzyme:substrate) ratios. In FIG. 3B, E:S=1:10, and the relationship between substrate and product is shown by the arrow. In FIG. 3C, E:S=10:1 and the first lanes of FIGS. 3B and C are substrate negative controls. FIG. 3D shows the location of cleavage sites. The length markers were synthetic oligonucleotides identical to the top strand or the bottom strand as shown in FIG. 3A.

FIGS. 4A–B are plots of relative fluorescence intensity of cleavage products v. concentration of $MgCl_2$ which demonstrate the base-mismatch cleavage activity of Tma endonuclease V at varying concentrations of $Mg^{2+}$ or $Mn^{2+}$.

FIG. 6A shows the cleavage of double-stranded oligonucleotides containing a basic site (AP site) or deoxyuridine. 1: untreated substrate control; 2: AP substrates incubated at 95° C. for 1 min in 50 mM NaOH as an AP site control; 3 and 10: oligonucleotide length markers; 4 and 7: 1 nM Tma endo V (E:S=:10); 5 and 8: 10 nM Tma endo V (E:S=1:1); 6 and 9: 100 nM Tma endo V (E:S=10:1. FIG. 6B is a gel mobility shift assay of AP and uracil sites. Reactions were performed with 20 nM double-stranded oligonucleotide DNA substrates, 5 mM $CaCl_2$ and indicated amount of Tma endo V as specified below. Other buffer components are unchanged, 1: substrate control; 2: 10 nM Tma endo V; 4 and 6: 100 nM Tma endo V; 7: inosine substrate control; 8: 100 nM Tma endo V with 20 nM inosine subtrate as positive control. FIG. 6C shows the cleavage of single-stranded oligonucleotides. Cleavage reactions were performed in the presence of 5 mM $MgCl_2$ or 1 mM $MnCl_2$ with 10 nM Tma endo V (E:S=1:1). NS: non-specific sequence. FIG. 6D shows the cleavage of plasmid substrate. Cleavage reactions were performed with 10 nM pFB76 plasmid in the presence of 5 mM $MgCl_2$ or 1 mM $MnCl_2$. M: 1 kb DNA ladder; lane 1: intact plasmid pFB76; lane 2: cleavage reaction performed with 100 nM Tma endo V but without adding metal cofactor; lanes 3 and 6: E:S=1:10; Lanes 4 and 7: E:S=1:1; Lanes 5 and 8: E:S=10:1. FIGS. 6E–G show the binding of single-stranded inosine substrate. The binding reaction mixture contained 100 nM single-stranded inosine substrate, 2 mM EDTA (FIG. 6E) or 5 mM $MgCl_2$ (FIG. 6F) or 5 mM $CaCl_2$ (FIG. 6G), 20% glycerol, 10 mM HEPES (pH 7.4), 1 mM DTT, and 10 nM-1 μm Tma Endo V. The reaction mixtures were incubated at 65° C. for 30 min before loading to a 6% native polyacrylamide gel. Lane 1: E:S=0, lane 2: E:S=1:10; lane 3: E:S=1.2; lane 4: E:S=1:1; lane 5:E:S=5:1; lane 6: E:S=10:1.

FIGS. 10A–B are plots of relative intensity of cleavage products v. concentration of betaine which show the effect of betaine concentration on Tma endonuclease V base-mismatch cleavage activity.

FIGS. 11A–B are plots of relative intensity of cleavage products v. concentration of KCR. FIG. 11A shows that the cleavage of PCR fragments with Tma endo V favors low or no NaCl concentrations. FIG. 11B shows the inhibitory effects of KCl on the cleavage reaction with Tma endo V.

FIG. 16A is a schematic diagram of the p53 1.7 kb amplicon showing primer labeling and predicted size of cleavage product. FIG. 16B demonstrates the ability of the present invention to detect point mutations in the p53 gene, and subsequent incubation with DNA ligase allows for sealing of non-specific cleavage products, while still retaining the correct, specific cleavage products.

FIGS. 17A–B show the chemical formulae for guanine and 7-deaza-guanine, respectively. FIG. 17C demonstrates the base-mismatch cleavage activity of Tma endo V when the PCR fragments contain 7-deaza-dG.

FIG. 18A is a schematic diagram of the DNA micro sequencing process. FIGS. 18B–C are sequence traces of a micro sequencing reactions.

In FIG. 21B, the cleavage reactions were performed with E:S (enzyme: substrate) ratio of 10:1 (S=10 nM) in the presence of 5 mM $MgCl_2$. In FIG. 21C, the cleavage reactions were performed with E:S (enzyme: substrate) ratio of 1:1 (S=10 nM) in the presence of 5 mM $MnCl_2$.

In FIG. 22A, gel mobility shift assays were performed with an inosine-containing double-stranded substrate (I/A) using 2 mM EDTA instead of $MgCl_2$. In FIG. 22B, gel mobility shift assays with an inosine-containing double-stranded substrate (I/A) in the presence of $CaCl_2$. For FIG. 22C, gel mobility shift assays were carried out with an inosine-containing double-stranded substrate (I/A) in the presence of $MgCl_2$.

In FIG. 23A, gel mobility shift assays were conducted with a nicked inosine-containing double-stranded product (I/A) in the presence of $CaCl_2$. In FIG. 23B, gel mobility shift assays were performed with a nicked inosine-containing double-stranded product (I/A) in the presence of $MgCl_2$.

FIG. 25A shows cleavage by Tma endo V mutants. The cleavage reactions were performed as described with E:S (enzyme: substrate) ratio of 1:1 (S=10 nM) in the presence of 5 mM $MgCl_2$. FIG. 25B shows the gel mobility shift of Tma endo V mutants without metal cofactor. FIG. 25C shows the gel mobility shift of Tma endo V mutants with 5 mM CaCl$_2$. FIG. 25D shows a gel mobility shift of Tma endo V mutants with 5 mM MgCl$_2$.

FIG. 26A shows the cleavage of A/U substrate. FIG. 26B shows the cleavage of G/U substrate. FIG. 26C shows the cleavage of T/U substrate. FIG. 26D shows the cleavage of AP site substrate (A/AP).

DETAILED DESCRIPTION OF THE INVENTION

Detecting DNA Sequence Differences

Figure 2:
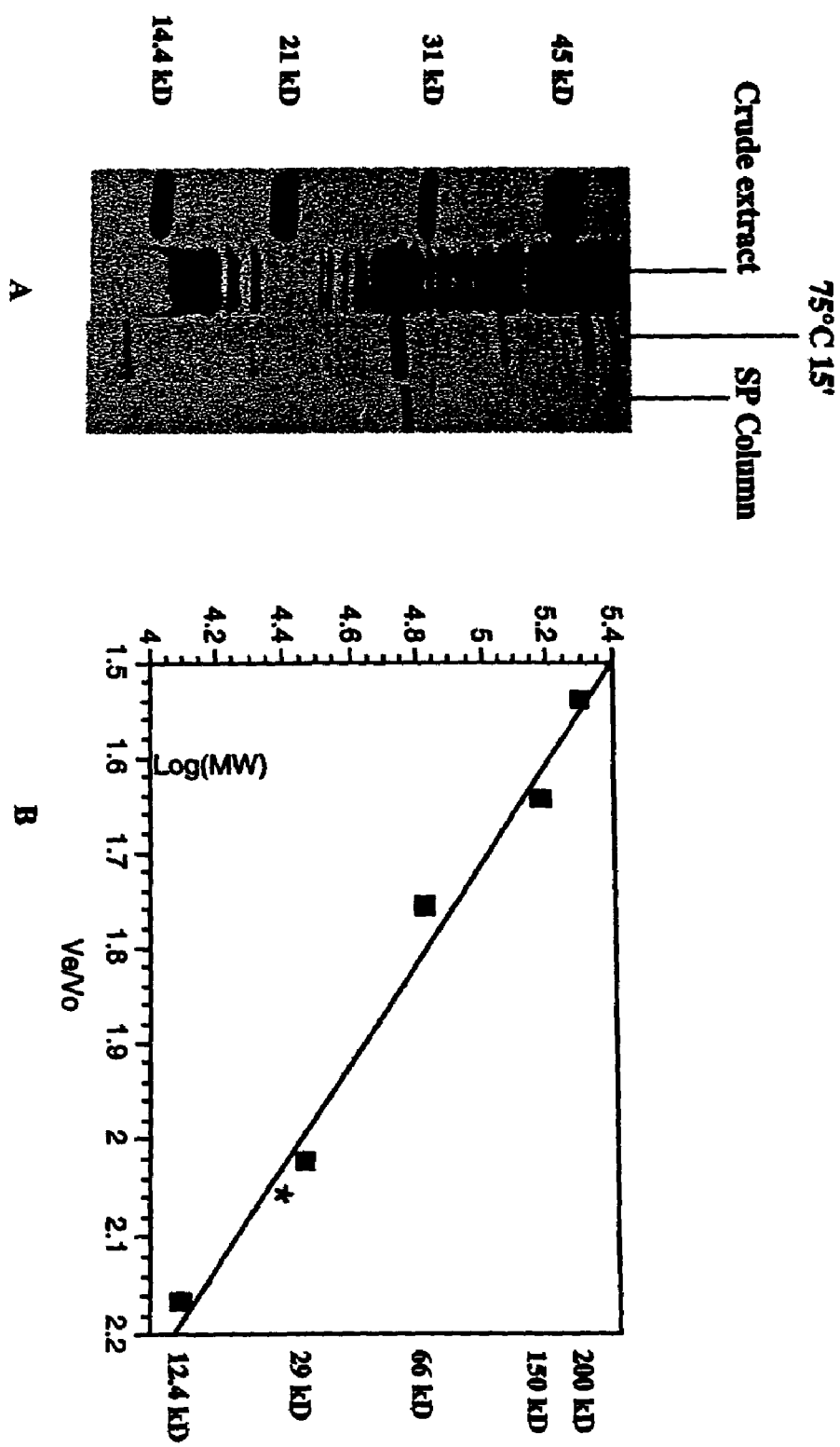
FIGS. 2A–B show the purification of Tma endonuclease V.

One aspect of the present invention is directed to a method for identifying a mutant nucleic acid sequence differing by one or more single-base changes, insertions, or deletions, from a normal target nucleotide sequence. This method involves blending: (1) a sample potentially containing the normal target nucleotide sequence as well as the mutant nucleic acid sequence; (2) providing two labeled oligonucleotide primers suitable for hybridization on complementary strands of the target nucleotide sequence and the mutant nucleic acid sequence; and (3) providing a polymerase to form a polymerase chain reaction mixture. The polymerase chain reaction mixture is subjected to one or more polymerase chain reaction cycles comprising a hybridization treatment where oligonucleotide primers can hybridize to the target nucleotide sequence and/or the mutant nucleic acid sequence, an extension treatment where the hybridized oligonucleotide primer is extended to form an extension product complementary to the target nucleotide sequence and/or the mutant nucleic acid sequence to which the oligonucleotide primer is hybridized, and a denaturation treatment where hybridized nucleic acid sequences are separated. After the polymerase is inactivated, the polymerase chain reaction extension products are denatured and the polymerase chain reaction extension products are annealed to form heteroduplexed products potentially containing the normal target nucleotide sequence and the mutant nucleic acid sequence. An endonuclease, which preferentially nicks or cleaves heteroduplexed DNA at a location one base away from mismatched base pairs, is then blended with the heteroduplexed products to form an endonuclease cleavage reaction mixture. The endonuclease cleavage reaction mixture is blended so that the endonuclease preferentially nicks or cleaves heteroduplexed products at a location one base away from mismatched base pairs. A ligase and the potentially nicked or cleaved heteroduplexed products are blended to form a ligase resealing reaction mixture. The ligase resealing reaction mixture is incubated to seal the nicked heteroduplexed products at perfectly matched base pairs but with substantially no resealing of nicked heteroduplexed products at locations adjacent to mismatched base pairs. The products resulting from incubating the ligase resealing reaction mixture are separated by size or electrophoretic mobility, and the presence of the normal target nucleotide sequence and the mutant nucleic acid sequence are detected in the sample by distinguishing the separated products resulting from said incubating the ligase resealing reaction mixture.

The first step of the invention is the preparation of heteroduplex nucleic acid fragments. In the preferred embodiment, genomic DNA containing both wild-type and the sequence variation(s) (e.g. single nucleotide mutations or polymorphisms, one or more nucleotide insertions, and one or more nucleotide deletions) is PCR amplified with labeled oligonucleotide primers. Fluorescent, infrared, radioactive, or other labels may be used in the primers. In the preferred embodiment, Taq DNA polymerase or other PCR enzymes are inactivated, for example, by digestion with proteinase K. The mixture of mutation or polymorphism containing and wild-type PCR fragments are denatured and then reannealed to form heteroduplex PCR fragments with nucleotide mismatches. In the preferred embodiment, denaturation is achieved by heating the fragments above their Tm value (generally greater than 94° C.), and reannealing is achieved by cooling first to 50–85° C., more preferably, 65° C. for 5–30 minutes, more preferably 15 minutes, and then to room temperature for 5–30 minutes, more preferably 15 minutes, to form heteroduplex PCR fragments. Alternative means of denaturing/renaturing may be used. If wild-type genomic DNA is not known to be present in the original reaction, then concurrently in a separate reaction, wild type genomic DNA is PCR amplified using the exact same primers as above. Equal molar amounts of mutation containing PCR fragments and wild type PCR fragments are mixed, heated, and then cooled to form heteroduplex PCR fragments with nucleotide mismatches.

The second step utilizes Tma endonuclease V for cleavage of the heteroduplex DNA containing base mismatches. This reaction is preferably performed in an optimized reaction buffer at high temperature (50–65° C.) for 30 minutes to 1 hour. Optimal buffer conditions include a neutral pH, low or no salt, and the presence of Mg$^{2+}$. Addition of organic solvents or other compounds, such as DMSO and betaine, may be used to facilitate cleavage by Tma Endo V. Use of alternative conditions or metal co-factors (such as Mn$^{2+}$) may also facilitate cleavage. Tma endonuclease V activity can be sufficient even under sub-optimal conditions. The cleavage site was determined to be one nucleotide beyond the 3' position of the nucleotide mismatch.

For the next step, a supplemental buffer is added to bring the contents and concentration of the buffer to a level optimized for a thermostable DNA ligase. In the preferred embodiment, a *Thermus* species ("Tsp.") AK16D DNA ligase is used. This ligation reaction is performed at 45 to 85° C., preferably 65° C., for 2 to 60 minutes, preferably 20 minutes and utilizes the high specificity of Tsp. AK16D DNA ligase to reseal complementary nicks, while leaving cleaved mismatches unaltered. This greatly reduces background and, therefore, dramatically increases the sensitivity of the assay.

In the fourth step, the cleaved fragments are separated, for example, by electrophoresis on a denaturing polyacrylamide gel or by capillary electrophoresis. Since the PCR primers of step one are labeled, fragments can be detected with the corresponding detection equipment. In the preferred embodiment, primers are fluorescently labeled and detected using automated DNA sequencing or fluorescent fragment analysis instrumentation. The lengths of products are determined by comparison of the mobility of cleavage products to a fluorescent labeled molecular size standard. This allows for an approximate determination of the position of a mutation.

A second embodiment of this invention can incorporate a micro-sequencing method to determine which nucleotide is mutated. In preparing the PCR fragments, unlabeled primers are used in place of labeled primers, so that the heteroduplex PCR fragments are not fluorescent. After cleavage by Tma endo V and ligation by Tsp. AK16D ligase, *E. coli*. DNA polymerase I Klenow fragment is used to excise several nucleotides from the 3' end of the nick generated by Tma endo V. Next, *Thermus aquaticus* ("Taq") DNA polymerase FS extends the shortened fragment using a mixture of fluorescent labeled dideoxynucleotides and unlabeled deoxynucleotides as substrates. This results in a short sequencing ladder from which the position and base of the variant nucleotide can be determined due to the mixed signal of the normal and mutated nucleotide at the variant position.

FIG. 1 is a schematic drawing illustrating the process of the present invention. In this drawing, the sample potentially contains a normal target nucleic acid sequence as well as a mutant nucleic acid sequence differing by one or more single-base changes, insertions, or deletions from the normal target nucleotide sequence.

In the first step of this procedure, target DNA molecules in a sample, potentially containing wild type and mutant nucleic acid sequences are amplified by a polymerase chain reaction process. This involves denaturation of double stranded target DNA molecules to separate complementary strands from one another. Primers with fluorescent labels F1 and F2 are then caused to hybridize to part of the target DNA molecule. In the presence of DNA polymerase and dNTPs, the primers are extended to form extension products which are complementary to a strand of the target DNA molecule. After extension is completed, the hybridized nucleic acid strands are separated from one another by a denaturation step. This cycle of hybridization, primer extension, and denaturation is repeated until sufficient amplification has taken place. Once this has occurred, PCR is terminated by inactivating the polymerase and denaturing the hybridized nucleic acid strands.

In the second step of FIG. 1, the extension products formed by PCR are annealed to one another to form heteroduplexed products. To the extent that these extension products were formed in the first step of FIG. 1 by extension of a primer hybridized to a mutant nucleic acid sequence in the sample, the extension product will include a mismatched base. As shown in the second step of FIG. 1, the mismatch in the extension product can be an A, C, T, or G nucleotide. When, in the second step of FIG. 1, an extension product produced by target nucleic acid sequence forms a heteroduplex with an extension product produced by a mutant nucleic acid sequence, there will be a mismatch in the heteroduplex. This lack of complementation between such extension products is shown by a "bubble" where the extension products are displaced from one another. Although not shown in FIG. 1, homoduplexes containing extension products produced solely from mutant nucleic acid (which would usually be rare) or produced solely from the target nucleic acid sequence would be fully complementary, so no bubble would form. The present invention is directed to detecting the presence of such mutant nucleic acid sequences in the sample by analyzing for mismatches in the heteroduplexes.

The third step of FIG. 1 involves subjecting the heteroduplexed products to an endonuclease which preferentially nicks or cleaves the component strands of the heteroduplexed products at a location one base away from a mismatched base. In the case of heteroduplexed products which are formed from an extension product produced by target nucleic acid sequence annealed to an extension product produced by a mutant nucleic acid sequence as shown in the third step of FIG. 1, the component nucleic acid strands are nicked or cleaved one base away from the bubble. As also shown in the third step of FIG. 1, the endonuclease cleaves these strands at non-specific cleavage sites where there is no mismatch. As to the nicking which takes place at specific cleavage sites where there is a mismatch, the endonuclease is generally very effective at making nicks in strands where the mismatch base is an A or G, is less effective at making nicks where the mismatch base is T, and is generally ineffective at nicking where the mismatch base is C. This is shown in the third step of FIG. 1 where nicking has occurred at the mismatched A, G, and T bases but not at the mismatched C base.

After endonuclease treatment is completed, the resulting potentially nicked or cleaved heteroduplexed products are treated with a ligase. As shown in the fourth step of FIG. 1, the ligase reseals the nicked heteroduplexed products at perfectly mismatched bases. However, there is no resealing of the nicked heteroduplexed products at locations adjacent to where there is a mismatched base.

The products of the ligase resealing step are then separated from one another by size or electrophoretic mobility, usually by gel electrophoresis. The results of gel electrophoresis before treatment with either endonuclease or ligase, after treatment with endonuclease and treatment with ligase, and after treatment with both endonuclease and ligase is shown in FIG. 1. As a result, cleavage products produced due to the presence of mutant nucleic acid sequence in the sample are detected.

In carrying out the process of the present invention, the sample can contain target nucleotide sequence which is either genomic DNA, DNA isolated from tumor samples, a double stranded cDNA copy of mRNA, or a PCR amplified DNA fragment. In the sample being analyzed according to the process of the present invention, the molar ratio of the mutant nucleic acid sequence to the normal target nucleotide sequence is in a range of 1:20 to 20:1.

The process of the present invention is capable of distinguishing an inherited or sporadic mutation or polymorphism from a polymorphism in the normal target sequence. This distinction can be made in a tumor suppressor gene, oncogene, or DNA replication or repair gene. Such genes include Bcl2, Mdm2, Cdc25A, Cyclin D1, Cyclin E1, Cdk4, survivin, HSP27, HSP70, p53, $p21^{Cip}$, $p16^{Ink4a}$, $p19^{ARF}$, $p15^{INK4b}$, $p27^{Kip}$, Bax, growth factors, EGFR, Her2-neu, ErbB-3, ErbB-4, c-Met, c-Sea, Ron, c-Ret, NGFR, TrkB, TrkC, IGF1R, CSF1R, CSF2, c-Kit, AXL, Flt-1 (VEGFR-1), Flk-1 (VEGFR-2), PDGFRα, PDGFRβ, FGFR-1, FGFR-2, FGFR-3, FGFR-4, other protein tyrosine kinase receptors, P-catenin, Wnt(s), Akt, Tcf4, c-Myc, n-Myc, Wisp-1, Wisp-3, K-ras, H-ras, N-ras, c-Jun, c-Fos, PI3K, c-Src, Shc, Raf1, TGFβ, and MEK, E-Cadherin, APC, TβRII, Smad2, Smad4, Smad 7, PTEN, VHL, BRCA1, BRCA2, ATM, hMSH2, hMLH1, hPMS1, hPMS2, or hMSH3.

Since residual active Taq DNA polymerase can extend Endo V cleaved DNA, PCR reactions can be incubated with proteinase K at 45 to 75° C. for 5 to 60 min., preferably 70° C. for 10 min. Subsequently, proteinase K is activated by incubating at 90 to 95° C. for 10 to 60 minutes, preferably 70° C. for 10 minutes. After amplification and proteinase K digestion, PCR fragments can be separated by agarose gel electrophoresis and visualized via ethidium bromide staining.

Most biological sources of target DNA will contain both variant (mutation or polymorphism) and wild type DNA. In these cases, it is not necessary to add wild-type PCR fragments exogenously to the heteroduplex hybridization step. For example, if the substrate is genomic DNA containing a heterozygous germline mutation, only 50% of the PCR fragments will contain a mutation, while the other half will be of wild-type sequence. Therefore, it is not necessary to add wild-type PCR fragments. Likewise, for solid tumor samples, there is typically a significant amount of stromal (i.e. wild-type) DNA within these samples. For sources of substrate in which a significant amount of endogenous wild-type DNA does not exist, an approximately equal amount of wild-type PCR fragments needs to be added. The optimal final ratio of mutant-to-wild type PCR fragments should be 1:1, although the technique is compatible with other ratios of mutant-to-wild type PCR fragments.

The labeled oligonucleotide primers are labeled, preferably at their 5' ends. Useful labels include chromophores, fluorescent moieties, enzymes, antigens, heavy metals, magnetic probes, infrared dyes, phosphorescent groups, radioactive materials, chemiluminescent moieties, and electrochemical detecting moieties.

The polymerase is either a native or recombinant thermostable polymerase from *Thermus aquaticus, Thermus thermophilus, Pyrococcus furiosus*, or *Thermotoga maritima*.

The polymerase chain reaction process is fully described in H. Erlich, et. al., "Recent Advances in the Polymerase Chain Reaction," *Science* 252: 1643–50 (1991); M. Innis, et. al., *PCR Protocols: A Guide to Methods and Applications*, Academic Press: New York (1990); and R. Saiki, et. al., "Primer-directed Enzymatic Amplification of DNA with a Thermostable DNA Polymerase," *Science* 239: 487–91 (1988), which are hereby incorporated by reference. The polymerase chain reaction is initiated by adding either the polymerase or metal co-factors at temperatures of 65–94° C. to the polymerase chain reaction mixture. The step of denaturing the polymerase chain reaction extension products is carried out in the presence of proteinase K, preferably by heating to 80 to 105° C., preferably 94° C. The step of annealing the polymerase chain reaction extension products is carried out by cooling first to 50 to 85° C., preferably 65° C., for 5 to 30 minutes, preferably, 10 minutes and then to room temperature for 5 to 30 minutes, preferably, 15 minutes.

For heteroduplex DNA formation, the mixture containing fluorescently labeled mutant and wild-type PCR fragments is denatured by heating at 93 to 100° C. for 15 sec. to 5 min., preferably, 94° C. for 1 min, thus rendering the DNA single-stranded. This is followed by a re-annealing step at 45 to 85° C. for 2 to 60 min., preferably 65° C. for 10 min, and, subsequently, incubating at room temperature for 5 to 30 min., preferably 15 min. After this process, theoretically 50% of the re-annealed products are heteroduplex DNA containing a base-mismatch. An alternative reanneal step would be a slow cool from 95 to 25° C., decreasing the temperature by less than 1° C. per minute, preferably, from 94° C. to 65° C. for 30–60 minutes. Alternative means of denaturing/renaturation of the DNA (such as treatment with a base followed by neutralization) may also be used. Typically, the polymerase chain reaction extension products have a length in the range of 50 bp to 1,700 bp.

The endonuclease is preferably an Endonuclease V from *Thermotoga maritima, Aquifex aeolicus, Pyrococcusfuriosus, Pyrococcus horikoshii, Pyrococcus abyssi, Pyrobaculum aerophilum, Archaeoglobus fulgidus, Aeropyrum pernix, Clostridium acetobutylicum*, or *Bacillus subtilis*. The endonuclease desirably nicks or cleaves heteroduplexed products at a location on the 3' side one base away from mismatched base pairs. The endonuclease preferentially cleaves mismatches within the heteroduplexed products selected from the group consisting of A/A, G|G, T/T, A/G, A/C, G/A, G/T, T/G, T/C, C/A, and C/T. Alternatively, the endonuclease preferentially nicks or cleaves at least one of the heteroduplexed products formed for any single base mutation or polymorphism, except those having a sequence selected from the group consisting of gRcg, rcRc, cgYc, and gYgy, where the position of the mismatch is underlined and shown in upper case. The endonuclease preferentially nicks or cleaves one, two, and three base insertions or deletions within the heteroduplexed products.

The endonuclease cleavage reaction is preferably carried out in presence of $MgCl_2$ at a concentration of 2–7 mM or $MnCl_2$ at a concentration of 0.4–1.2 mM. $MgCl_2$ should be added where the endonuclease to heteroduplexed product weight ratio in the endonuclease cleavage reaction mixture is in the range of 10:1 to 100:1; substantially no NaCl or KCl is present. Where the endonuclease to heteroduplexed product weight ratio in the endonuclease cleavage reaction mixture is in the range of 1:1 to 1:10, $MnCl_2$ should be added; in this case, a 25 to 75 mM, preferably 50 mM, concentration of NaCl or KCl is present. Endonuclease cleavage can also be carried out in the presence of DMSO in a volume percent range of 2.5% to 10% and betaine in a concentration of 0.5M to 1.5M. Preferably, the endonuclease treatment is carried out at 65° C. for 1 hour.

In the second step of the present invention, heteroduplexed PCR fragments are cleaved by Tma endonuclease V. Tma endonuclease V contains unique properties that make it ideal for this process. Most significant is its ability to preferentially cleave one base beyond the 3' side of a mismatch and the fact that spurious nicks at complementary regions are suitable substrates for religation with DNA ligase. While there are other mismatch repair enzymes which are more efficient in recognizing base mismatches, they generally do not cleave at the mismatch, nor do they leave ends suitable for religation. In conjunction with an appropriate ligase, these properties of Tma endo V allow for the reduction of background noise due to spurious nicking, while maintaining cleaved sites associated with mismatch sequence.

The third step of this invention seals nonspecific nicks in the heteroduplex PCR fragments with a thermostable ligase, such as *Thermus* species AK16D, *Thermus aquaticus, Thermus thermophilus, Pyrococcus furiosus*, or *Thermotoga maritima*. The thermostable ligase may be derived from *Thermus aquaticus*. M. Takahashi, et al., "Thermophillic DNA Ligase," *J. Biol. Chem.* 259:10041–47 (1984), which is hereby incorporated by reference. Alternatively, it can be prepared recombinantly. Procedures for such isolation as well as the recombinant production of *Thermus aquaticus* ligase as well as *Thermus themophilus* ligase) are disclosed in WO 90/17239 to Barany, et. al., and F. Barany, et al., "Cloning, Overexpression and Nucleotide Sequence of a Thermostable DNA-Ligase Encoding Gene," *Gene* 109: 1–11 (1991), which are hereby incorporated by reference. These references contain complete sequence information for this ligase as well as the encoding DNA. Ligase resealing is preferably carried out in the presence of 50 mM KCl to inhibit further endonucleolytic cleavage. Preferably, Tsp AK16D ligase is used. Ligase resealing is carried out at a pH value between 7.2 and 7.8 when measured at 25° C. Ideally, the cleavage of Tma endonuclease V should be inhibited in this step. The optimal reaction buffer for Tsp AK16D ligase is 20 mM Tris-HCl (pH 8.5), 5 mM $MgCl_2$, 25–75 mM (preferably, 50 mM) KCl, 10 mM dithiothreitol, 1 mM $NAD^+$, and 20 mg/ml BSA. See Tong, J., et al., *Nucleic Acid Research* 27:788–94 (1999). As demonstrated in the Examples, infra, Tma. endo V is ahnost completely inhibited in the presence of 50 mM NaCl or 50 mM KCl.

In order to obtain near optimal buffer conditions for the Tsp AK16D ligase reaction., a supplemental buffer is added to the Tma endo V reaction. In a preferred embodiment, the 10× supplemental buffer consists of 200 mM Tris-HCl (pH 8.5), 12.5 mM $MgCl_2$, 500 mM KCl, 100 mM DTT, and 200 g/ml BSA. Typically, 15 μL of the reaction mixture from a Tma endonuclease V cleavage reaction, 2 μL of 10× supplemental buffer, 1 μL of 20 mM $NAD^+$, and 2 μL of 10–100 nM Tsp AK16D ligase (stock enzyme solution) are combined. The mixture can then be incubated at 65° C. for 20 min and terminated by adding an equal volume of GeneScan stop solution (50 mM EDTA, 1% blue dextran and 80% formamide).

The next step involves detection of the reaction products which can be carried out using polyacrylamide gel electrophoresis or capillary gel electrophoresis.

In the preferred embodiment, the reaction mixture is denatured at 94° C. for only 1 minute (to avoid DNA fragmentation which can increase background signal), and then cooled on ice. 2–3 μL of the mixture can then be loaded onto a 6% denaturing polyacrylamide gel and electrophoresed for 1 hour. An ABI 377 sequencer (Perkin Elmer) at 1000 volt, 60 mA current, 200 W power, and a gel temperature of 45° C. can be used to separate and detect DNA products, although alternative capillary or gel electrophoresis approaches can be used. Fluorescent groups, 6-FAM (bottom fragment) and TET (top fragment), resolve blue and green, respectively, in the ABI DNA 377 sequencer. The color of the cleavage band indicates whether the cleavage product originated from the top or bottom strand. TAMRA labeled GeneScan Molecular size standard 500 are loaded on the same gel. This allows for the molecular weight of cleavage products to be estimated by comparing the relative mobility of a cleavage product to the size standard. Preferably, the GeneScan analysis software versions 2.1 or 3.0a (PE-Biosystems) is used, although any state of the art gel-analysis software can instead be employed. This analysis allows for the approximate site of the mutation to be determined.

Another aspect of the present invention relates to a method for identifying a mutant nucleic sequence differing by one or more single-base changes, insertions, or deletions from a normal target nucleic acid sequence. In this method, a sample potentially containing the mutant nucleic acid sequence but not necessarily the normal target nucleic acid sequence, a standard containing the normal target nucleic acid sequence, two labeled oligonucleotide primers suitable for hybridization on complementary strands of the mutant nucleic acid sequence, and a polymerase are blended to form a first polymerase chain reaction mixture. The first polymerase chain reaction mixture is subjected to one or more polymerase chain reaction cycles which includes a hybridization treatment, where the labeled oligonucleotide primers can hybridize to the mutant nucleic acid sequence, an extension treatment, where the hybridized oligonucleotide primer is extended to form an extension product complementary to the mutant nucleic acid sequence to which the oligonucleotide primer is hybridized, and a denaturation treatment, where hybridized nucleic acid sequences are separated. The polymerase is then inactivated. The normal target nucleic acid sequence, the labeled oligonucleotide primers, and the polymerase are blended to form a second polymerase chain reaction mixture. The second polymerase chain reaction mixture is subjected to one or more polymerase chain reaction cycles comprising a hybridization treatment, where the labeled oligonucleotide primers can hybridize to the normal target nucleic acid sequence, an extension treatment, where the hybridized oligonucleotide primer is extended to form an extension product complementary to the normal target nucleic acid sequence to which the oligonucleotide primer is hybridized, and a denaturation treatment, where hybridized nucleic acid sequences are separated. The polymerase is then deactivated. The first and second polymerase chain reaction extension products are denatured and then annealed to form heteroduplexed products potentially containing the normal target nucleic acid sequence and the mutant nucleic acid sequence. An endonuclease which preferentially nicks or cleaves heteroduplexed DNA at a location one base away from mismatched base pairs is blended with the heteroduplexed products to form an endonuclease cleavage reaction mixture. The endonuclease cleavage reaction mixture is incubated so that the endonuclease preferentially nicks or cleaves heteroduplexed products at a location one base away from mismatched base pairs. A ligase and the potentially nicked or cleaved heteroduplexed products are blended to form a ligase resealing reaction mixture which is incubated to seal the nicked heteroduplexed products at perfectly matched base pairs but with substantially no resealing of nicked heteroduplexed products at locations adjacent to mismatched base pairs. The products resulting from incubating the ligase resealing reaction mixture by size or electrophoretic mobility are separated, and the presence of the normal target nucleic acid sequence and the mutant nucleic acid sequence target nucleotide in the sample is detected by distinguishing the separated products resulting from incubating the ligase resealing reaction mixture.

DNA Micro-sequencing for Identification of the Position and Composition of a Mutation or Insertion/Deletion A further aspect of the present invention is directed to a method for identifying a mutant nucleic acid sequence differing by one or more single-base changes, insertions, or deletions from a normal target nucleic acid sequence. In this method, a sample potentially containing the normal target nucleic acid sequence as well as the mutant nucleic acid sequence, two labeled oligonucleotide primers suitable for hybridization on complementary strands of the target nucleic acid sequence and the mutant nucleic acid sequence, and a polymerase are blended to form a polymerase chain reaction mixture. The polymerase chain reaction mixture is subjected to one or more polymerase chain reaction cycles comprising a hybridization treatment, where oligonucleotide primers can hybridize to the target nucleic acid sequence and/or the mutant nucleic acid sequence, an extension treatment, where the hybridized oligonucleotide primer is extended to form an extension product complementary to the target nucleic acid sequence and/or the mutant nucleic acid sequence to which the oligonucleotide primer is hybridized, and a denaturation treatment, where hybridized nucleic acid sequences are separated. After the polymerase is inactivated, the polymerase chain reaction extension products are denatured and annealed to form heteroduplexed products potentially containing the normal target nucleic acid sequence and the mutant nucleic acid sequence. An endonuclease which preferentially nicks or cleaves heteroduplexed DNA at a location one base away from mismatched base pairs and the heteroduplexed products are blended to form an endonuclease cleavage reaction mixture which is incubated so that the endonuclease preferentially nicks or cleaves heteroduplexed products at a location one base away from mismatched base pairs. A ligase and the potentially nicked or cleaved heteroduplexed products are blended to form a ligase resealing reaction mixture which is incubated to seal the nicked heteroduplexed products at perfectly matched base pairs but with substantially no resealing of nicked heteroduplexed products at locations adjacent to mismatched base pairs. A polymerase with 3'-5' exonuclease activity and the potentially nicked or cleaved heteroduplexed products are blended to form a polymerase exonucleolytic degradation reaction mixture which is incubated under conditions effective for the 3'-5' exonucleolytic activity to remove several bases 3' to the nick. After the polymerase with 3'-5' exonuclease activity is inactivated, a polymerase without 3'-5' activity and the incubated polymerase degradation reaction mixture, labeled dideoxyterminator triphosphate nucleotides, and deoxyribonucleotide triphosphates are blended to form a polymerase mini-sequencing reaction mixture which is incubated under conditions effective for the polymerase without 3'-5' activity to extend the 3' end of the nicked or cleaved heteroduplexed products to form mini-sequencing reaction products. The mini-sequencing products are separated by size or electrophoretic mobility, and the presence of normal target nucleic acid sequence and the mutant nucleic acid sequence are detected by distinguishing the separated mini-sequencing products resulting from incubating the polymerase mini-sequencing reaction mixture.

Treatment with a polymerase with 3'-5' exonuclease activity is carried out at a temperature of 20 to 40° C. for 10 to 60 minutes, preferably 37° C. and 30 minutes. Suitable polymerases with 3'-5' exonuclease activity are E. coli DNA polymerase I Klenow fragment, T4 DNA polymerase, and T7 DNA polymerase.

The polymerase without 3'-5' activity is utilized in the polymerase mini-sequencing reaction mixture at a temperature of 20 to 85° C. for 10 to 60 seconds, preferably 60° C. and 30 seconds. Suitable polymerases without 3'-5' activity are AmpliTaq DNA polymerase FS (Perkin Elmer, Foster City, Calif.), Thermo-sequenase, (Amersham, Piscataway, N.J. 08855), and DyNASeq, (M. J. Research, 590 Lincoln Street, Waltham, Mass. 02451). Examples of a mesophilic polymerases without 3' to 5' exonuclease activity are Sequenase (USB, Cleveland, Ohio 44128), and other polymerases with site-specific mutations to knock out the 3' to 5' exonuclease activity.

In this embodiment of the present invention, an optional DNA sequencing step (i.e. micro DNA sequencing) can be included to accurately determine the composition and position of an altered nucleotide. In this variation of the present invention, the procedure is similar to that described above, except that unlabeled PCR primers are used in the PCR reaction. This results in PCR fragments which are unlabeled and, therefore, compatible with fluorescent dideoxysequencing. The presence or absence of fluorescent label is not an issue with radiolabeled dideoxy sequencing, and, therefore, the variation of the technique is purely one of compatibility with the detection method of the sequencing assay and not necessarily required for DNA sequencing in general.

The micro-sequencing strategy contains two additional steps. In the first added step, after the Tma endo V cleavage and ligation with Tsp. AK16D ligase, the 3' exonuclease activity of DNA polymerase I Klenow fragment is utilized to excise a few bases 3'→5' from the mismatch nick generated by Tma Endo V. E. coli DNA polymerase I Klenow fragment possesses approximately a hundred-fold lower 3' exonuclease activity than T4 or T7 DNA polymerase (Sambrook, J. et al., *Molecular Cloning-A Laboratory Manual,* 2nd Ed., Cold Spring Harbor Laboratory Press, Cold Spring Harbor, N.Y. (1989), which is hereby incorporated by reference). This allows for a more controlled removal of only a few bases. AmpliTaq DNA polymerase FS (Perkin Elmer) is then used to fill the resulting gap with a substrate mixture of BigDye™ ddNTP/dNTP. This results in a very short fluorescent sequence ladder which can be analyzed to determine the exact position and nature of the variation.

Mutants of *Thermatoga maritima* Endo V

Another aspect of the present invention relates to a thermostable endonuclease which generates ends that are suitable for ligation when nicking perfectly matched DNA and preferentially nicks or cleaves heteroduplexed DNA as follows: (1) at a location where base pairs are mismatched or one base beyond the mismatch and (2) at A/A, G/G, T/T, A/G, A/C, G/A, G/T, T/G, T/C, C/A, or C/T mismatched base pairs at a location where the base pairs are mismatched or one base beyond the mismatch. In each of alternatives (1) and (2), ends are generated which are suitable for ligation when nicking perfectly matched DNA. A thermostable endonuclease in accordance with the present invention preferentially nicks or cleaves at least one heteroduplex formed for any single base mutation or polymorphism, except those having gRcg, rcRc, cgYc, or gYgy sequences, where the position of the mismatch is underlined and shown in upper case, and generates ends which are suitable for ligation when nicking perfectly matched DNA. Alternatively, the thermostable endonuclease, which preferentially nicks or cleaves heteroduplexed DNA, contains one, two, and three base insertions or deletions, at a location where the base pairs are mismatched or one base beyond the unpaired bases, and generates ends which are suitable for ligation when nicking DNA at perfect matched DNA.

Another aspect of the present invention is a mutant endonuclease V from *Thermotoga maritima* containing either: (1) a Y80A residue change; (2) a Y80F residue change; (3) either a Y80L, Y80I, Y80V or Y80M residue change; (4) an R88A residue change; (5) an R88L, R88I, R88V, or R88M residue change; (6) an R88K residue change; (7) an R88N or R88Q residue change; (8) an R88D or R88E residue change; (9) an R88T or R88S residue change; (10) a E89A residue change; (11) a E89L, E89I, E89V, or E89M residue change; (12) a E89D residue change; (13) a E89N or E89Q residue change; (14) a E89R or E89K residue change; (15) a E89T or E89S residue change; (16) a H116A residue change; (17) a H116L, H116I, H116V, or H116M residue change; (18) a H116K or H116R residue change; (19) a H116N or H116Q residue change; (20) a H116T or H116S residue change; (21) a K139A residue change; (22) a K139L, K139I, K139V, or K139M residue change; (23) a K139R residue change; (24) a K139N or K139Q residue change; (25) a K139D or K139E residue change; (26) a K139T or K139S residue change; (27) a D43A residue change; (28) a D43E residue change; (29) a D105A residue change; (30) a D105E residue change; (31) an F46A residue change; (32) an F46Y residue change; (33) an F46L, F46I, F46V, or F46M residue change; (34) an R118A residue change; (35) an R118L, R118I, R118V, or R118M residue change; (36) an R118K residue change; (37) an R118N or R118Q residue change; (38) an R118D or R118E residue change; (39) an R118T or R118S residue change; (40) a F180A residue change; (41) a F180Y residue change; (42) a F180L, F180I, F180V, or F180M residue change; (43) a G83A residue change; (44) a G83L, G83I, G83V, or G83M residue change; (45) a G83K or G83R residue change; (46) a G83N or G83Q residue change; (47) a G83D or G83E residue change; (48) a G83T or G83S residue change; (49) an I179A residue change; (50) an I179K or I179R residue change; (51) an I179N or I179Q residue change; (52) an I179D or I179E residue change; (53) an I179T or I179S residue change; (54) a D110A residue change; or (55) an H125A residue change.

A further aspect of the present invention is directed to a mutant endonuclease V (and its above-described uses) which preferentially nicks or cleaves at least one heteroduplexed DNA, containing mismatched bases, better than a wild-type endonuclease V. Preferably, one of the mismatched bases in at least one of the heteroduplexed DNA is "A" or "G".

EXAMPLES

Example 1

Reagents, Media, and Strains

All routine chemical reagents were purchased from Sigma Chemicals (St. Louis, Mo.) or Fisher Scientific (Fair Lawn, N.J.). deoxynucleotide, BSA, and ATP were purchased from Boehringer-Mannheim (Indianapolis, Ind.). Deoxyoligonucleotides were ordered from Integrated DNA Technologies Inc. (Coralville, Iowa). HiTrap SP columns were purchased from Amersham-Pharmacia Biotech (Piscataway, N.J.).

Restriction enzymes, T4 DNA ligase and DNA polymerase I (Klenow fragment) were purchased from New-England Biolab (Beverly, Mass.). DNA sequencing kits, PCR kits, and GENESCAN-500 (TAMRA) Size Standard were purchased from Applied Biosystems Division of Perkin-Elmer Corporation (Foster City, Calif.). Pfu DNA polymerase, PCR buffer and TaqPlus Precision PCR kit were purchased from Stratagene (La Jolla, Calif.). Protein assay kit was obtained from Bio-Rad (Hercules, Calif.).

FB medium (one liter) consisted of 25 gram Bacto tryptone, 7.5 gram yeast extract, 6 gram NaCl, 1 gram glucose, and 50 ml of 1 M Tris-HCl, pH 7.6. MOPS medium was prepared (as described in Neidhardt, F. C., et al., *J. Bacteriol.*, 119(3):736–747) (1974), which is hereby incorporated by reference) as well as culture medium for enterobacteria. Tma endo V sonication buffer consisted of 20 mM HEPES, pH 7.4; 1 mM EDTA, pH 8.0; 0.1 mM DTT; 0.15 mM PMSF; 50 mM NaCl. GeneScan stop solution consisted of 80% formamide (Amresco, Solon, Ohio), 50 mM EDTA (pH 8.0), 1% blue dextran (Sigma Chemicals). TB buffer (1×) consisted of 89 mM Tris and 89 mM boric acid. TE buffer consisted of 10 mM Tris-HCl, pH 8.0 and 1 mM EDTA.

Proteinase K was purchased from QIAGEN (Valencia, Calif.). Microcon 30 filters were purchased from Millipore (Bedford, Mass.). Taq DNA polymerase FS and four dideoxynucleotides were provided generously by PerkinElmer. Sep-Pak Cartridge C-18 was purchased from Waters (Milford, Mass.). Centri-Sep™ spin column P/N CS-90 was purchased from Princeton Separation (Adelphia, N.J.).

Thermus species AK16D DNA ligase was cloned, overexpressed in *E. coli.* and purified to homogeneity as described in Tong, J., et al., "Biochemical Properties of a High Fidelity DNA Ligase from *Thermus* Species AK16D," *Nucleic Acids Res* 27:788–94 (1999), which is hereby incorporated by reference.

Example 2

Plasmid Construction, Cloning, Expression, and Purification of *Thermotoga maritima* Endonuclease V Through BLAST searches (Altschul, S. F., et al., *J. Mol. Biol.*, 215(3):403–10 (1990), which is hereby incorporated by reference), a putative open reading frame of 225 amino acid has been identified in the *Thermotoga maritima* genome that shows 34% sequence identity to the *E. coli* endonuclease V gene. To prove that this, Tma ORF indeed encodes an endonuclease V, it was cloned and overexpressed in *E. coli*.

The putative endonuclease V gene (nfi) from *Thermotoga maritima* was amplified by PCR using forward primer EV.Tma.01A (5' GGA GGG AAT CATATG GAT TAC AGG CAG CTT CAC A 3' (SEQ. ID. No. 3), the NdeI site is underlined) and reverse primer EV.Tma.02R (5' GCG CCT GGATCCACTAGT TCA GAA AAG GCC TTT TTT GAG CCG T 3' (SEQ. ID. No. 4), the SpeI and BamHI sites are underlined). The PCR reaction mixture (100 μl) consisted of 50 ng of *Thermotoga maritima* genomic DNA, 10 μM of forward primer EV.Tma.01A, 10 μM of reverse primer EV.Tma.02R, 1×Pfu PCR buffer, 100 μM of each dNTP, and 2.5 U Pfu DNA polymerase (Stratagene, La Jolla, Calif.). The PCR procedure included a pre-denaturation step at 95° C. for 2 min, 25 cycles of two-step amplification with each cycle consisting of denaturation at 94° C. for 30 sec and annealing-extension at 60° C. for 6 min, and a final extension step at 72° C. for 5 min. The PCR product was purified by routine phenol extraction and ethanol precipitation to remove thermostable Pfu DNA polymerase. Sambrook, J. et al., *Molecular Cloning-A Laboratory Manual*, 2nd Ed., Cold Spring Harbor Laboratory Press, Cold Spring Harbor, N.Y. (1989), which is hereby incorporated by reference. The purified PCR product was digested with NdeI and BamHI, and ligated to pEV1 vector digested with the same pair of restriction enzymes. pEV1 is a derivative of pFBT69 (Barany, F., *Gene*, 63:167–177 (1988), which is hereby incorporated by reference) which contains an NdeI site after the Shine-Dalgarno sequence in the phoA promoter region and a downstream multiple cloning site (BamHI-KasI-BstXI-EcoRV-EcoRI-MluI). The plasmid containing the putative Tma endonuclease V gene was designated as pEV5 and transformed into *E. coli* strain AK53 by a one-step protocol as described in Chung, C. T., et al., *Proc. Natl. Acad. Sci. USA*, 86(7):2172–75 (1989), which is hereby incorporated by reference. The endonuclease V gene is regulated by a phoA promoter. The insert containing Tma endonuclease V gene was sequenced to ensure authenticity of the plasmid constructs.

Overnight *E. coli* culture containing pEV5 was diluted 100-fold into FB medium supplemented with 50 μg/ml ampicillin. The *E. coli* cells were grown at 37° C. with 200 rpm shaking to an absorbance at 550 nm of 0.8. The cultures were diluted 50-fold into 1 liter of MOPS medium supplemented with 50 μg/ml ampicillin, and grown under the same conditions overnight. After centriffigation at 3000×g for 10 min, the cell pellets were suspended in 10 ml of Tma endo V sonication buffer (20 mM HEPES, pH 7.4; 1 mM EDTA, pH 8.0; 0.1 mM DTT; 0.15 mM PMSF; 50 mM NaCl ) and sonicated on ice for two to three times at ten seconds each.

To purify the endonuclease V protein, cell debris were removed by centrifuigation at 3000×g for 15 min. The supernatants were incubated at 70° C. for 15 min to denature thermolabile *E. coli*. host proteins. After separating inactivated *E. coli* proteins by centrifugation at 10,000×g for 20 min, the supernatants were dialyzed against the starting buffer (50 mM HEPES, pH 7.4, 1 mM EDTA, 50 mM NaCl, 0.1 mM DTT) overnight.

FIG. 2 shows a 12.5% SDS-PAGE gel demonstrating the purification of *Thermotoga maritima* endonuclease V protein at various stages in the process. Lane 2 shows the total proteins released from *E. coli*. cells. Since most *E. coli* host proteins are thermolabile, while Tma endo V is thermostable, the lysate was heated at 70° C. for 15 min in order to inactive most *E. coli* host proteins (including *E. coli*. endo V, See Example 4) while maintaining Tma endo V activity. After heat treatment, inactivated *E. coli* host proteins aggregate, and the majority of host proteins can be pelleted and removed by centrifugation. This leaves Tma endo V as the major protein in the supernatant, as demonstrated in FIG. 2 Lane 3 which shows proteins in the supernatant after heat treatment and centrifugation. Tma endonuclease V eluted at about the 24 kDa position, indicating that it exists as monomer in solution (FIG. 2B).

Tma endonuclease V was purified to near homogeneity using a HiTrap SP column containing sulphopropyl functional group (Pharmacia). In a buffer at pH 7.4, Tma endonuclease V carries a net positive charge, making it a compatible substrate for the HiTrap SP. The column was then either washed stepwise with elution buffers containing increasing amounts of NaCl, or washed with a buffer containing a NaCl concentration gradient in conjunction with an FPLC or HPLC system. Elution of a protein from the column is dependent on a particular NaCl concentration for that protein. In the stepwise elution, proteins were eluted with 150 mM NaCl to 500 mM NaCl at 50 mM interval. Pure Tma Endo V was eluted with 250–300 mM NaCl. FIG. 2, lane 4 demonstrates that the enzyme from the elution with 250–300 mM NaCl is nearly homogeneous. The concentration of the enzyme was then determined by the ultraviolet absorption method: protein concentration=A(280)×OD 280. Wetlaufer, D. B., *Adv. Prot. Chem.* 17:303–390 (1962), which is hereby incorporated by reference. For Tma endo V, 1A=0.89 mg/ml, which was calculated by using the Protean software program (Power Macintosh version 3.05, DNA Star Inc.) and based on the protein sequence of Tma endo V. The Tma endo V protein sequence (nfi gene) is available at the TIGR Microbial Database Locus TM1865 at web site: http://www.tigr.org/tdb/, under the section *Thermotoga maritima*.

To ensure that the purified Tma endonuclease V as shown in FIG. 2 is devoid of endogenous *E. coli* endonuclease V which has a similar molecular weight, the protein was transferred to a PVDF membrane and subjected to N-terminal sequencing according to the procedure used in Cao, W. et al., *J. Biol. Chem.*, 273(49):33002–10 (1998), which is hereby incorporated by reference. The peptide sequencing result matched the predicted N-terminal sequence of Tma nfi gene. Additionally, a 70° C.-15 min heat-treatment was performed on *E. coli* endonuclease V purchased from a commercial source (Trevigen, Gaithersburg, Md.). While the untreated enzyme was active as reported, the heat-treated enzyme lost its enzymatic activity. Thus, the heating step used in purification is likely to have inactivated *E. coli* endonuclease V Example 3

Oligonucleotide Substrates Preparation

Figure 3:
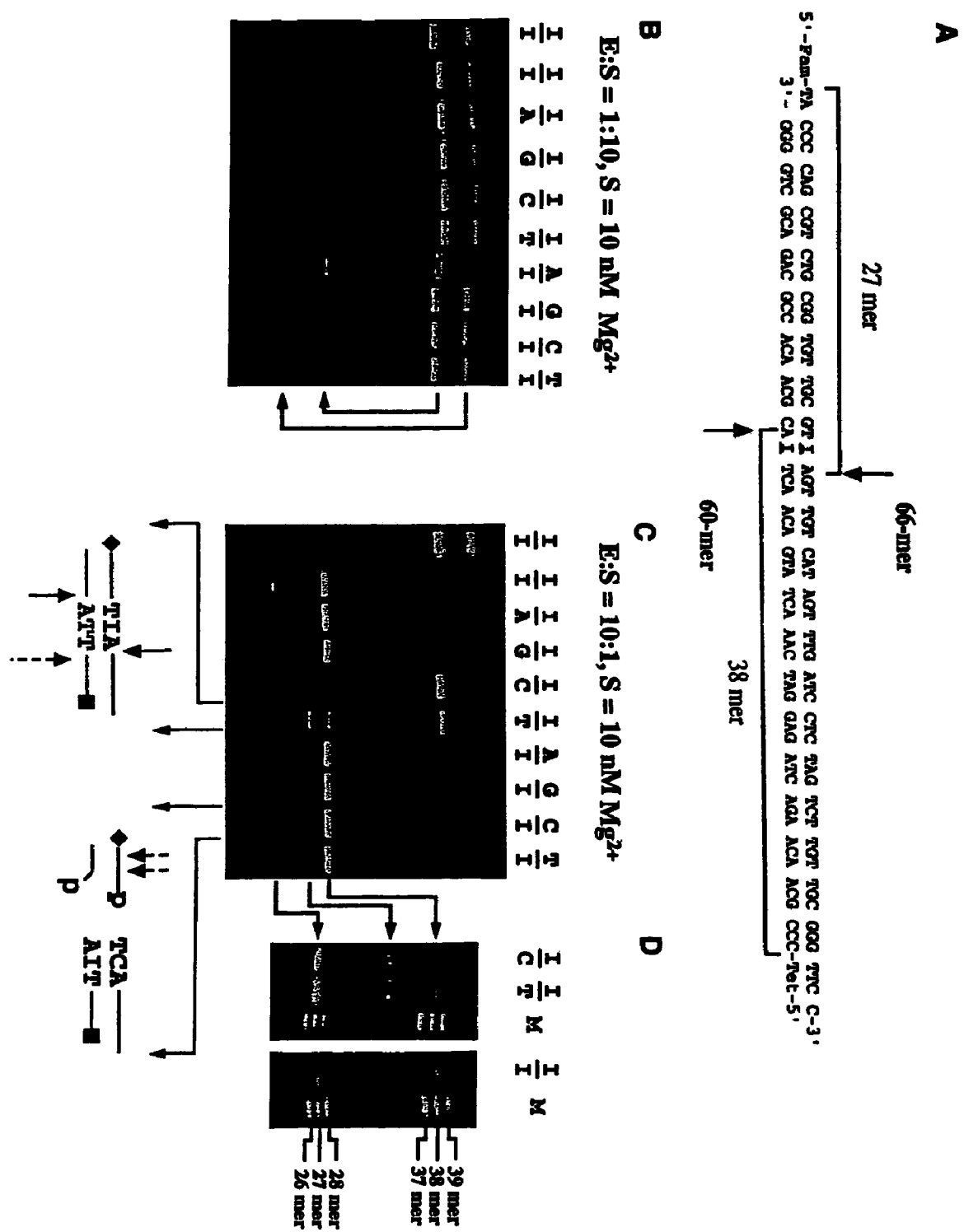
FIGS. 3A–D show clevage assays of Tma endonuclease V on double-stranded inosine-containing substrates.

*E. coli* endonuclease V demonstrates high activity with double-stranded DNA strands containing deoxyinosine-deoxyinosine or deoxyinosine-base mismatch. Yao, M. and Kow, Y. W., *J. Biol. Chem.*, 269(50):31390–96 (1994), which is hereby incorporated by reference. This general characteristic of endo V was used in order to functionally identify the purified Tma endo V enzyme. A double-stranded oligonucleotide containing a base mismatch was designed as a substrate to monitor for cleavage activity by the purified enzyme. FIG. 3A shows a simple assay system using two differentially labeled fluorescent oligonucleotides. The top strand is labeled with 6-FAM and the bottom strand is TET labeled. The mismatch position of the deoxyinosine nucleotide is off-center so that nicked products do not comigrate on a denaturing polyacrylamide gel. The differential double labeling allows the nicking events on both strands to be easily observed and distinguished on the gel.

Oligonucleotide DNA substrates were purified on denaturing sequencing gels (7 M urea/10% polyacrylamide) as described in "The Complete Guide: Evaluating and Isolating Synthetic Oligonucleotides" (Applied Biosystems Inc., Foster City, Calif.)). Purified oligonucleotides were dissolved in TE buffer. Equal molar concentration of two complementary single strands were mixed and incubated at 85° C. for 3 min and allowed to form duplex DNA substrates at room temperature for 30 min.

Example 4

Cleavage of Deoxyinosine-Containing Oligonucleotides

In order to functionally identify the purified enzyme, deoxyinosine-containing substrates were initially used since *E. coli* endonuclease V shows high activity toward an deoxyinosine-containing strand. Yao, M. et al., *J. Biol. Chem,* 269(50):31390–96 (1994), which is hereby incorporated by reference.

The cleavage reactions were performed at 65° C. for 30 minute in a 20 μl reaction mixture containing 10 mM HEPES (pH 7.4), 1 mM DTT, 2% glycerol, 5 mM $MgCl_2$ unless otherwise specified, 10 nM DNA substrate, and the indicated amount of purified Tma endonuclease V protein. The reaction was terminated by adding an equal volume of GeneScan stop solution. The reaction mixtures were then heated at 94° C. for 2 min. and cooled on ice. Three microliter samples were loaded onto a 10% GeneScan denaturing polyacrylamide gel (Perkin Elmer). Electrophoresis was conducted at 1500 voltage for 1 hr using an ABI 377 sequencer (Perkin Elmer). Cleavage products and remaining substrates were quantified using the GeneScan analysis software versions 2.1 or 3.0.

At a low enzyme concentration (E:S=1:10, S=10 nM, E:S stands for the ratio of enzyme-to-substrate, S stands for substrate), Tma endonuclease V nicked exclusively at deoxyinosine-containing strands regardless of whether deoxyinosine was placed on the top or bottom strand or both (FIG. 3B). Cleavage was efficient for all four kinds of deoxyinosine base-pair (I/A, I/G, I/C, I/T), confirming a previous observation with the *E. coli* enzyme. Yao, M. et al., *J. Biol. Chem,* 269(50):31390–96 (1994), which is hereby incorporated by reference. The predominant products were formed by nicking at the 3' side one nucleotide after the inosine base on both strands (FIG. 3D). At a high enzyme concentration (E:S=10:1, S=10 DM), Tma endonuclease V nicked deoxyinosine-containing strands effectively, resulting in virtually complete conversion to nicked products (FIG. 3C). In contrast to the results obtained with the low enzyme concentration (FIG. 3B), the high enzyme concentration promoted opposite strand nicking (e.g., nicking the A-containing strand in a dI/dA duplex oligonucleotide substrate). For I/A and I/G substrates, the nicking primarily occurred at the 3' side one nucleotide beyond the mismatched A or G base. However, opposite strand nicking for I/C and I/T substrates generated an additional product at a lower molecular weight position (FIG. 3C). Comparison with length markers suggested that the cleavage site was approximately 2–3 nt at the 5' side of the T or C base as the 38 mer and 27 mer represent cleavage products right after the T or C base at the 3' side (FIG. 3D). The opposite strand nicking was incomplete at I/C and I/T, while the deoxyinosine cleavage was complete, indicating that the 5' nicking of C or T had occurred after nicking of the deoxyinosine-containing strand. It is unknown whether the high yield opposite strand nicking at the 5' side in I/C is associated with the fact that I/C forms a Watson-Crick base-pair (Xuan, J. C. et al., *Nucleic Acids Res.*, 20:5457–64 (1992), which is hereby incorporated by reference) and whether the low yield opposite strand nicking at the 5' side in I/A and I/G is associated with the fact that they form non-Watson-Crick base-pairs. Corfield, P. W., et al., *Nucleic Acids Res.*, 15(19): 7935–49 (1987), which is hereby incorporated by reference. The opposite strand nicking at the 5' side of the I/C and I/T base-pairs was not observed with C/I or T/I substrates, indicating that either the nicking products were less stable at 65° C. incubation and being degraded as single-stranded DNA or the nicking at these substrates were less efficient due to sequence context. These results suggest that nicking events in general occur at the 3' side, but the enzyme is capable of cleaving at the 5' side at the opposite strand complementary of an deoxyinosine-containing strand. An earlier study suggested that *E. coli* endonuclease V cleaves at the 5' side of methylbenz[a]anthracene adducts. Demple, B. et al., *J. Biol. Chem.*, 257(6):2848–55 (1982), which is hereby incorporated by reference. Thus, the enzyme is able to make a 5' incision at some lesion sites. The above results confirmed that the purified enzyme is an endonuclease V.

Example 5

Effect of Reaction Buffer on Tma Endonuclease V Activity and Specificity

Since enzyme activity and specificity can be influenced by the metal cofactor used by an enzyme, Tma endo V mismatch cleavage activity in the presence of either $Mg^{2+}$, $Mn^{2+}$, $Fe^{2+}$, $Ca^{2+}$, $Co^{2+}$, $Ni^{2+}$, $Cu^{2+}$, $Zn^{2+}$, $Cd^{2+}$, $Ba^{2+}$ or $Sr^{2+}$ was analyzed. The concentration of each metal was 5 mM. The reaction mixture contained 10 mM HEPES (pH 7.4), 1 mM DTT, 2% glycerol, 5 mM metal chloride, 100 nM Tma endo V and 10 nM oligonucleotides containing base-mismatch either (A/A), or (C/T), or (C/C), a regular oligonucleotide without base mismatch was used as a control. The mixture was incubated at 65° C. for 30 min and loaded on a gel for electrophoresis. Cleavage products and remaining substrates were quantified using the GeneScan analysis software versions 2.1 or 3.0. Cleavage products were only observed in the presence of $Mg^{2+}$ or $Mn^{2+}$, indicating that these two cations are the only metal cofactors of Tma endo V in the set tested. FIG. 4 shows Tma endo V activity in the presence of different concentrations of $Mg^{2+}$ or $Mn^{2+}$ using double-stranded oligonucleotide DNA with an A/A mismatch as substrate. The mismatch cleavage activity was most active at $Mg^{2+}$ concentrations of 2–7 mM and at $Mn^{2+}$ concentrations of 0.4–1.2 mM.

Example 6

Cleavage of Base Mismatch-Containing Oligonucleotides

Figure 5:
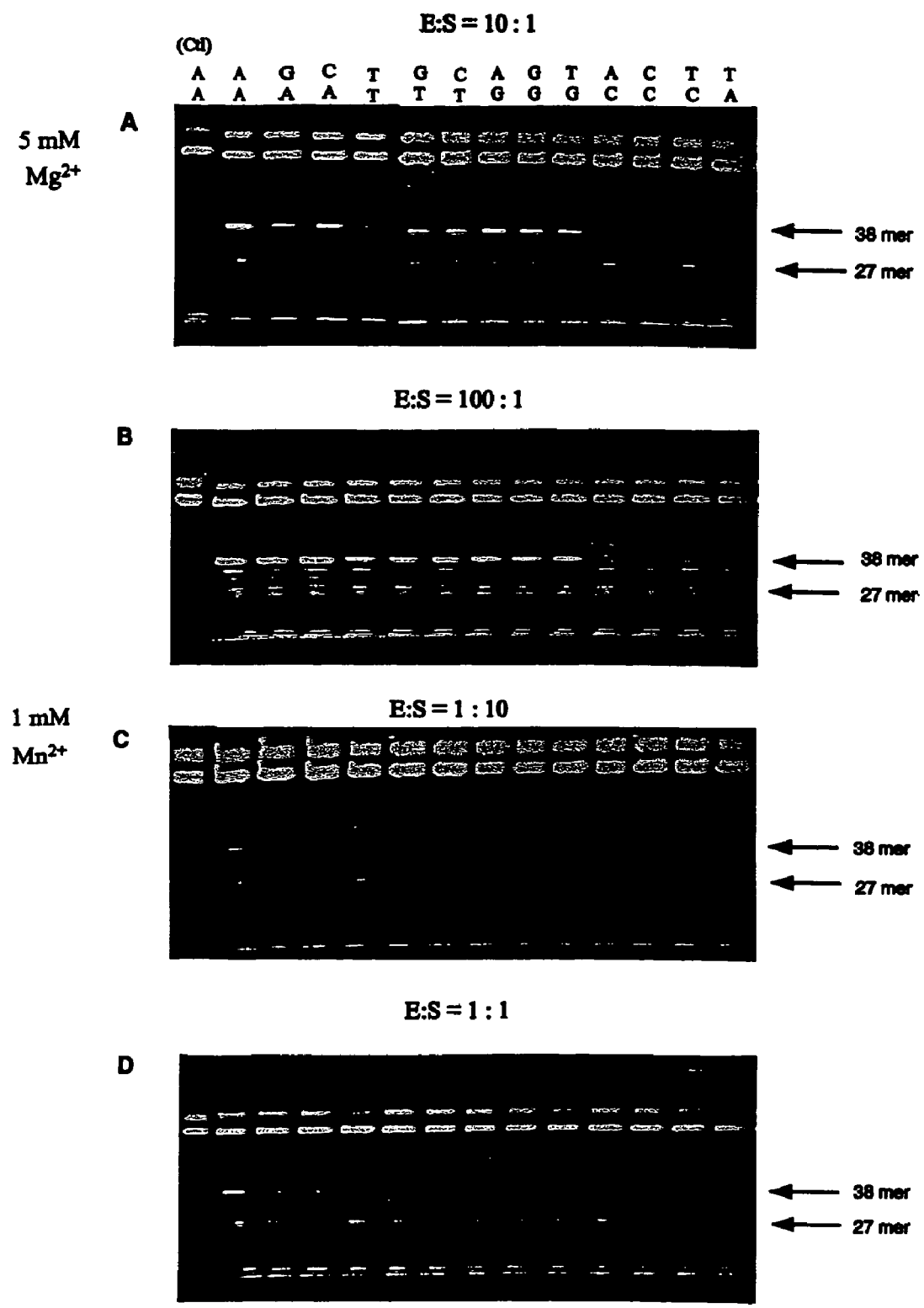
FIGS. 5A–D demonstrate the ability of Tma endonuclease V to cleave a variety of different single base mismatches in the presence of $Mg^{2+}$ or $Mn^{2+}$.

Base mismatch nicking was investigated using 12 substrates containing different base mismatches (FIG. 5). The cleavage reactions were performed at 65° C. for 30 minute in a 20 µl reaction mixture containing 10 mM HEPES (pH 7.4), 1 mM DTT, 2% glycerol, 5 mM $MgCl_2$ or 1 mM $MnCl_2$, 10 nM DNA substrate and the indicated amount of purified Tma endonuclease V protein. The reaction was terminated by adding an equal volume of GeneScan stop solution. The reaction mixtures were then heated at 94° C. for 2 min. and cooled on ice. 3 µL of samples were loaded onto a 10% GeneScan denaturing polyacrylamide gel (Perkin Elmer). Electrophoresis was conducted at 1500 voltage for 1 hr using an ABI 377 sequencer (Perkin Elmer). Cleavage products and remaining substrates were quantified using the GeneScan analysis software versions 2.1 or 3.0. With $Mg^{2+}$ as the metal cofactor, the enzyme needed a higher enzyme-to-substrate (E:S) ratio to make an incision at a mismatch (FIGS. 5A–5B). With $Mn^{2+}$ as the metal cofactor, the nicks at mismatch substrates occurred at lower E:S ratios (FIGS. 5C–5D). The cleavage reactions of mismatches did not proceed to completion, as even at higher E:S ratios there were still significant remaining mismatch containing substrates while the nonspecific nicking became significant (FIG. 5B). The cleavage sites were identical to those identified using deoxyinosine-containing substrates, i.e., at the 3' side one nucleotide after the mismatches. The mismatch nicking was most efficient with an A or G base, and less so with a T base. C base was nicked much less efficiently when it base-pairs with an A or a T base, and cleavage was not observed when it base-pairs with a C. This mismatch cleavage profile is in agreement with the *E. coli* enzyme. Yao, M. et al., *J. Biol. Chem.*, 269(50):31390–96 (1994), which is hereby incorporated by reference. However, no strand-preferred or terminus-dependent mismatch cleavage was observed as previously reported using the *E. coli* enzyme (Yao, M. et al., *J. Biol. Chem.*, 269(50): 31390–96 (1994), which is hereby incorporated by reference). Base mismatch cleavage occurred at both top and bottom strands regardless of the distance between the mismatch base and the 5' termini (FIG. 2A, FIG. 5A). The finding that Tma Endo V was capable of cleavage of both top and bottom strands regardless of the distance between the mismatch base and the 5' termini was unanticipated and demonstrates that this enzyme has unique properties which distinguish it from the *E. coli* enzyme. The same authors who characterized the mesophilic *E. coli* Endo V enzyme most recently characterized the thermostable *A. fulgidus* Endo V enzyme (Liu et. al., *Mutation Research* 461:169–177 (2000). The *A. fulgidus* Endo V enzyme only had activity against inosine containing DNA, not against mismatches or other lesions. Thus, it cannot be presumed that a thermostable Endo V would have activity on substrates containing base mismatches.

Table 1 provides a summary of results with Tma endonuclease V cleavage of heteroduplexed synthetic substrates containing single base mismatches. Note that for every possible base change, there are two possible heteroduplexed products which may form: A⇌G (A-C, G-T); C⇌T (C-A, T-G); A⇌C (A-G, C-T); G⇌T (G-A, T-C); A⇌T (A-A, T-T), and G⇌C (G-G, C-C).

TABLE 1

Summary of Tma endonuclease V cleavage of heteroduplexed synthetic substrates containing single base mismatches.

| Base change (Wt↔Mt) | A↔G | C↔T | A↔C | G↔T | A↔T | G↔C |
|---|---|---|---|---|---|---|
| Heteroduplex I: | | | | | | |
| UpperStrand (Wt) | A +++ | C + | A ++ | G ++ | A +++ | G +++ |
| | \| | \| | \| | \| | \| | \| |
| BottomStrand (Mt) | C − | A ++ | G +++ | A ++ | A +++ | G +++ |
| Heteroduplex II: | | | | | | |
| UpperStrand (Mt) | G ++ | T ++ | C + | T ++ | T + | C − |
| | \| | \| | \| | \| | \| | \| |
| BottomStrand (Wt) | T ++ | G +++ | T ++ | C − | T + | C − |

Note:
UpperStrand:
5'-FAM-TA CCC CAG CGT CTG CGG TGT TGC GTN AGT TGT CAT AGT TTG ATC CTC TAG TCT TGT TGC GGG TTCC-3' (SEQ. ID. No. 5)
BottomStrand:
3'- GGG GTC GCA GAC GCC ACA ACG CAN TCA ACA GTA TCA AAC TAG GAG ATC AGA ACA ACG CCC-TET-5' (SEQ. ID. No. 6)
Cleavage symbols:
+++: high intensity cleavage. ++: intermediate intensity cleavage. +: low intensity cleavage. − no cleavage The cleavage of these heteroduplexed products are not always identical (i.e. compare A-C with C-A), and this reflects subtleties in the structure of the DNA as a consequence of neighboring sequence variation. Nevertheless, for each possible base change, signal is generated for at least one top strand and at least one bottom strand. Thus, the Tma EndoV enzyme should be able to recognize any possible single base mutation or polymorphism.

Example 7

Non-Specific Cleavage Activity of Tma Endonuclease V on Single Stranded and Double Stranded DNA In order to determine the non-specific cleavage activity of Tma endo V, the cleavage activities on a single strand oligonucleotide and a regular plasmid were measured. The single strand DNA cleavage reactions were performed at 65° C. for 30 minute in a 20 µl reaction mixture containing 10 mM HEPES (pH 7.4), 1 mM DTT, 2% glycerol, in 5 mM MgCl$_2$ or 0.6 mM MnCl$_2$, 10 nM single strand DNA substrate, and the indicated amount of purified Tma endonuclease V protein.

The plasmid cleavage reactions were performed at 65° C. for 30 minute in a 20 µl reaction mixture containing 10 mM HEPES (pH 7.4), 1 mM DTT, 2% glycerol, 5 mM MgCl$_2$ or 1 mM MnCl$_2$, 10 nM plasmid pFB 7.6, and the indicated amount of purified Tma endonuclease V protein.

The reaction was terminated by adding an equal volume of GeneScan stop solution. The reaction mixtures were then heated at 94° C. for 2 min. and cooled on ice. Three microliter of samples were loaded onto a 10% GeneScan denaturing polyacrylamide gel (Perkin Elmer). Electrophoresis was conducted at 1500 voltage for 1 hr using an ABI 377 sequencer (Perkin Elmer). Cleavage products and remaining substrates quantified using the GeneScan analysis software versions 2.1 or 3.0.

Figure 6:
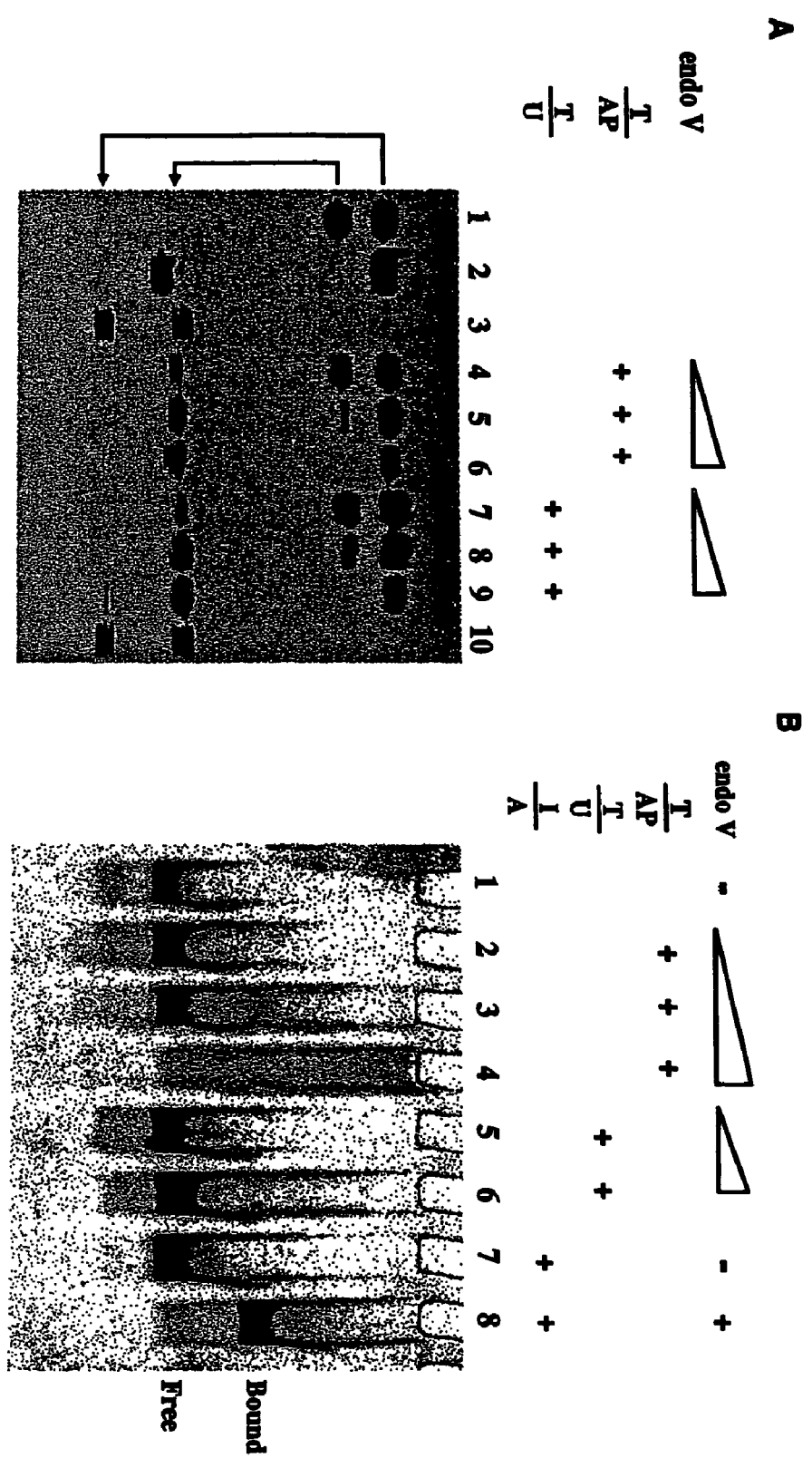
FIGS. 6A–B show the cleavage and binding of AP and uracil sites.
FIGS. 6C–G show single stranded and nonspecific cleavage and binding by Tma endonuclease V.
Figure 6:
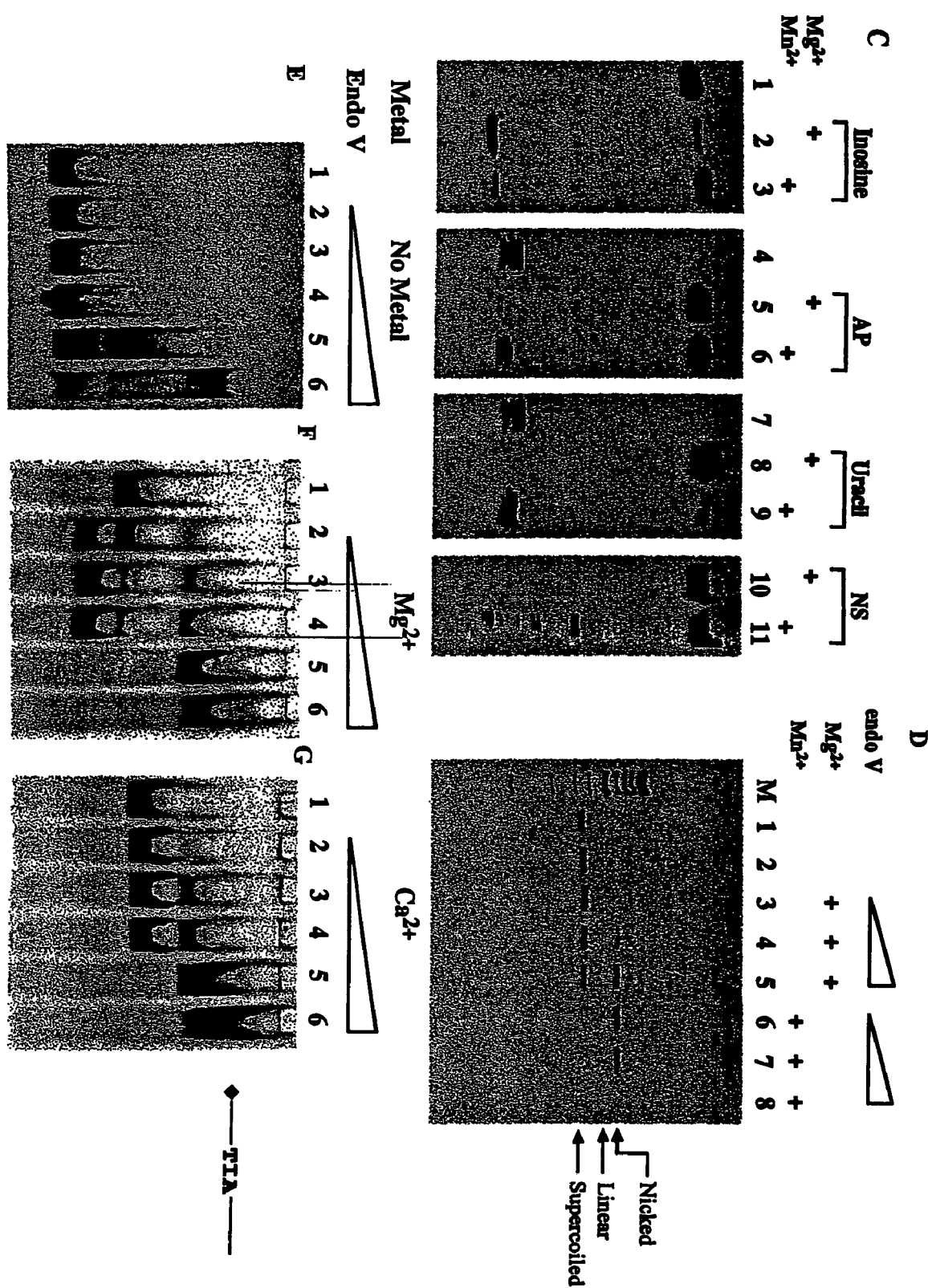

The enzyme nicked the AP site or uracil-containing strand specifically at low enzyme concentrations (FIG. 6A, lanes 3–4 and 6–7). When the enzyme concentration was increased to 100 nM (E:S=10:1), opposite strand nicking started to occur (FIG. 6A, lanes 5 and 8), suggesting that opposite strand nicking is not unique to inosine-containing substrates. The enzyme formed a weak but distinct complex with an AP site substrate, but not with a uracil substrate (FIG. 6B), suggesting that the enzyme does not solely rely on base recognition for achieving ground state binding. The lack of stable binding to a uracil site is consistent with genetic studies which indicate that endo V does not play a significant role in uracil repair. Guo, G. et al., *J. Bacteriol*, 180:46–51 (1998), which is hereby incorporated by reference.

The binding data obtained from I/I substrate showed that the enzyme may be able to interact with inosine substrate in a single-stranded fashion. Previous studies demonstrate that *E. coli* endo V cleaves single-stranded inosine substrate (Yao, et al., *J. Biol. Chem.*, 271:30672–76 (1996), which is hereby incorporated by reference). To gain a better understanding of how the enzyme cleaves single stranded DNA, cleavage and binding of inosine, AP site, and uracil substrates were examined. Tma endo V cleaved single stranded inosine substrate with either Mg$^{2+}$ or Mn$^{2+}$ as the metal cofactor (FIG. 6C). The cleavage of single stranded AP site or uracil appeared to prefer using Mn$^{2+}$ as the metal factor (FIG. 6C). In addition, Mn$^{2+}$ promoted the cleavage of non-specific single stranded DNA (FIG. 6C). The nonspecific endonuclease activity was further confirmed using a supercoiled plasmid substrate (FIG. 6D). With Mg$^{2+}$ as the metal cofactor, the non-specific endonuclease activity primarily nicked the plasmid once. With Mn$^{2+}$ as the metal cofactor, the enzyme could nick a plasmid molecule at least twice to generate a linear plasmid (FIG. 6D). The two nicking events are sequential as evidenced by the appearance of nicked plasmid intermediate. The conversion of supercoiled plasmid into nicked or linear plasmid suggests that the enzyme does not need free 5' or 3' ends to access a DNA molecule.

As with the double stranded inosine substrate, binding to single-stranded inosine substrate also requires a metal cofactor (FIG. 6E). The binding affinity to the single-stranded inosine substrate appeared to be weaker than the double-stranded (FIG. 6E). A stable complex was formed in the presence of Mg$^{2+}$, suggesting that Tma endo V maintained a relatively high affinity to the nicked single-stranded product (FIG. 6F). Single-stranded inosine cleavage activity may help repair damage at transient single-stranded regions during replication and transcription.

This indicates that nonspecific cleavage is more prevalent with Mn$^{2+}$ as the metal cofactor. In addition, the conversion of a supercoiled plasmid into nicked and linear forms suggests that the enzyme does not need free 5' or 3' end to access a DNA molecule. Since the above results demonstrate that Tma endo V cleavage is more specific in the presence of Mg$^{2+}$ than Mn$^{2+}$, Mg$^{2+}$ was determined to be the preferred metal cofactor in the reaction buffer.

Example 8

The Effects of pH on the Base-Mismatch Cleavage Activity of Tma Endonuclease V pH can exert a profound effect on mismatch cleavage. The substrates in this assay are a group of four oligonucleotides, three of them contain mismatches (A/A), (C/T), and (C/C) respectively, the other is a regular oligonucleotide without mismatch. The cleavage reactions performed at 65° C. for 1 hour in the buffer containing 10 mM HEPES (pH 7.4), 1 mM DTT, 2% glycerol, 5 mM $MgCl_2$ (or 1 mM $MnCl_2$), 10 nM DNA substrate, indicated that the amount of purified Tma endonuclease V protein with different E:S ratios.

The following buffers were used in making different pH: 20 mM MES (pH 6.0), 20 mM MOPS (pH 6.5), 10 mM HEPES (pH 7.0–7.5), 20 mM Tris (pH 8.0–8.5). A. Reactions performed with 100 nM endonuclease V (E:S=10:1) in the presence of 5 mM $MgCl_2$. B. Reactions performed with 10 nM endonuclease V (E:S=1:1) in the presence of 1 mM $MnCl_2$.

The reaction mixtures were then heated at 94° C. for 2 min. and cooled on ice. Three microliter samples were loaded onto a 10% GeneScan denaturing polyacrylamide gel (Perkin Elmer). Electrophoresis was conducted at 1500 voltage for 1 hr using an ABI 377 sequencer (Perkin Elmer). Cleavage products and remaining substrates were quantified using the GeneScan analysis software versions 2.1 or 3.0.

Figure 7:
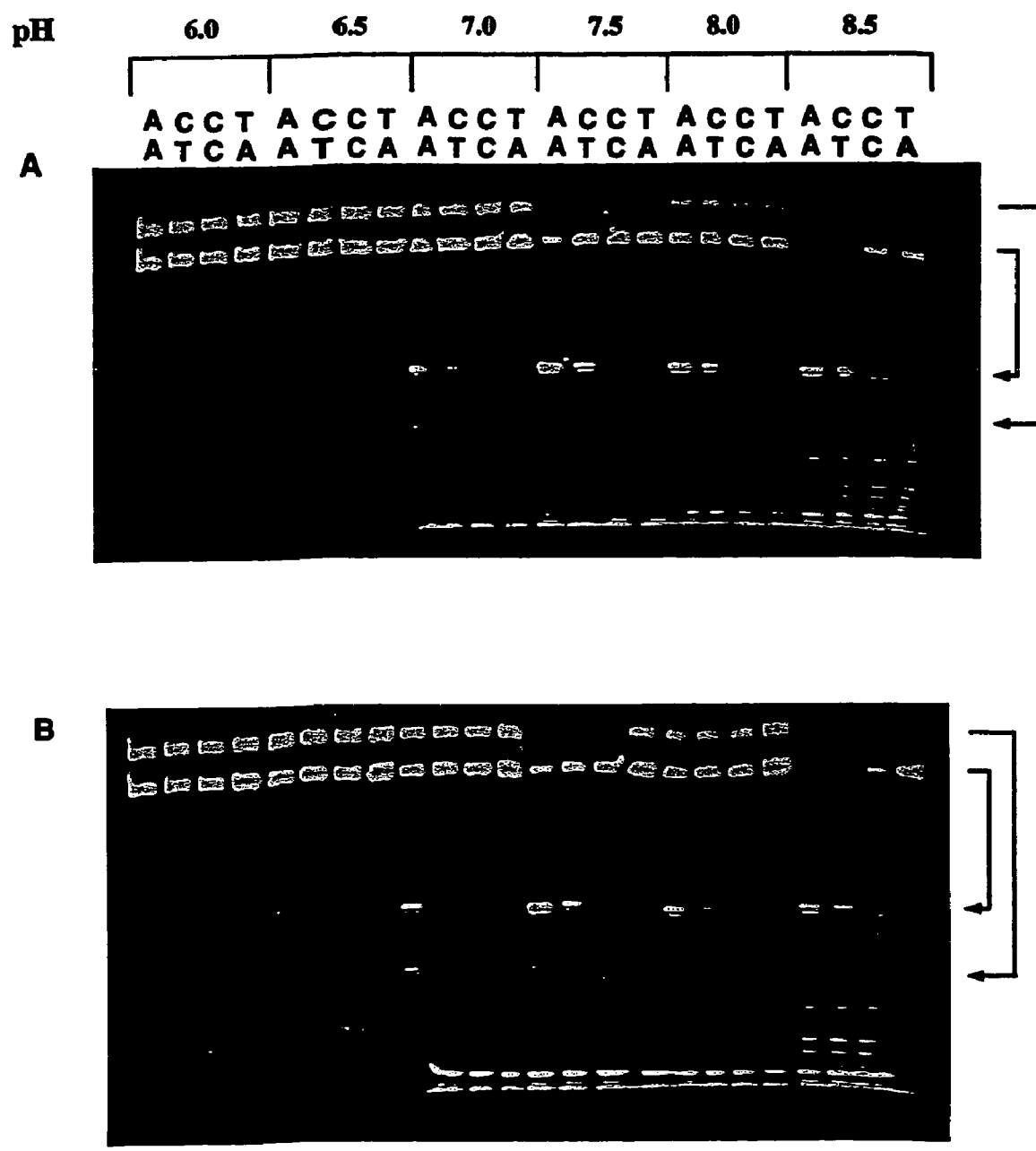
FIGS. 7A–B show the effect of pH on the base-mismatch cleavage activity of Tma endonuclease V.

FIG. 7 shows that the pH of the reaction buffer can exert profound effects on mismatch cleavage. Nicks at the mismatch position became observable at pH 6.5 and reached a maximum at pH 7.5 with concurrent increases in nonspecific cleavage both in the presence of either 5 mM $Mg^{2+}$ (E:S=10:1), FIG. 7A, or 1 mM $Mn^{2+}$ (E:S=1:1) FIG. 7B. Consistent with previous studies for *E. coli* endonuclease V, (Gates, F. T., 3rd and Linn, S., *J. Biol. Chem.*, 252(5):1647–53 (1977), which is hereby incorporated by reference) and *E. coli* DNA polymerase (Eckert, K. A., et al., "Effect of Reaction pH on the Fidelity and Processivity of Exonuclease-Deficient Klenow Polymerase" *J. Biol. Chem.*, 268(18):13462–71 (1993), which is hereby incorporated by reference). Tma endonuclease V thus became more nonspecific at high pH conditions.

Example 9

The Effects of Salt on the Cleavage of Oligonucleotides Containing a Base Mismatch To study how reaction conditions may affect base mismatch cleavage, representative mismatch cleavage was tested at different NaCl concentrations. The substrates in this assay were a group of four oligonucleotides, three of them containing (A/A), (C/T), and (C/C) mismatches, respectively, while the other was a regular oligonucleotide without mismatch. The cleavage reactions were performed at 65° C. for 30 minute in a 20 µl reaction mixture containing 10 mM HEPES (pH 7.4), 1 mM DTT, 2% glycerol, 5 mM $MgCl_2$ or 1 mM $MnCl_2$, 10 nM DNA substrate, and the indicated amount of purified Tma endonuclease V protein. The concentration of NaCl ranged from 0–250 mM with 50 mM intervals. The reaction was terminated by adding an equal volume of GeneScan stop solution. The reaction mixtures were then heated at 94° C. for 2 min. and cooled on ice. 3 µL of samples were loaded onto a 10% GeneScan denaturing polyacrylamide gel (Perkin Elmer). Electrophoresis was conducted at 1500 voltage for 1 hr using an ABI 377 Sequencer (Perkin Elmer). Cleavage products and remaining substrates were quantified using the GeneScan analysis software versions 2.1 or 3.0.

Figure 8:
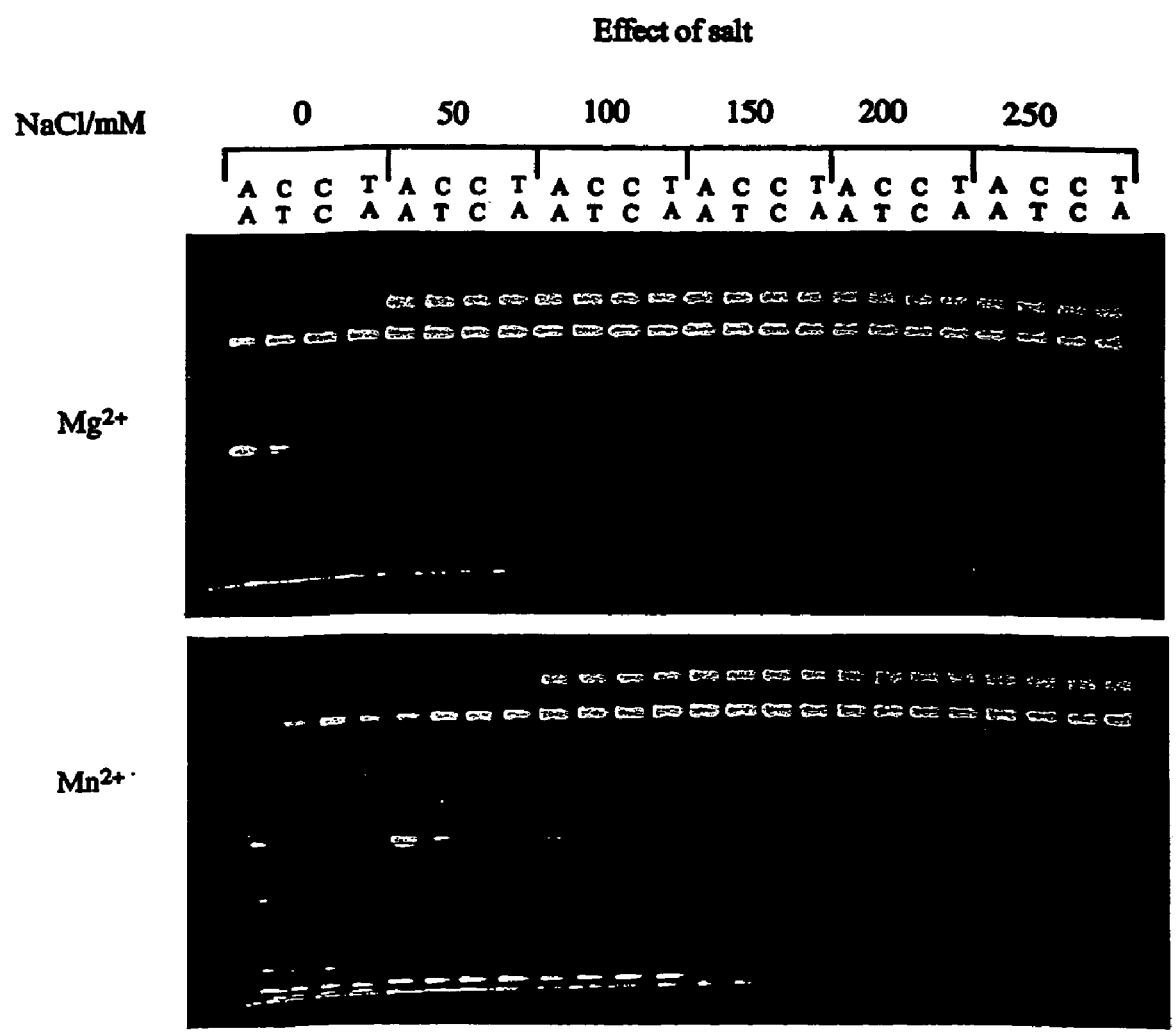
FIG. 8 illustrates the optimal NaCl concentrations for the base-mismatch cleavage activity of Tma endonuclease V.

It was apparent that the enzyme preferred a low salt environment for mismatch cleavage with either $Mg^{2+}$ or $Mn^{2+}$. With $Mg^{2+}$ as the metal cofactor, the mismatch cleavage yields were highest without salt. With $Mn^{2+}$ as the metal cofactor, the mismatch cleavage yields were highest with 50 mM NaCl. See FIG. 8. This is in agreement with the notion that increased salt concentrations reduce DNA binding affinity. No cleavage was observed with either the C-C mismatch or A-T match under these conditions.

From the above experiments, an optimal reaction buffer condition in which Tma endo V mismatch cleavage is maximized and nonspecific mismatch cleavage is minimized was determined. The optimal conditions are 10 mM HEPES (pH 7.4), 1 mM DTT, 2% glycerol, and 5 mM $MgCl_2$. These conditions were determined from data primarily using oligonucleotides as substrate. Therefore, the optimal condition may vary when different substrates, such as genomic DNA, are utilized. In addition, this optimal condition is one that appears best with respect to cleavage characteristics most desirable in the context of the present invention, but it should be noted that sub-optimal conditions are also compatible in the context of the invention.

Example 10

Optimization of $Mg^{2+}$ and $Mn^{2+}$ Concentration in Tma Endonuclease V Cleavage Reaction Condition When Synthetic Oligonucleotide DNA was Used as Substrate Using fluorescences labeled double strand oligonucleotide containing (A/A) mismatch as the substrate, the cleavage activity of Tma endo V was measured in different concentrations of $Mg^{2+}$ or $Mn^{2+}$. The cleavage reactions were performed at 65° C. for 30 minute in a 20 µl reaction mixture containing 10 mM HEPES (pH 7.4), 1 mM DTT, 2% glycerol, unless otherwise specified, 10 nM DNA substrate, different concentrations of $Mg^{2+}$ or $Mn^{2+}$, and 100 nM Tma endo V (in the presence of $Mg^{2+}$) or 10 nM fma endo V (in the presence of $Mn^{2+}$).

The reaction was terminated by adding an equal volume of GeneScan stop solution (50 mM EDTA, 80% formamide, 1% blue dextran). The reaction mixtures were then heated at 94° C. for 2 min. and cooled on ice. 3 µL of samples were loaded onto a 10% GeneScan denaturing polyacrylamide gel (Perkin Elmer). Electrophoresis was conducted at 1500 voltage for 1 hr in an ABI 377 sequencer (Perkin Elmer). Cleavage products and remaining substrates were quantified using the GeneScan analysis software versions 2.1 or 3.0 (Perkin Elmer). The quantitative results are shown in FIG. 4. The optimal concentration for $Mg^{2+}$ is 2–7 mM and for $Mn^{2+}$ is 0.4–1.2 mM in the cleavage of DNA substrate containing a base mismatch.

Example 11

PCR Amplification

Genomic DNA containing mutations in k-ras gene codon 12 and 13 were extracted from cell lines containing the mutations. Cell line ht 29 or sw1417 contains normal genomic DNA. Cell line sw620 or sw480 has DNA containing pure g12v(g→t) mutation. The ratio of wild type-to-mutant g12d(g→a) in the genomic DNA extracted from cell line ls 180 is 1:1.8. The ratio of wild type-to-mutant g12a(g→c) in the DNA extracted from cell line sw1116 is 1:0.7. The ratio of wild type-to-mutant g13d(g→a) in the genomic DNA extracted from cell line hct 15 or dld 1 is 1:1.1.

In carrying out the PCR amplification process, forward and reverse PCR primers can be synthesized with 5' end labels of TET and 6-FAM (PE-Biosystems, Foster City, Calif.). These two fluorescent groups appear green and blue, respectively, when analyzed by an ABI 377 DNA sequencer. Differential labeling of the top and bottom strands allows one to distinguish cleavage products from each strand independently. To minimize non-specific cleavage of TET and 6-FAM labels by Tma endo V, three additional cytosine deoxynuclotides were synthesized on the 5' end of each primer. Examples of suitable primers are shown in Table 1A.

TABLE 2A

PCR Primer Sequences for Amplifying Cancer Gene Fragments.

| Gene | Exon | | Sequence | |
|---|---|---|---|---|
| K-ras | Exon 1 | Top | Tet-5'-CCCCATAGTGTATTAACCTTATGTGTGACATGTTC-3' | (SEQ. ID. No. 7) |
| | | Bottom | Fam-5'-CCCCAAAATGGTCAGAGAAACCTTTATCTGTATC-3' | (SEQ. ID. No. 8) |
| APC | Exon 15 | Top | Tet-5'-CCCCGCTGCCACTTGCAAAGTTTCTTC-3' | (SEQ. ID. No. 9) |
| | | Bottom | Fan-5'-CCCCACTCTGAACGGAGCTGGCAAT-3' | (SEQ. ID. No. 10) |
| p53 | Exon 5 | Top | Tet-5'-CCCCTGTTCACTTGTGCCCTGACTTTC-3' | (SEQ. ID. No. 11) |
| | | Bottom | Fam-5'-CCCCCAGCTGCTCACCATCGCTATC-3' | (SEQ. ID. No. 12) |
| | Exon 6 | Top | Tet-5'-CCCCCTCTGATTCCTCACTGATTGCTCTTA-3' | (SEQ. ID. No. 13) |
| | | Bottom | Fam-5'-CCCGGCCACTGACAACCACCCTTAAC-3' | (SEQ. ID. No. 14) |
| | Exon 7 | Top | Tet-5'-CCCGCCTCATCTTGGGCCTGTGTTATC-3' | (SEQ. ID. No. 15) |
| | | Bottom | Fam-5'-CCCGTGGATGGGTAGTAGTATGGAAGAAAT-3' | (SEQ. ID. No. 16) |
| | Exon 8 | Top | Tet-5'-CCCGGACAGGTAGGACCTGATTTCCTTAC-3' | (SEQ. ID. No. 17) |
| | | Bottom | Fam-5'-CCCCGCTTCTTGTCCTGCTTGCTTAC-3' | (SEQ. ID. No. 18) |
| | 1.7 kb | Top | Fam-5'-CCCGCATGGTGGTGCACACCTATAGTC-3' | (SEQ. ID. No. 19) |
| | | Bottom | Tet-5'-CCCAAGCTGTTCCGTCCCAGTAGATTAC-3' | (SEQ. ID. No. 20) |
| BRCA 1 | Exon 2 | Top | Tet-5'-CCCCTCATTGGAACAGAAAGAAATGGATTTATC-3' | (SEQ. ID. No. 21) |
| | | Bottom | Fam-5'-CCCCTCTTCCCTAGTATGTAAGGTCAATTCTGTTC-3' | (SEQ. ID. No. 22) |
| | Exon 20 | Top | Tet-5'-CCCCACTTCCATTGAAGGAAGCTTCTCTTTC-3' | (SEQ. ID. No. 23) |
| | | Bottom | Fam-5'-CCCCATCTCTGCAAAGGGGAGTGGAATAC-3' | (SEQ. ID. No. 24) |
| BRCA 2 | Exon 11 | Top | Tet-5'-CCCCCAAAATATGTCTGGATTGGAGAAAGTTTC-3' | (SEQ. ID. No. 25) |
| | | Bottom | Fam-5'-CCCCTTGGAAAAGACTTGCTTGGTACTATCTTC-3' | (SEQ. ID. No. 26) |
| VHL | Exon 1 | Top | Tet-CCCGACCGCGCGCGAAGACTAC-3' | (SEQ. ID. No. 27) |
| | | Bottom | Fam-5'-CCCAGGGGCTTCAGACCGTGCTATC-3' | (SEQ. ID. No. 28) |
| | Exon 2 | Top | Tet-5'-CCCCACCGGTGTGGCTCTTTAACAAC-3' | (SEQ. ID. No. 29) |
| | | Bottom | FAM-5'-CCCCTGACATCAGGCAAAAATTGAGAA-3' | (SEQ. ID. No. 30) |
| | Exon 3 | Top | Tet-5'-CCCTAGTTGTTGGCAAAGCCTCTTGTTC-3' | (SEQ. ID. No. 31) |
| | | Bottom | Fam-5'-CCCAAACTAAGGAAGGAACCAGTCCTGTATC-3' | (SEQ. ID. No. 32) |

In the process of purification of PCR primers, 200 ng of labeled primers was dissolved in 20 µl of ddH$_2$O and was mixed with an equal volume of formamide. After incubation at about 64° C. for 2 min, the primers were loaded on a 10% polyacrylamide gel containing 7 M urea. After electrophoresis, the gel slices containing pure primers were cut out and soaked in TNE solution (0.1 M Tris-HCl (pH 8.0), 0.5 M NaCl, 5 mM EDTA) at 37° C. overnight. The solution containing gel slices was removed and loaded on a Sep-Pak Cartridge C-18 (Waters, Milford, Mass.) pre-washed with methanol and water. After washing with 20 ml of ddH$_2$O, the primers were eluted out with 2 ml of elution buffer (5 mM TEAA (triethylamine acetate), 50% methanol) and dried with a speed vacuum. The pellets were suspended with TE buffer. PCR reactions were performed in a GeneAmp PCR System 2400 or GeneAmp PCR System 9700. 50 µl of PCR reaction solution contains 10 mM Tris-HCl (pH 8.3), 50 mM KCl, 200 µM of each dNTP, 0.2 µM of primers, 2.5 mM MgCl$_2$, and about 100 ng genomic DNA or amplicons. In the amplification of VHL exon 1 with high GC content, 2% DMSO was included in the PCR reaction mixture.

PCR amplification may be directly from genomic DNA or, alternatively, from amplicon(s) containing the fragment(s) of interest. Thermocycling conditions for the PCR reaction should be adjusted to reduce the amplification of non-specific fragments. Table 2B shows typical thermocycling conditions for various genes.

TABLE 2B

PCR Cycling Conditions for Amplifying Fragments in Different Genes.

| Gene | Exon | DNA polymerase | Initial denature | Cycle reaction cycle number | Cycle reaction reaction | Final extension |
|---|---|---|---|---|---|---|
| K-ras | Exon 1 | AmpliTaq | 94° C. for 2 min | 30 | 94° C. for 15 sec, 60° C. for 2 min | 72° C. for 7 min |
| APC | Exon 15 | Gold Taq | 95° C. for 10 min | 30 | 94° C. for 30 sec 63° C. for 1 min 15 sec | 72° C. for 7 min |
| p53 | Exon 5 Exon 6 | AmpliTaq | 95° C. for 2 min | 35 | 94° C. for 20 sec 65° C. for 2 min | 72° C. for 7 min |
|  | Exon 7 | Gold Taq | 95° C. for 10 min | 35 | 94° C. for 30 sec 60° C. for 30 sec 72° C. for 1 min | 72° C. for 7 min |
|  | Exon 8 | AmpliTaq | 95° C. for 2 min | 35 | 94° C. for 20 sec 65° C. for 2 min | 72° C. for 7 min |
|  | 1.7 kb | TaqPlus precision DNA polymerase mixture | 95° C. for 2 min | 35 | 94° C. for 20 sec 68° C. for 2 min 45 sec | 72° C. for 7 min |
| BRCA 1 | Exon 2 Exon 20 | Gold Taq | 95° C. for 10 min | 35 | 94° C. for 30 sec 60° C. for 30 sec 72° C. for 1 min | 72° C. for 7 min |
| BRCA 2 | Exon 11 |  |  |  |  |  |
| VHL | Exon 1 | AmpliTaq | 95° C. for 2 min | 35 | 94° C. for 20 sec 66° C. for 30 sec 72° C. for 1 min | 72° C. for 7 min |
|  | Exon 2 | AmpliTaq | 95° C. for 2 min | 35 | 94° C. for 20 sec 60° C. for 30 sec 72° C. for 1 min | 72° C. for 7 min |
|  | Exon 3 | AmpliTaq | 95° C. for 2 min | 35 | 94° C. for 20 sec 66° C. for 30 sec 72° C. for 1 min | 72° C. for 7 min |

Note:
for Amplitaq and Taqplus DNA polymerase, after initial denature step, DNA polymerase was added to perform hot start PCR. For gold Taq DNA polymerase, DNA polymerase was included in the reaction mixture before PCR reaction starts. The PCR machine is GeneAmp PCR system 2400 or 9700 (Perkin Elmer).

Example 12

Preparation Of Heteroduplex DNA Substrates

PCR fragments were incubated with proteinase K (20 mg/ml, QIAGEN) in a ratio of 1 µl of proteinase K to 12 µl of PCR products to remove Taq DNA polymerase. The reaction was carried out at 70° C. for 10 min and at 80° C. for 10 min to inactivate the Proteinase K. The mixture was heated at 94° C. for 1 min, 65° C. for 15 min and then cooled down to room temperature to form heteroduplex DNA. For genomic DNA from cell lines containing more mutant than normal DNA, such as cell line LS 180, PCR fragments from normal genomic DNA were added to make the final ratio (mutant-to-wild type) 1:1. The ratio of mutant to wild type in cell line SW1116 is 0.7:1.0, and the pure mutant DNA is not available, so the genomic DNA alone was treated as described in the following text. If the genomic DNA is purified from blood, for example, where the target DNA is a mutation in the APC, BRCA 1, BRCA 2 and VHL genes, the PCR fragments were treated as described before without adding wild-type PCR fragments.

Example 13

Figure 9:
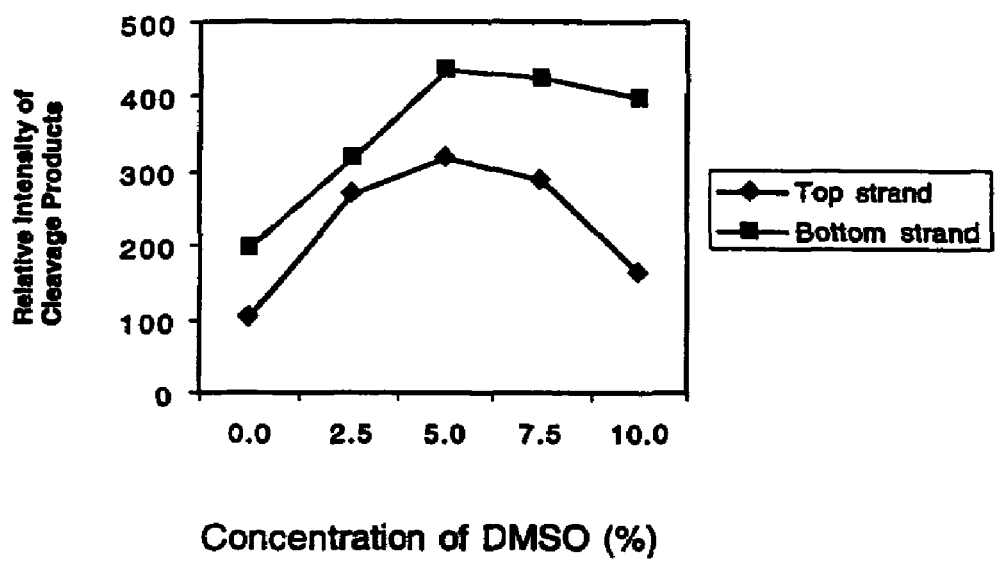
FIG. 9 is a plot of relative intensity of cleavage products v. concentration of DMSO which shows the effect of DMSO concentration on Tma endonuclease V base-mismatch cleavage activity.

Optimization of Conditions of Mutation Detection by Tma endo V/Ligase When Using Heteroduplex PCR Fragments as Substrate When synthetic double stranded oligonucleotides (60–66 mer) were used as the DNA substrate for endo V cleavage, the optimal buffer condition is 10 mM HEPES (pH 7.4), 1 mM DTT, 2% glycerol, 5 mM $MgCl_2$ in which Tma endo V has high specific cleavage activity and low non-specific cleavage activity. However, when an approximately 300 bp PCR fragment containing the G12V mutation in k-ras gene was used as the substrate, cleavage was not observed. For this Tma endo V cleavage assay, a variety of heteroduplex PCR fragments containing K-ras codon 12 mutation were used as substrates. In these experiments, a mixture of wild-type and G12V mutant DNA PCR amplified fragments were used. The two resultant heteroduplexed fragments contain G-A and T-C mismatches, respectively. Cleavage of both top and bottom strand were observed, products were separated on an ABI 377 DNA sequencing apparatus, and amount of cleavage product was quantified using GeneScan 3.0 analysis software (PE-Biosystems, Foster City, Calif.). FIG. 9 demonstrates that adding 5% DMSO to the reaction will enhance mismatch cleavage activity approximately 2–3 fold. Other organic solvents which may enhance mismatch cleavage include dimethyl formamide, ethylene glycol, glycerol, formamide, etc.

A second approach to improving cleavage involved the addition of betaine, N,N,N-trimethylglycine. Betaine was initially used to equalize the melting temperatures of DNA fragments having different GC content. It was found that in certain "isostabilizing" concentrations of betaine, AT and GC pairs are equally stable. Rees, W. A., et al., *Biochemistry*, 32:137–44 (1993), which is hereby incorporated by reference. Betaine was also used as an additive to facilitate PCR amplification of regions with high GC content. Henke, W. et al., "Betaine Improves the PCR Amplification of GC-Rich DNA Sequences," *Nucleic Acids Res.*, 25:3957–58 (1997), which is hereby incorporated by reference.

FIG. 10 shows that the addition of betaine to the reaction buffer can facilitate the base mismatch cleavage activity of Tma. Endo V, but it does so in a fragment dependent fashion. For PCR fragments with a low GC content, such as ones generated from the APC gene, the cleavage activity reached a maximum of 2 fold stimulation at 1.0 M betaine. For PCR fragments with a high GC content, for example the K-ras fragments, maximum cleavage activity was observed at 1.5 M betaine and resulted in a greater stimulation of 2.7 fold. The relative stimulation for both high and low GC content fragments was approximately the same, 2 fold, at 1 M betaine.

The effect of NaCl was also re-examined for heteroduplex fragments, and FIG. 11A demonstrates that addition of NaCl inhibits the cleavage reaction. At 50 mM NaCl, the cleavage reaction is almost completely inhibited. FIG. 11B shows the effect of KCl on the mismatch cleavage activity of Tma endo V. For this assay 100 ng of heteroduplex PCR fragments containing the K-ras G12V (G→T) mutation was used as substrate, and the reaction was carried out at 65° C. for 1 hour in a modified optimal reaction buffer (2.0 M betaine, 10% DMSO) with 100 nM Tma endonuclease V and varying concentrations of KCl. The results show that the effect of KCl is indeed similar to that of NaCl, and that in the presence of 50 mM KCl, Tma endo V cleavage activity is almost completely inhibited. Therefore, in the ligation step of this invention, the Tma endo V cleavage activity is essentially eliminated. These results confirm that no additional salt should be included in the reaction buffer.

The above analysis suggests that when PCR fragments are used as substrates, the addition of 5% DMSO and 1–1.5 M betaine to the reaction can significantly enhance specific cleavage activity of Tma endo V, while the addition of salt should be avoided.

Figure 12:
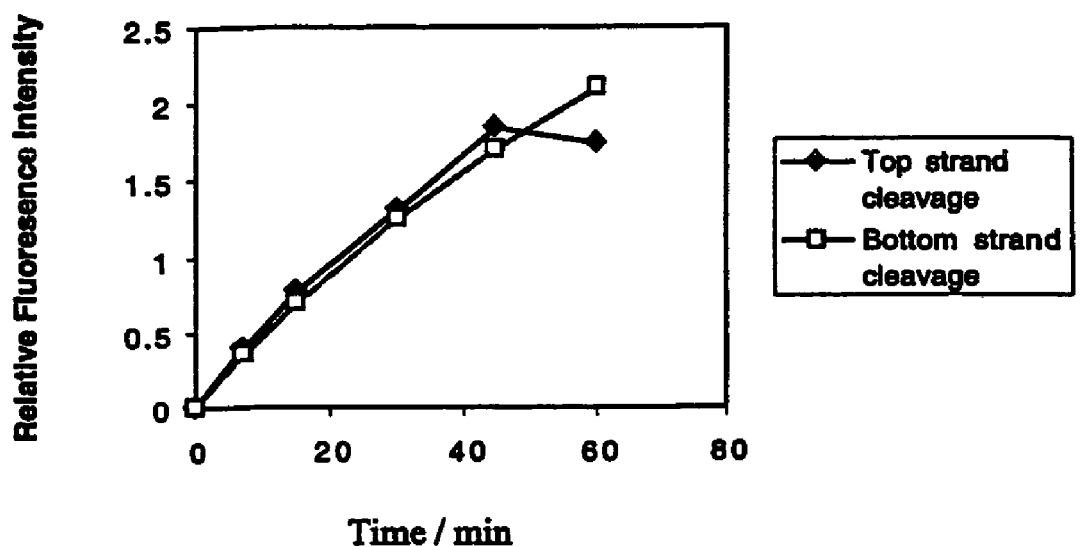
FIG. 12 is a plot of relative intensity v. time which relates the activity of the Tma endo V cleavage reaction with respect to time.

Using the new optimal reaction conditions, a time course of the Tma endo V cleavage reaction was performed at 65° C. using PCR fragments containing the K-ras G12D(G→A) mutation (FIG. 12). In these experiments, a mixture of wild-type and G12D mutant DNA PCR amplified fragments were used. The two resultant heteroduplexed fragments contain G-T and A-C mismatches, respectively. Cleavage of both top and bottom strand were observed, products were separated on an ABI 377 DNA sequencing apparatus, and the amount of cleavage product was quantified using GeneScan 3.0 analysis software. The products increased linearly over the hour time course. Longer incubations can lead to an undesirable increase of nonspecific products. Therefore, the optimal reaction conditions for Tma endo V using heteroduplex PCR fragments as the substrate, in a reaction buffer containing 10 mM HEPES (pH 7.4), 5 mM $MgCl_2$, 1 mM DTT, 2% glycerol, approx. 1–1.5 M betaine, and 5% DMSO, and an incubation at 65° C. for 1 h.

Figure 13:
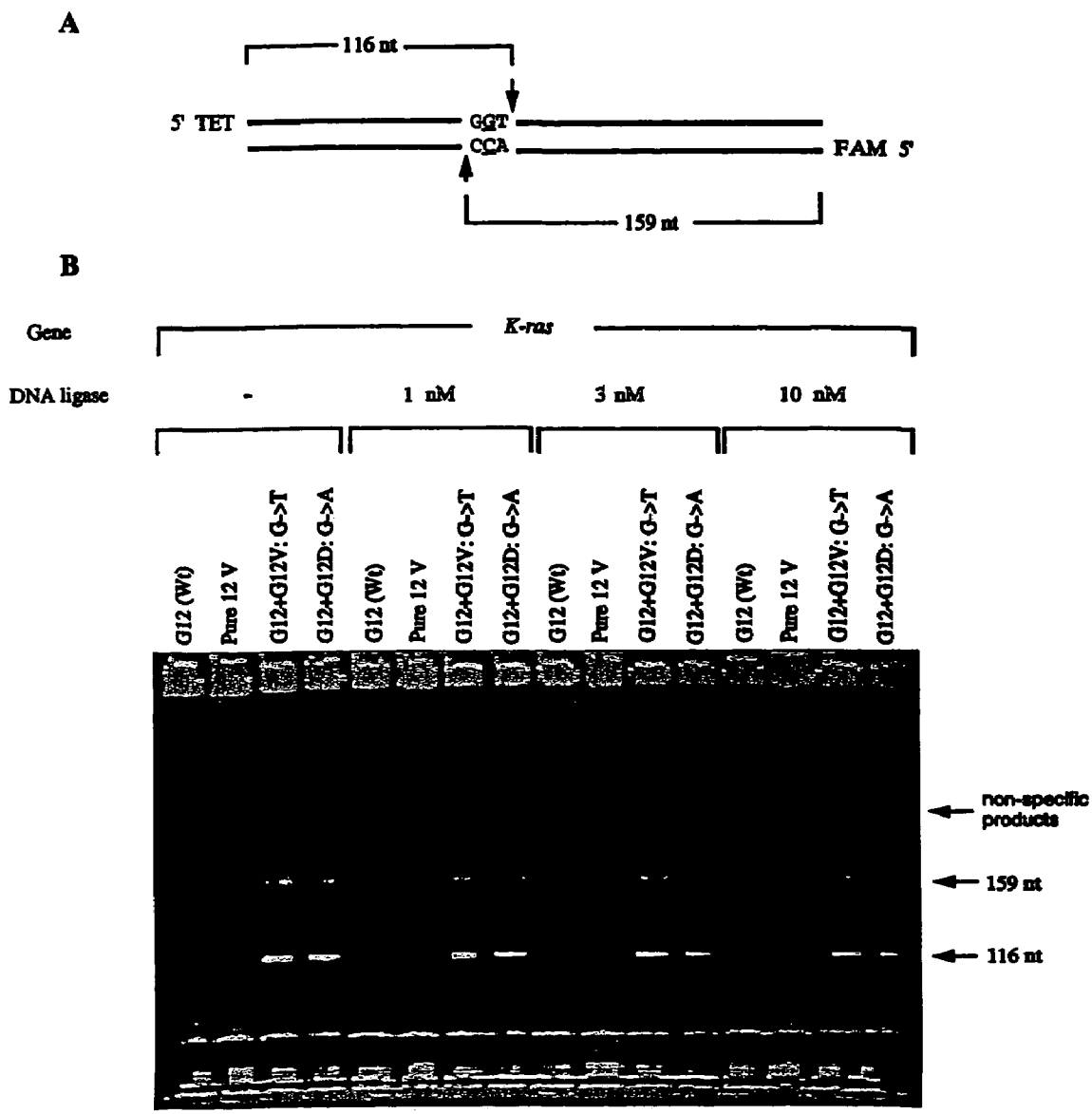
FIG. 13A is a schematic diagram of the K-ras Exon 1 amplicon showing primer labeling and predicted size of cleavage products.
FIG. 13B demonstrates the ability of the present invention to detect point mutations in the K-ras gene, and subsequent incubation with different amounts of DNA ligase allows for sealing of non-specific cleavage products, while still retaining the correct, specific cleavage products.

FIG. 13 (-DNA Ligase Lanes) demonstrates that the new optimal reaction conditions result in high activity and relatively good specificity of the Tma endo V enzyme when PCR fragments are used as substrates. Nevertheless, non-specifc nicking is still observed, and as a result there exists significant background signal.

Example 14

Ligation Reaction Condition with $NAD^+$ DNA Ligase

The optimal reaction buffer for Tsp.AK16D ligase is 20 mM Tris-HCl pH 8.5, 5 mM $MgCl_2$, 50 mM KCl, 10 mM DTT, 1 mM $NAD^+$, 20 μg/ml BSA. Tong, J., et al., "Biochemical Properties of a High Fidelity DNA Ligase from *Thermus* Species AK16D," *Nucleic Acids Res.*, 27:788–94 (1999), which is hereby incorporated by reference. Fifteen μL of the reaction mixture from the Endo V cleavage were added to 2 μl of 10× supplemental buffer (200 mM Tris-HCl, pH 8.5, 12.5 mM $MgCl_2$, 500 mM KCl, 100 mM DTT and 200 μg/ml BSA), 1 μl of 20 mM $NAD^+$, and 2 μl of 10–60 nM Tsp. AK16D DNA ligase. The final concentration of the mixture is: 20 mM Tris-HCl pH 8.5, 5 mM $MgCl_2$, 50 mM KCl, 10 mM DTT, 1 mM $NAD^+$, 20 μg/ml BSA and 1–6 nM AK16D DNA ligase. The mixture was incubated at 65° C. for 20 min and terminated by adding an equal volume of GeneScan stop solution (50 mM EDTA, 1% blue dextran and 80% formamide). The reaction mixtures were then heated at 94° C. for 2 min. and cooled on ice. 2–3 μl of the mixture were loaded onto a 6% denaturing polyacrylamide gel and electrophoresed for 1 hr in an ABI 377 sequencer (Perkin Elmer) under the following conditions: voltage of 1000 volts, current of 60 mA, power of 200 w, and gel temperature of 45° C. 6-FAM and TET were the fluorescent group labelled in top and bottom strand primers, respectively. They appear blue and green, respectively, with an ABI DNA sequencer 377. Therefore, it can be concluded that the TET labeled (green) cleavage bands were generated from the top strand and FAM labeled (blue) cleavage bands were from the bottom strand. Since TAMRA labeled GeneScan Molecular size standard 500 (red bands) was loaded on the same gel, the molecular weight of cleavage products could be estimated by comparison of the mobility of the size standards to the cleavage products using the GeneScan analysis software versions 2.1 or 3.0a.

Example 15

Detection of Codon 12 and 13 Mutations in K-ras Gene

The strategy of mutation scanning with Tma endo V/AK16D DNA ligase was first tested in the detection of codon 12 and 13 mutations in the K-ras gene. Genomic DNA from cell lines containing mutations in codon 12 and 13 were used as templates for PCR amplification. The cell lines containing K-ras mutation are listed in Table 3 as follows:

TABLE 3

| Cell Line | Genotype | Ratio of mutant-to-wild type |
|---|---|---|
| HT29 | Wild type | |
| SW1417 | | |
| SW1116 | G12A (G→C) | 0.7:1 |
| DLD 1 | G13D (G→A) | 1:1 |
| HCT 15 | | |
| LS180 | G12D (G→A) | 1.8:1 |
| SW620 | Pure G12V (G→T) | |
| Sw480 | | |

The sequence of top strand PCR primer was:
Tet-5'-CCCCATAGTGTATTAACCTTATGTGTGACATGTTC-3' (SEQ. ID. No. 33), and for the bottom strand primer was Fam 5'-CCCCAAAATGGT-CAGAGAAACCTTTATCTGTATC-3' (SEQ. ID. No. 34).

The PCR reaction was performed at 94° C. for 2 min, followed by the addition of AmpliTaq DNA polymerase, and, then, 30 cycles of 94° C. for 15 sec, 60° C. for 2 min. A final extension was then performed at 72° C. for 7 min. A wild-type PCR fragment from genomic DNA was then mixed with the mutant PCR fragment in a ratio of 1:1. In order to remove Taq DNA polymerase, 1 μl of proteinase K was added (20 mg/ml, QIAGEN) for every 12 μl of PCR products. This reaction was incubated at 70° C. for 10 min and at 80° C. for 10 min to inactivate the Proteinase K. Heteroduplex fragments were then formed by heating the mixture at 94° C. for 1 min, 65° C. for 15 min, and then cooling down to room temperature. The PCR fragments generated from the genomic DNA of cell line SW1116 did not require the addition of wild type PCR fragements.

For the cleavage reaction, the standard reaction mixture consisted of 10 mM HEPES (pH 7.4), 1 mM DTT, 2% glycerol, 5 mM $MgCl_2$, 5% DMSO, 1.5 M betaine, 100 ng PCR products, 500 nM, and purified Tma endonuclease V protein. The reaction mixture was incubated at 65° C. for 1 hour and was terminated by adding 15 μl of reaction mixture to 2 μL of 10× ligase supplemental buffer (200 mM Tris-HCl, pH 8.5, 12.5 mM $MgCl_2$, 500 mM KCl, 100 mM DTT, and 200 μg/ml BSA). The KCl of the 10× ligase supplemental buffer is responsible for the inhibition of Tma endo V cleavage activity. Next, 1 μl of 20 mM $NAD^+$, and 2 μl of 60 nM AK16D DNA ligase was added to bring the final concentration of the ligase reaction mixture to 20 mM Tris-HCl pH 7.6, 5 mM $MgCl_2$, 50 mM KCl, 10 mM DTT, 1 mM $NAD^+$, 20 μg/ml BSA, and 6 nM AK16D DNA ligase. The mixture was incubated at 65° C. for 20 min and terminated by adding an equal volume of GeneScan stop solution (50 mM EDTA, 1% blue dextran, and 80% formamide). The reaction mixture was then heated at 94° C. for 2 min. and cooled on ice. 3 μl of the mixture were loaded onto a 6% denaturing polyacrylamide gel and electrophoresed for 1 hr on an ABI 377 sequencer (Perkin Elmer) at 1000 volts, 60 mA, 200 W, and a gel temperature of 45° C.

After endo V cleavage, none of the major cleavage bands were found in the pure wild type and pure mutant G12V. Two major cleavage bands were found in the sample of G12+G12V and G12+G12D (LS180). The length of the FAM labeled (blue band; top strand cleavage product) is about 157–160 bp which is in the range of the expected length of 159 bp for a mismatch cleavage. The length of TET labeled (green band; bottom strand cleavage product) is around 118 bp which is also close to the expected value of 116 bp for a mismatch cleavage. In addition to the G12V mutation, mutations G12D and G12A were also detected in similar assays. In the G12D assay, both top and bottom strand cleavage products were observed, and their intensities were only a little less than that of G12V. In the detection of G12A, the cleavage of both strands was again observed. The intensity of the top strand product was almost the same as that of G12D, but the intensity of the bottom strand product was much lower than those of the other two mutants. The mutation G13D was not detected.

FIG. 13 demonstrates how the addition of the ligation step dramatically decreases background due to non specific nicking. For this assay, PCR fragments were generated from DNA samples that were homozygous for either the wt or mutation at position G12 in kras, or heterozygous at this position. Without the ligation step, nonspecific cleavage is observed in all the samples. But with the addition of the Tsp. AK16D ligase step, this background signal is dramatically reduced. Only in heterozygous samples (i.e. the last two lanes of each set) does one observe cleavage associated with a heteroduplex mismatch, and these results demonstrate that the additional ligation step does not compromise specific mismatch cleavage. Therefore, the additional ligation step is able to reduce background due to cleavage at non-mismatch positions but does not ligate cleavages at mismatch cleavage sites.

In addition to the major mismatch cleavage products, some non-specific cleavage bands were also observed. There is one non-specific band in all samples which migrates above the blue (i.e. top strand) cleavage products present. There are also two non-specific cleavage products, one is blue and the other is green, which migrate with low molecular weight products and are present in all four samples. After incubation with 1–6 nM DNA ligase, the non-specific band above the blue cleavage band decreases in intensity, indicating the non-specific nick was sealed by the DNA ligase. The low molecular weight non-specific bands are still present even when the concentration of AK16D ligase was raised to 6 nM (See FIG. 13). This suggests that these may be non-ligatable degradation products or, alternatively, short fragments which have denatured from the substrate during the 1 hour Endo V incubation at 65° C. in organic solvents.

Figure 14:
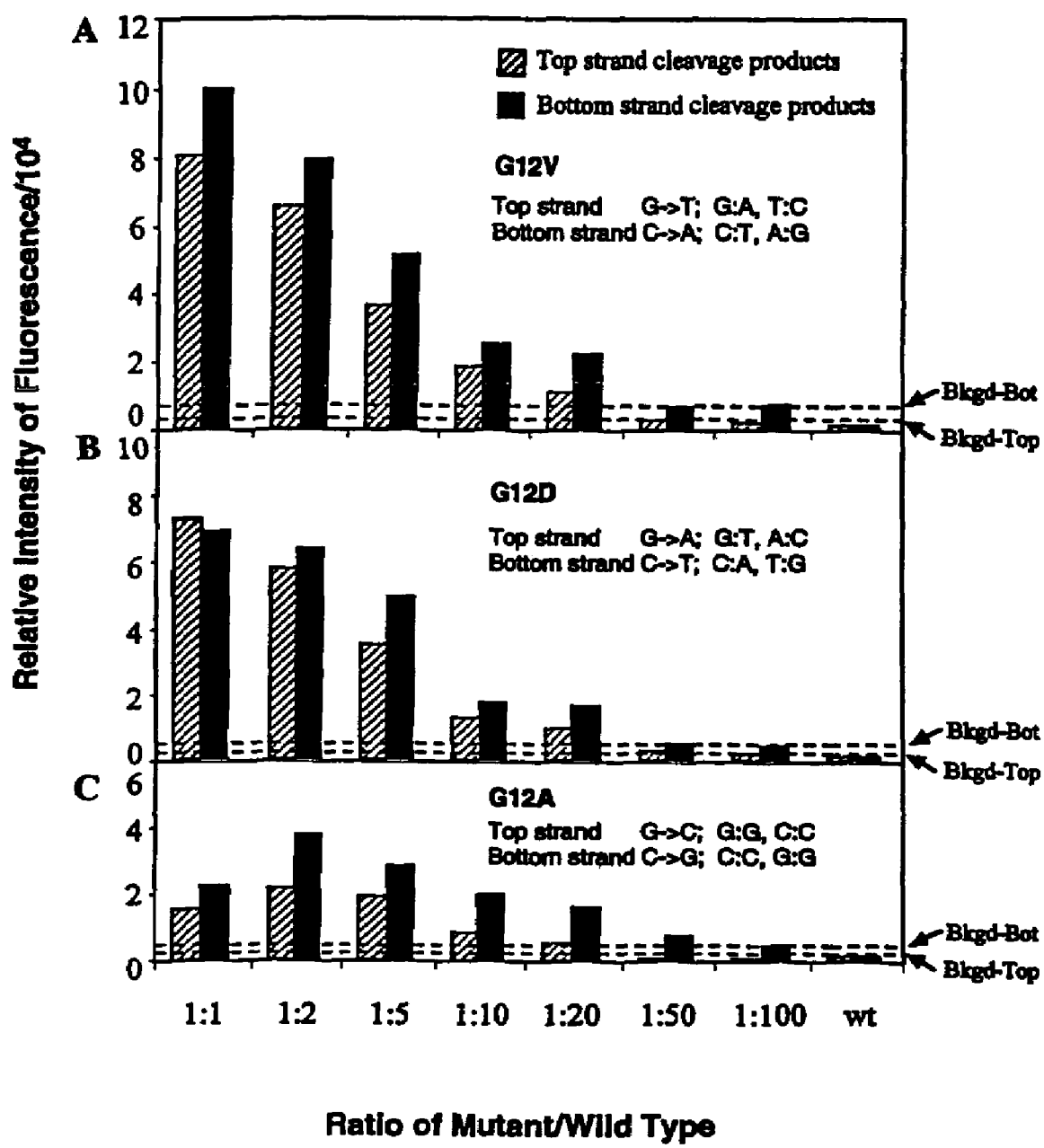
FIGS. 14A–C are plots of relative intensity of fluorescence v. ratio of mutant/wild type, demonstrating the sensitivity of the present invention.

In order to characterize the sensitivity of this invention, base-mismatches in PCR fragments containing K-ras exon 1 mutations were assayed under varying ratios of mutant-to-wild type DNA. With this invention the efficiency of cleavage for a 1:1 mutant-to-wild type DNA ratio for DNA containing K-ras mutations, G12V, G12D and G12A is typically high, medium, and low, respectively. Utilizing this set of mutations allows one to screen for sensitivity over a wide range of cleavage efficiencies and should more accurately reflect the useful range of this invention. PCR fragments containing K-ras exon1 mutations, G12V, G12D, and G12A were separately mixed with wild type PCR fragments in mutant-to-wild type ratios of 1:1, 1:2, 1:5, 1:10, 1:20, 1:50, and 1:100. These fragment mixtures were then assayed using the above mentioned Tma Endo V and DNA ligase conditions. FIG. 14 shows the amount of cleavage products for the different ratio of mutant-to-wild type DNA. The results indicate that cleavage signals can be distinguished from background for mutant-to-wild type ratios of up to 1:20 for all three mutantions. For ratios greater than 1:20, the signal at the correct position was still observed; however, it is difficult to conclusively distinguish between cleavage products and background. From this assay, it appears that the limit of sensitivity for the present invention is approximately 1:20 (mutant-to-wild type ratio).

Example 16

Detection of Various Point Mutations in p53 and VHL Genes

To study the versatility of endo V to scan different point mutations, the technique of the present invention was applied to genomic DNA with various point mutations in p53 and VHL genes. Eleven samples containing point mutations in exon 5, 6, 7, and 8 in p53 and 13 samples containing point mutations in VHL were obtained. The sequence of PCR primers for amplifying exons in p53 and VHL genes are listed in Table 2A. PCR thermocycle conditions are listed in Table 2B. From the gel image of the 500 bp VHL exon 1 fragment, a smear was observed, extending from about 180 to 500 bp. This makes it very hard to observe the cleavage products in this region due to the very high GC content in the middle of exon 1 of VHL. As a result, interactions between PCR fragments and other regions of the genomic DNA may occur. If so, the template should be diluted in the second round of PCR amplification to reduce the smear. Therefore, for the second round of PCR amplification, only 1 μL of a 100 fold dilution of the PCR products was used and amplified under the same cycling conditions as discussed previously, but this time for only 15 rounds. The smear was dramatically reduced, and the products were then visible.

Genomic DNA containing p53 mutations was extracted from tumor samples and PCR amplified. Subsequently, wild-type PCR fragments were added so that equal amounts of mutant and wild type PCR fragments were present. Genomic DNA containing the VHL gene mutation was from heterozygous samples, so wild type PCR fragments were not added. In order to remove Taq DNA polymerase, 1 μl of proteinase K was added (20 mg/ml, QIAGEN) for every 12 μl of PCR products. This reaction was incubated at 70° C. for 10 min and at 80° C. for 10 min to inactivate the Proteinase K. Heteroduplexed fragments were then formed by heating the mixture at 94° C. for 1 min, 65° C. for 15 min, and then cooling down to room temperature.

For the cleavage reaction, the standard reaction mixture consisted of 10 mM HEPES (pH 7.4), 1 mM DTT, 2% glycerol, 5 mM MgCl$_2$, 5% DMSO, 1.5 M betaine, 100 ng PCR products, 500 nM, and purified Tma endonuclease V protein. The reaction mixture was incubated at 65° C. for 1 hour and was terminated by adding 15 μl of reaction mixture to 2 μL of 10× ligase supplemental buffer (200 mM Tris-HCl, pH 8.5, 12.5 mM MgCl$_2$, 500 mM KCl, 100 mM DTT and 200 μg/ml BSA). Next, 1 μl of 20 mM NAD$^+$ and 2 μl of 60 nM AK16D DNA ligase were added to bring the final concentration of the ligase reaction mixture to 20 mM Tris-HCl pH 7.6, 5 mM MgCl$_2$, 50 mM KCl, 10 mM DTT, 1 mM NAD$^+$, 20 μg/ml BSA, and 6 nM AK16D DNA ligase. The mixture was incubated at 65° C. for 20 min and terminated by adding an equal volume of GeneScan stop solution (50 mM EDTA, 1% blue dextran, and 80% formamide). The reaction mixture was then heated at 94° C. for 2 min. and cooled on ice. Three μl of the mixture were loaded onto a 6% denaturing polyacrylamide gel and electrophoresed for 1 hr on an ABI 377 sequencer (Perkin Elmer) at 1000 volts, 60 mA, 200 W, and a gel temperature of 45° C.

A summary of the mutation scanning results by this method are provided in Table 4.

TABLE 4

Summary of Tma EndoV/Ligase mutation scanning on cancer genes.

| Gene | Exon | Mutation | Surrounding sequences | Change | Cleavage Top Strand | Cleavage Bottom Strand |
|---|---|---|---|---|---|---|
| K-ras | Exon 1 | G12V | TG<u>G</u>TG | G→T | +++ | ++ |
| | | G12D | TG<u>G</u>TG | G→A | ++ | ++ |
| | | G12A | TG<u>G</u>TG | G→C | ++ | + |
| | | G13D | TGG<u>C</u>G | G→A | − | − |
| APC | Exon 15 | I1307K | AA<u>T</u>AA | T→A | + | ++ |
| p53 | Exon 5 | C135Y | TT<u>G</u>CC | G→A | ++ | − |
| | | R175H | GC<u>G</u>CT | G→A | − | − |
| | Exon 6 | R196C | TC<u>C</u>GA | C→T | − | ++ |
| | | Y220C | CT<u>A</u>TG | A→G | ++ | − |
| | Exon 7 | S241F | TT<u>C</u>CT | C→T | + | + |
| | | G245S | GC<u>G</u>GC | G→A | +++ | − |
| | | R248Q | CC<u>G</u>GA | G→A | +++ | − |
| | | R248W | AC<u>C</u>GG | C→T | − | ++ |
| | Exon 8 | R273H | GC<u>G</u>TG | G→A | + | + |
| | | R273C | TG<u>C</u>GT | C→T | − | − |
| | | R282W | AC<u>C</u>GG | C→T | ++ | ++ |
| BRCA 1 | Exon 2 | 185 del.AG | TT<u>AG</u>AG | AG deletion | +++ | +++ |
| | Exon 20 | 5382 Ins.C | AT<u>C</u>CC | C insertion | + | − |
| BRCA 2 | Exon 11 | 6174del.T | AG<u>T</u>GG | T deletion | + | − |
| VHL | Exon 1 | P157L | GC<u>C</u>CG | C→T | − | ++ |
| | | W159A | TA<u>T</u>GG | T→A | +++ | ++ |
| | | G164D | CG<u>G</u>CG | G→A | − | − |
| | | Y169H | CC<u>T</u>AC | T→C | − | + |
| | | Y183H | GC<u>T</u>AC | T→C | ++ | ++ |
| | Exon 2 | F190L | TT<u>C</u>AG | C→G | − | ++ |
| | | G198 G | GG<u>G</u>CT | G→T | ++ | +++ |
| | | L199F | GG<u>C</u>TT | C→T | − | +++ |
| | | S200 Ins. E | CT<u>AG</u>AGG | AGA insertion | +++ | +++ |
| | | A220T | TT<u>G</u>CC | G→A | +++ | − |
| | | N221 del. A | CC<u>A</u>AT | A deletion | +++ | +++ |

TABLE 4-continued

Summary of Tma EndoV/Ligase mutation scanning on cancer genes.

| Gene | Exon | Mutation | Surrounding sequences | Change | Cleavage Top Strand | Bottom Strand |
|------|------|----------|----------------------|--------|--------------------|--------------| 
|      | Exon 3 | L229P | TCTGA | T→C | − | + |
|      |        | R232Q | GCGAT | G→A | + | ++ |
|      |        | R238W | TCCGG | C→T | − | ++ |
|      |        | L259Q | TCTGG | T→A | +++ | ++ |

*: +++: high intensity cleavage. ++; intermediate intensity cleavage. +: low intensity cleavage −: no cleavage observed.

For the p53 gene, 9 out of the 11 mutations were detected. For the VHL gene, 12 out of 13 point mutations were detected. For all of the point mutations not detected, DNA sequencing was performed to PCR fragments of these samples in order to verify the presence of the mutation and the ratio of mutant to wild type DNA. The results showed that the mutations were present in these samples and the ratio of mutant to wild type DNA was approximately 1:1 in all of the samples, except for sample R175H. After adding wild-type PCR fragments to the mutant PCR fragments containing R175H, cleavage assays were repeated, but the results for R175H were still negative.

All but four mutations listed in Table 4 could be recognized by Tma endonuclease V. The four non-detectable mutations are K-ras G13D(G→A), p53 R175H(G→A), R273C(C→T), and VHL G164D(G→A) (Table 4), and the surrounding sequence of each mutation for both top and bottom strand are listed in Table 5.

TABLE 5

List of Mutations and surrounding sequences for top and bottom strand, with cleavage intensity.

| Gene | Exon | Mutation | Surrounding Sequences (Wt) | Surrounding Sequences (Mt) | Changes | Mismatches | |
|------|------|----------|---------------------------|----------------------------|---------|------------|---|
| Purine (G or A) containing strand | | | | | | | |
| VHL | Exon 2 | L199F | AAGCC | AAACC | G→A | G:T, A:C | +++ |
| VHL | Exon 3 | R232Q | GCGAT | GCAAT | G→A | G:T, A:C | + |
| P53 | Exon 5 | R175H | GCGCT | GCACT | G→A | G:T, A:C | − |
| P53 | Exon 8 | R273C | ACGCA | ACACA | G→A | G:T, A:C | − |
| P53 | Exon 7 | G245S | GCGGC | GCAGC | G→A | G:T, A:C | +++ |
| P53 | Exon 7 | R248Q | CCGGA | CCAGA | G→A | G:T, A:C | +++ |
| VHL | Exon 3 | R238W | CCGGA | CCAGA | G→A | G:T, A:C | ++ |
| P53 | Exon 7 | R248W | CCGGT | CCAGT | G→A | G:T, A:C | ++ |
| P53 | Exon 8 | R282W | CCGGT | CCAGT | G→A | G:T, A:C | ++ |
| VHL | Exon 3 | L229P | TCAGA | TCGGA | A→G | A:C, G:T | + |
| P53 | Exon 6 | R196C | TCGGA | TCAGA | G→A | G:T, A:C | ++ |
| P53 | Exon 8 | R273H | GCGTG | GCATG | G→A | G:T, A:C | + |
| P53 | Exon 7 | S241F | AGGAA | AGAAA | G→A | G:T, A:C | + |
| VHL | Exon 1 | G164D | CGGCG | CGACG | G→A | G:T, A:C | − |
| K-ras | Exon 1 | G13D | TGGCG | TGACG | G→A | G:T, A:C | − |
| VHL | Exon 1 | P157L | CGGGC | CGAGC | G→A | G:T, A:C | ++ |
| K-ras | Exon 1 | G12D | TGGTG | TGATG | G→A | G:T, A:C | ++ |
| VHL | Exon 2 | A220T | TTGCC | TTACC | G→A | G:T, A:C | +++ |
| P53 | Exon 5 | C135Y | TTGCC | TTACC | G→A | G:T, A:C | ++ |
| VHL | Exon 1 | Y169H | GTAGG | GTGGG | A→G | A:C, G:T | + |
| VHL | Exon 1 | Y183H | GTAGC | GTGGC | A→G | A:C, G:T | ++ |
| P53 | Exon 6 | Y220C | CTATG | CTGTG | A→G | A:C, G:T | ++ |
| VHL | Exon 2 | F190L | CTGAA | CTCAA | G→C | G:G, C:C | ++ |
| K-ras | Exon 1 | G12A | TGGTG | TGCTG | G→C | G:G, C:C | ++ |
| K-ras | Exon 1 | G12V | TGGTG | TGTTG | G→T | G:A, T:C | +++ |
| VHL | Exon 2 | G198G | GGGCT | GGTCT | G→T | G:A, T:C | ++ |
| VHL | Exon 1 | W159A | CCATA | CCTTA | A→T | A:A, T:T | ++ |
| VHL | Exon 3 | L259Q | CCAGA | CCTGA | A→T | A:A, T:T | ++ |
| APC | Exon 15 | I1307K | TTATT | TTTTT | A→T | A:A, T:T | ++ |
| P53 | Exon 6 | Y220C | CATAG | CACAG | T→C | T:G, C:A | − |
| K-ras | Exon 1 | G12D | CACCA | CATCA | C→T | C:A, T:G | ++ |
| P53 | Exon 8 | R273H | CACGC | CATGC | C→T | C:A, T:G | + |
| VHL | Exon 1 | Y169H | CCTAC | CCCAC | T→C | T:G, C:A | − |
| VHL | Exon 1 | Y183H | GCTAC | GCCAC | T→C | T:G, C:A | ++ |
| VHL | Exon 1 | P157L | GCCCG | GCTCG | C→T | C:A, T:G | − |
| P53 | Exon 7 | G245S | GCCGC | GCTGC | C→T | C:A, T:G | − |
| VHL | Exon 3 | L229P | TCTGA | TCCGA | T→C | T:G, C:A | − |
| P53 | Exon 6 | R196C | TCCGA | TCTGA | C→T | C:A, T:G | − |
| P53 | Exon 7 | R248Q | TCCGG | TCTGG | C→T | C:A, T:G | − |

TABLE 5-continued

List of Mutations and surrounding sequences for top and bottom strand, with cleavage intensity.

| Gene | Exon | Mutation | Surrounding Sequences (Wt) | Surrounding Sequences (Mt) | Changes | Mismatches | |
|---|---|---|---|---|---|---|---|
| VHL | Exon 3 | P238W | TCCGG | TCTGG | C→T | C:A, T:G | − |
| P53 | Exon 7 | P248W | ACCGG | ACTGG | C→T | C:A, T:G | − |
| P53 | Exon 8 | P282W | ACCGG | AGTGG | C→T | C:A, T:G | ++ |
| VHL | Exon 2 | A220T | GGCAA | GGTAA | C→T | C:A, T:G | − |
| P53 | Exon 5 | C135Y | GGCAA | GGTAA | C→T | C:A, T:G | − |
| K-ras | Exon 1 | G13D | CGCCA | CGCCA | C→T | C:A, T:G | − |
| VHL | Exon 1 | G164D | CGCCG | CGTCG | C→T | C:A, T:G | − |
| VHL | Exon 2 | L199F | GGCTT | GGTTT | C→T | C:A, T:G | − |
| P53 | Exon 5 | R175H | AGCGC | AGTGC | C→T | C:A, T:G | − |
| P53 | Exon 8 | R273C | TGCGT | TGTGT | C→T | C:A, T:G | − |
| P53 | Exon 7 | S241F | TTCCT | TTTCT | C→T | C:A, T:G | + |
| VHL | Exon 3 | R232Q | ATCGC | ATTGC | C→T | C:A, T:G | ++ |
| VHL | Exon 2 | F190L | TTCAG | TTGAG | C→G | C:C, G:G | − |
| K-ras | Exon 1 | G12A | CACCA | CAGCA | C→G | C:C, G:G | + |
| K-ras | Exon 1 | G12V | CACCA | CAACA | C→A | C:T, A:G | ++ |
| VHL | Exon 2 | G198G | AGCCC | AGACC | C→A | C:T, A:G | +++ |
| VHL | Exon 1 | W159A | TATGG | TAAGG | T→A | T:T, A:A | +++ |
| VHL | Exon 3 | L259Q | TCTGG | TCAGG | T→A | T:T, A:A | +++ |
| APC | Exon 15 | I1307K | AATAA | AAAAA | T→A | T:T, A:A | + |

Purine (G or A) containing strand

| VHL | Exon 2 | F190L | CTGAA | CTCAA | G→C | G:G, C:C | ++ |
| VHL | Exon 2 | F190L | TTGAG | TTCAG | G→C | G:G, C:C | − |
| K-ras | Exon 1 | G12A | TGGTG | TGCTG | G→C | G:G, C:C | ++ |
| K-ras | Exon 1 | G12A | CAGCA | CACCA | G→C | G:G, C:C | + |
| K-ras | Exon 1 | G12V | TGGTG | TGTTG | G→T | G:A, T:C | +++ |
| VHL | Exon 2 | G198G | GGGCT | GGTCT | G→T | G:A, T:C | ++ |
| VHL | Exon 2 | G198G | AGACC | AGCCC | A→C | A:G, C:T | +++ |
| K-ras | Exon 1 | G12V | CAACA | CACCA | A→C | A:G, C:T | ++ |
| APC | Exon 15 | I1307K | AAAAA | AATAA | A→T | A:A, T:T | + |
| VHL | Exon 1 | W159A | TAAGG | TATGG | A→T | A:A, T:T | +++ |
| VHL | Exon 3 | L259Q | TCAGG | TCTGG | A→T | A:A, T:T | +++ |
| VHL | Exon 3 | L259Q | CCAGA | CCTGA | A→T | A:A, T:T | ++ |
| VHL | Exon 1 | W159A | CCATA | CCTTA | A→T | A:A, T:T | ++ |
| APC | Exon 15 | I1307K | TTATT | TTTTT | A→ | A:A, T:T | ++ |

Previous assays with double-stranded oligonucleotide substrates demonstrated that every point mutations can be detected with this method (FIGS. 3 and 5, Table 4), with mismatches containing cytosine to be the least efficiently cleaved. Even though all four of these mutations generate heteroduplex PCR fragments with cytosine mismatches, so do the vast majority of the mutations surveyed. Therefore, the presence of a cytosine mismatch is not sufficient to explain why these four mutations were not detected. Instead, the data suggests that flanking sequences need to be taken into account. Analysis of the surrounding sequences of the four mutations which could not be cleaved by Tma Endo V gives the following consensus sequences: gRcg, rcRc, cgYc, and gYgy. The position of the mutation or polymorphism is underlined and shown in upper case, the last two sequences listed are the complements of the first two sequences (where R and Y stand for a purine and pyrimidine base, respectively). In a very preliminary analysis, the 1$^{st}$ 100 random single nucleotide polymorphisms (SNPs) from human chromosome 22 were searched for the four refractory sequences, and only one, rcRc, was found (Table 6).

TABLE 6

The frequency of Tma EndoV refractory sequences in Human Chromosome 22, 1$^{st}$ 100 random SNPs.

| EndoV Refractory Sites | | | | CG dinucleotides | | Transitions | | Transversions | |
|---|---|---|---|---|---|---|---|---|---|
| gRcg | rcRc | cgYc | gYgy | cR | Yg | R | Y | W,S | M,K |
|  | acRca |  |  | gcRga | aaYgg | agRgg | ttYat | caSaa | ggMcc |
|  |  |  |  | acRaa | acYgt | agRtg | tcYtc | aaWta | ccMaa |
|  |  |  |  | ccRgc | agYga | tgRaa | gcYtc | aaWaa | caKcg |
|  |  |  |  | gcRat | ggYgg | ctRat | taYct | aaSta | gtKcc |
|  |  |  |  | ccRtg | aaYgc | agRga | caYaa | taStt | acMat |
|  |  |  |  | tcRaa | agYga | agRgg | atYtt | taSct | atMaa |
|  |  |  |  | tcRtg | tcYgg | taRtc | tgYag | tgWga | tgKgt |
|  |  |  |  | acRtg | gcYtc | gtRtg | aaYat | ttStt | aaMtt |
|  |  |  |  |  | caYgt | aaRtt | caYtg | aaSgt | ttMac |

TABLE 6-continued

The frequency of Tma EndoV refractory sequences in Human Chromosome 22, 1st 100 random SNPs.

| EndoV Refractory Sites | | CG dinucleotides | | Transitions | | Transversions | |
|---|---|---|---|---|---|---|---|
| | | acYgt | agRgc | taYca | caSag | gaKgg | |
| | | aaYgc | aaRag | taYaa | caSat | acMgt | |
| | | gtYgg | gaRgc | caYtg | acSgt | taMcg | |
| | | ttYgt | ggRgg | tcYac | tcScg | ttKcc | |
| | | ccYgc | atRca | ttYag | agWta | ggMac | |
| | | caYgt | | gcYtc | gtWca | ctKta | |
| | | ctYgg | | ccYat | aaWct | agMgg | |
| | | ggYga | | ctYtg | ccSgt | agMga | |
| | | caYgt | | aaYtt | ttWga | agMgg | |
| | | | | ccYca | ccSgt | | |
| | | | | tgYtg | gtStg | | |
| | | | | | acWtg | | |
| Total is: | | | | | | | |
| 0 | 1 | 0 | 0 | 8 | 18 | 14 | 20 | 21 | 18 |

Subsequent computer searches of some 4,000 SNPs in the SNP database revealed the frequency of the gRcg (and complement cgYc) was about 0.1% and the rcRc (and complement gYgy) was about 2%. This preliminary result suggests that the frequency of the four refractory sequences is very low (2%), and it is possible that Tma endo V can cleave approximately 98% of the poymorphisms and mutations found in the human genome.

In addition to detecting single base mutations, the analysis demonstrates that the present invention is also capable of detecting small insertions and deletions (See Table 4). A three base insertion in the VHL gene and a two base deletion in BRCA 1 both resulted in very strong cleavage signals for both strands. A single base deletion in the VHL gene also resulted in a strong signal for both strands. The worst results were obtained with a single insertion and a single base deletion in the BRCA 1 gene. Both for the insertion and deletion only one strand was observed to be cleaved, and the signal was relatively weak for both cases. Despite this lower efficiency, this type of signal is capable of confirming a variation in an unknown sample. These results demonstrate that the present invention can detect small insertions and deletions, and, similar to mutation detection, the efficiency is sequence dependent.

Example 17

Detection of T→A Mutation in Codon 1307 of Exon 15 in the APC Gene

The method of the present invention was applied to clinical samples by scanning T→A mutation in codon 1307 in exon 15 of APC gene. Nine genomic samples from colon cancer tissues and four wild type samples were assayed.

The sequence of the top strand PCR primer was

Tet-5'-CCCCGCTGCCACTTGCAAAGTTTCTTC-3' (SEQ. ID. No. 35)

while the sequence of the bottom strand PCR primers was

Fan-5'-CCCCACTCTGAACGGAGCTGGCAAT-3' (SEQ. ID. No. 36)

The PCR reaction condition was listed in Table 2B. Since genomic DNA containing APC mutations were heterozygous, it is not necessary to add wild-type PCR fragments. In order to remove Taq DNA polymerase, 1 µl of proteinase K was added (20 mg/ml, QIAGEN) for every 12 µl of PCR products. This reaction was incubated at 70° C. for 10 min and at 80° C. for 10 min to inactivate the Proteinase K. Heteroduplex fragments were then formed by heating the mixture at 94° C. for 1 min, 65° C. for 15 min, and then cooling down to room temperature. The PCR fragments from genomic DNA of cell line SW1116 were directly heated and cooled down to produce heteroduplexes without adding wild type PCR fragments.

For the cleavage reaction, the standard reaction mixture consisted of 10 mM HEPES (pH 7.4), 1 mM DTT, 2% glycerol, 5 mM $MgCl_2$, 5% DMSO, 1.0 M betaine, 100 ng PCR products, 500 nM, and purified Tma endonuclease V protein. The reaction mixture was incubated at 65° C. for 1 hour and was terminated by adding 15 µl of reaction mixture to 2 µL of 10× ligase supplemental buffer (200 mM Tris-HCl, pH 8.5, 12.5 mM $MgCl_2$, 500 mM KCl, 100 mM DTT, and 200 µg/ml BSA). Next, 1 µl of 20 mM $NAD^+$ and 2 µl of 60 nM AK16D DNA ligase was added to bring the final concentration of the ligase reaction mixture to 20 mM Tris-HCl pH 7.6, 5 mM $MgCl_2$, 50 mM KCl, 10 mM DTT, 1 mM $NAD^+$, 20 µg/ml BSA, and 6 nM AK16D DNA ligase. The mixture was incubated at 65° C. for 20 min and terminated by adding an equal volume of GeneScan stop solution (50 mM EDTA, 1% blue dextran, and 80% formamide). The reaction mixture was then heated at 94° C. for 2 min. and cooled on ice. Three µl of the mixture were loaded onto a 6% denaturing polyacrylamide gel and electrophoresed for 1 hr on an ABI 377 sequencer (Perkin Elmer) at 1000 volts, 60 mA, 200 W, and a gel temperature of 45° C. The correct mutations was detected in all of the samples no false positives were detected in the wild-type or tumor samples. The cleavage activity was higher in the presence of 1.0 M betaine than that in 1.5 M betaine (FIG. 10B), presumably due to the AT rich nature of exon 15 of the APC gene. Therefore, the amount of betaine may need to be adjusted, and the GC-content of the region amplified may act as a guide.

Example 18

Detection of k-ras Mutations in the Diluted Samples

In order to determine the sensitivity of this invention, PCR fragments containing K-ras exon 1 mutations, G12V, G12D, and G12A were used as templates, and the mutation detection abilities of the present invention were assayed in different ratios of mutant-to-wild type DNA ranging from 1:1 to 1:100. The initial ratio in the G12A assay was 0.7:1, because the mutant-to-wild type ratio in the genomic DNA containing the G12A mutation was 0.7:1 and the pure mutant G12A was not available. The sequences of PCR primers are listed in Table 2A, and the PCR thermocycle conditions are listed in Table 2B. In order to remove Taq DNA polymerase, 1 µl of proteinase K was added (20 mg/ml, QIAGEN) for every 12 µl of PCR products. This reaction was incubated at 70° C. for 10 min and at 80° C. for 10 min to inactivate the Proteinase K. Heteroduplex fragments were then formed by heating the mixture at 94° C. for 1 min, 65° C. for 15 min, and then cooling down to room temperature.

The PCR fragments containing K-ras exon1 mutations, G12V, G12D, and G12A were individually mixed with wild type PCR fragments in the ratio of mutant-to-wild type of 1:1, 1:2, 1:5, 1:10, 1:20, 1:50, and 1:100. For this assay, the total amount of PCR fragments was held constant. Therefore, 100 ng of heteroduplex PCR fragments with different mutant-to-wild type ratios were cleaved with Tma endo V and ligated with Tsp. AK16D DNA ligase.

For the cleavage reaction, the standard reaction mixture consisted of 10 mM HEPES (pH 7.4), 1 mM DTT, 2% glycerol, 5 mM $MgCl_2$, 5% DMSO, 1.5 M betaine, 100 ng PCR products, 500 nM, and purified Tma endonuclease V protein. The reaction mixture was incubated at 65° C. for 1 hour and was terminated by adding 15 µl of reaction mixture to 2 µL of 10× ligase supplemental buffer (200 mM Tris-HCl, pH 8.5, 12.5 mM $MgCl_2$, 500 mM KCl, 100 mM DTT, and 200 µg/ml BSA). Next, 20 mM $NAD^+$ and 2 µl of 60 nM AK16D DNA ligase were added to bring the final concentration of the ligase reaction mixture to 20 mM Tris-HCl pH 7.6, 5 mM $MgCl_2$, 50 mM KCl, 10 mM DTT, 1 mM $NAD^+$, 20 µg/ml BSA, and 6 nM AK16D DNA ligase. The mixture was incubated at 65° C. for 20 min and terminated by adding an equal volume of GeneScan stop solution (50 mM EDTA, 1% blue dextran, and 80% formamide). The reaction mixture was then heated at 94° C. for 2 min. and cooled on ice. Three µl of the mixture were loaded onto a 6% denaturing polyacrylamide gel and electrophoresed for 1 hr on an ABI 377 sequencer (Perkin Elmer) at 1000 volts, 60 mA, 200 W, and a gel temperature of 45° C. Since a TAMRA labeled GeneScan Molecular size standard 500 was loaded on the same gel, the molecular weight of cleavage products could be estimated by comparison to the mobility of size standard using the GeneScan analysis software versions 2.1 or 3.0a.

FIG. 14 shows the amount of cleavage products for the different ratios of mutant-to-wild type DNA. The peak area was measured by the GeneScan software (v. 3.0) and was used for determining the relative fluorescence intensity. Cleavage signals generated wild type homoduplex were used as wild type controls. Background intensity was determined by measuring signal intensities directly above and below the cleavage band for both top and bottom strand products, respectively. The background signals were then averaged from seven samples with different ratios and one wild type sample. The peak area associated with the cleavage product was determined by analysis with GeneScan Analysis software 3.0. Bar graphs in FIG. 14 indicate the relative fluorescence intensity with their respective mutant-to-wild type ratios. (Striped bar: top strand cleavage products; solid bar: bottom strand cleavage products.) The average background signals are indicated with a horizontal dashed line. (Bkdg-top stands for background signals for the average top strand cleavage products, bkdg-bottom stands for the average background signals for bottom strand cleavage products.) The mutation, nucleotide change, and the mismatch base pairs are indicated inside the graph.

These results indicate that the present invention is able to consistently distinguish cleavage signals from background signals in mutant to wild-type DNA ratios of at least 1:20 for all three mutants. The present invention has been able to detect cleavage signals in mutant to wild-type DNA ratios as high as 1:50, but this has not been observed in all cases studied. Therefore, the present invention is limited to a sensitivity of 1:20 (mutant-to-wild type DNA).

Example 19

Detection of Small Deletion, Insertion in BRCA1, BRCA2, and VHL Genes

In order to determine the ability of the present invention to detect small deletion or insertions, it was applied to samples containing an AG deletion in exon 2 or a C insertion in exon 20 of BRCA 1, a T deletion in exon 11 of the BRCA 2 gene, or either an AGA insertion or an A deletion in exon 2 of von Hippel Lindau (VHL) gene.

The sequence of PCR primers for amplifying exon 2 and 20 in BRCA1, exon 11 in BRCA2 and exon 2 in VHL are listed in Table 2A, and PCR thermocycle conditions are listed in Table 2B. Since the mutations are heterozygous in the sample, it was not necessary to add wild-type PCR fragments. In order to remove Taq DNA polymerase, 1 µl of proteinase K was added (20 mg/ml, QIAGEN) for every 12 µl of PCR products. This reaction was incubated at 70° C. for 10 min and at 80° C. for 10 min to inactivate the Proteinase K. Heteroduplex fragments were then formed by heating the mixture at 94° C. for 1 min, 65° C. for 15 min, and then cooling down to room temperature.

For the cleavage reaction, the standard reaction mixture consisted of 10 mM HEPES (pH 7.4), 1 mM DTT, 2% glycerol, 5 mM $MgCl_2$, 5% DMSO, 1.5 M betaine, 100 ng PCR products, and 500 nM purified Tma endonuclease V protein. The reaction mixture was incubated at 65° C. for 1 hour and was terminated by adding 15 µl of reaction mixture to 2 µL of 10× ligase supplemental buffer (200 mM Tris-HCl, pH 8.5, 12.5 mM $MgCl_2$, 500 mM KCl, 100 mM DTT, and 200 µg/ml BSA). Next, 1 µl of 20 mM $NAD^{30}$ and 2 µl of 60 nM AK16D DNA ligase were added to bring the final concentration of the ligase reaction mixture to 20 mM Tris-HCl pH 7.6, 5 mM $MgCl_2$, 50 mM KCl, 10 mM DTT, 1 mM $NAD^{30}$, 20 µg/ml BSA and 6 nM AK16D DNA ligase. The mixture was incubated at 65° C. for 20 min and terminated by adding an equal volume of GeneScan stop solution (50 mM EDTA, 1% blue dextran and 80% formamide). The reaction mixture was then heated at 94° C. for 2 min. and cooled on ice. 3 µl of the mixture were loaded onto a 6% denaturing polyacrylamide gel and electrophoresed for 1 hr on an ABI 377 sequencer (Perkin Elmer) at 1000 volts, 60 mA, 200 W, and a gel temperature of 45° C. Because a TAMRA labeled GeneScan Molecular size standard 500 was loaded on the same gel, the molecular weight of cleavage products could be estimated by comparison to the mobility of size standard using the GeneScan analysis software versions 2.1 or 3.0a.

Figure 15:
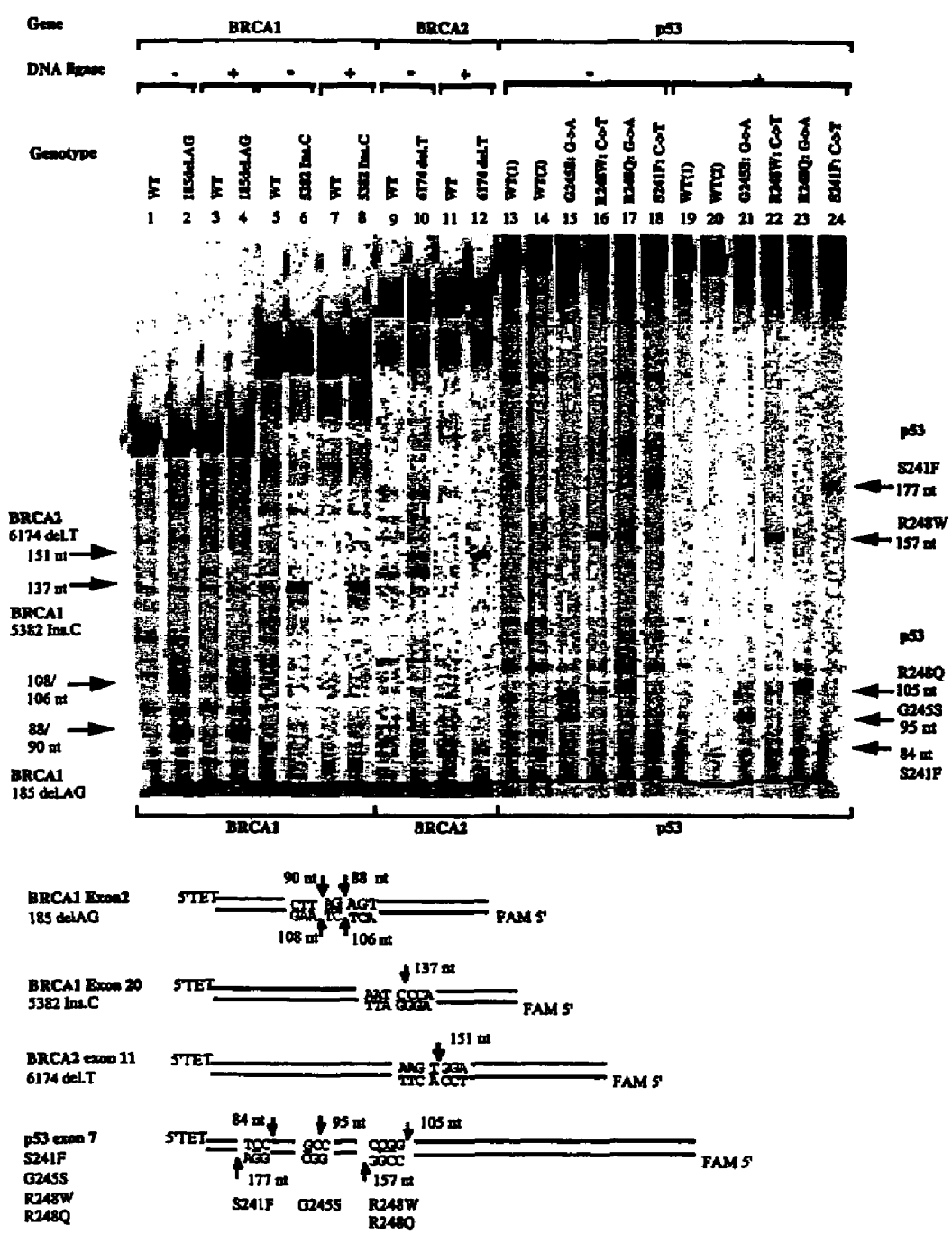
FIG. 15 demonstrates the ability of the present invention to detect small insertion/deletion in BRCA1 and BRCA2, and point mutations in the p53 gene.

The gel image showed that the cleavage of the AG deletion mismatch of BRCA 1 was very strong, but the cleavage bands associated with the C insertion of BRCA 1 and the T deletion of BRCA 2 are faint (FIG. 15). A non-specific band below the cleavage band of the T deletion was removed after ligation, which indicates that non-specific nicks can be sealed by the ligase. For the VHL gene, the cleavage of the AGA insertion is very strong, and the cleavage of an A insertion is also good (Table 4). These results demonstrate that endo V can recognize and cleave a two to three nucleotide insertion or deletion efficiently. It also can detect a one nucleotide insertion or deletion, but the efficiency was observed to be less than that of a two or three nucleotide change.

A comparison of lanes 13–18 with lanes 19–24 demonstrate the advantages of using a DNA ligase step for distinguishing point mutations in the p53 gene when using clinical samples. Significant background signal in lanes 13–18 is all but eliminated in lanes 19–24 allowing for unambiguous detection of mutant signals.

Example 20

Detection of Mutations in Long PCR Fragments

The ability of the present invention to mutation scan on longer PCR fragments was determined using a 1.7 kb PCR fragment from the p53 gene. The sequences of the PCR primers used to amplify this 1.7 kb segment are listed in Table 2A, while PCR thermocycle conditions are listed in Table 2B. In order to remove Taq DNA polymerase, 1 oil of proteinase K was added (20 mg/ml, QIAGEN) for every 12 μl of PCR products. This reaction was incubated at 70° C. for 10 min and at 80° C. for 10 min to inactivate the Proteinase K. Heteroduplex fragments were then formed by heating the mixture at 94° C. for 1 min, 65° C. for 15 min, and then cooling down to room temperature. The PCR fragments were then washed twice with 10 mM Tris pH 7.5 and excess dNTP and primers were removed by a Microcon 30 filter (Millipore) centrifugation step before endo V cleavage reaction. This resulted in the buffer condition changing and the volume being reduced to half of the original volume before washing. Therefore, the DNA concentration was increased two fold to about 10–20 ng/μl. The Tma endo V cleavage reaction was performed at 65° C. for 1 hour in the buffer containing 10 mM HEPES (pH 7.4), 1 mM DTT, 2% glycerol, 200 ng PCR heteroduplex fragments, 5 mM MgCl$_2$, 1.5 M betaine, 2% DMSO, and 500 nM Tma endo V. After the endo V reaction, the fragments were washed again to remove betaine and DMSO. The ligation was performed at 65° C. for 20 min in the presence of 1–6 nM Tsp. AK16D ligase in a buffer containing 20 mM Tris-HCl (pH7.6), 5 mM MgCl$_2$, 50 mM KCl, 10 mM DTT, 1 mM NAD$^{30}$, and 20 μg/ml BSA.

Figure 16:
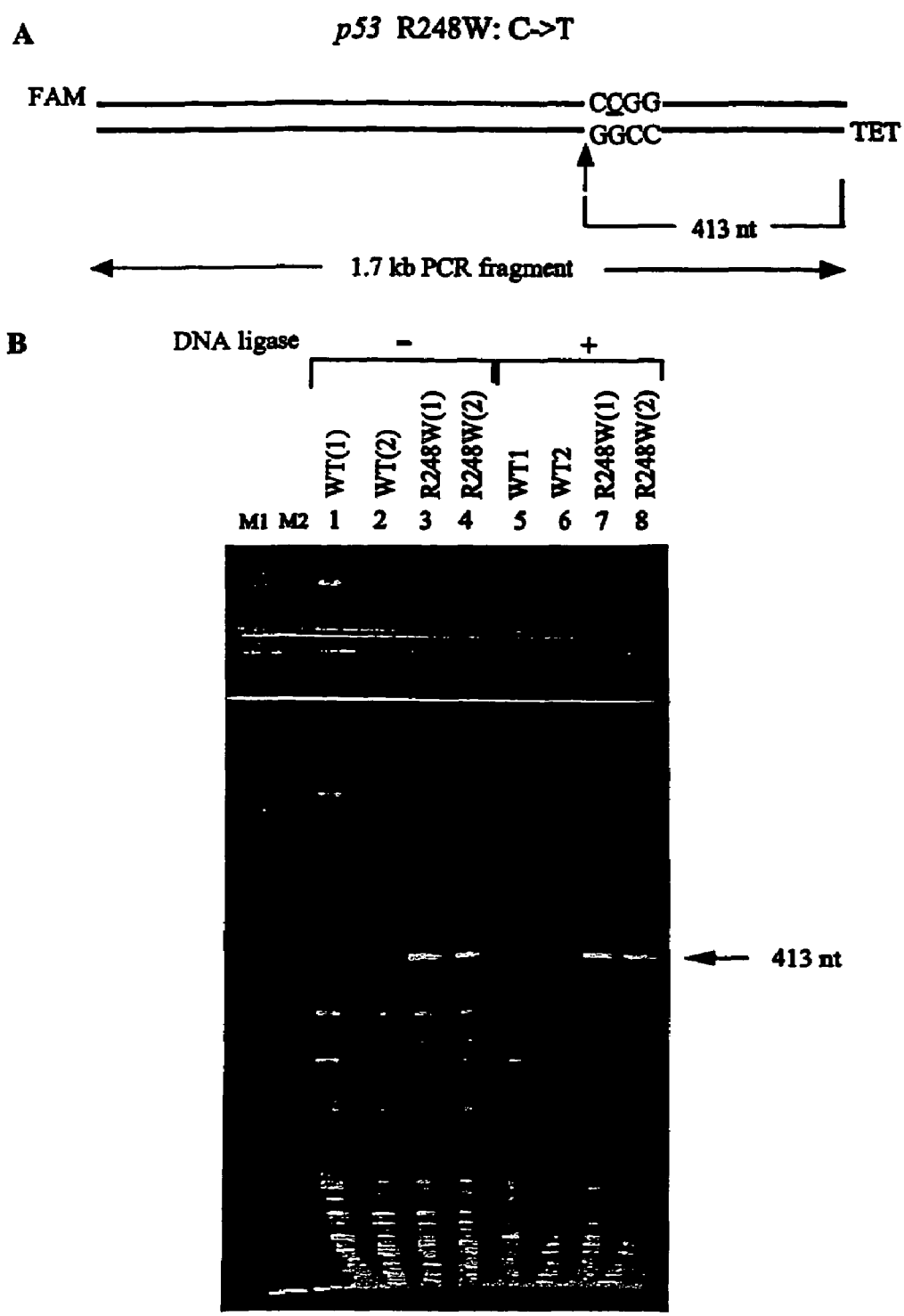
FIGS. 16A–B collectively show that the present invention can detect a mutation in a region of DNA as large as 1.7 kb.

This procedure was performed using genomic DNA containing p53 R248W (C→T) as the template, and 400 bp, 800 bp, 1.2 kb and 1.7 kb fragments containing the R248W mutation were amplified. This assay demonstrates that the invention can detect mutations in PCR fragments up to 1.7 kb in size and potentially higher (FIG. 16). Top strand cleavage (TET labeled) was also observed in these assays.

Example 21

Micro DNA Sequencing to Detection of P53 R248w(C→T)

The strategy of micro-DNA sequencing is illustrated in FIGS. 16A and 18A. The DNA fragment containing p53 R248W(C→T) was PCR amplified with unlabeled primers. The sequences of PCR primers are listed in Table 2A, and the PCR thermocycle conditions are listed in Table 2B. PCR fragments containing p53 R248W(C→T) were mixed with equal amounts of wild type PCR fragments. In order to remove Taq DNA polymerase, 1 μl of proteinase K was added (20 mg/ml, QIAGEN) for every 12 μl of PCR products. This reaction was incubated at 70° C. for 10 min and at 80° C. for 10 min to inactivate the Proteinase K. Heteroduplex fragments were then formed by heating the mixture at 94° C. for 1 min, 65° C. for 15 min, and then cooling down to room temperature. The PCR fragments were then washed twice with 10 mM Tris pH 7.5 and excess dNTP and primers were removed by a Microcon 30 filter (Millipore) centrifugation step before endo V cleavage reaction.

The Tma endo V cleavage reaction was performed at 65° C. for 1 hour in the buffer containing 10 mM HEPES (pH 7.4), 1 mM DTT, 2% glycerol, 200 ng PCR heteroduplex fragments, 5 mM MgCl$_2$, 1.5 M Betaine, 2% DMSO, and 500 nM Tma endo V. After the endo V reaction, the fragments were washed again to remove betaine and DMSO. The ligation was performed at 65° C. for 20 min in the presence of 1–6 nM Tsp. AK16D ligase in a buffer containing 20 mM Tris-HCl (pH7.6), 5 mM MgCl$_2$, 50 mM KCl, 10 mM DTT, 1 mM NAD$^{30}$, and 20 μ/ml BSA. After ligation, the mixture was incubated at 65° C. for 20 min and then washed to remove salts.

The nicked heterduplex products were excised several nucleotides back from the nick 3'→5' with DNA polymerase I Klenow fragment. The reaction mixture (40 μl) contained 120 ng DNA from the ligation reaction, 1× E. coli. DNA polymerase I buffer, and 20 units DNA polymerase I Klenow fragment. The mixture was incubated at 37° C. for 30 min. The product of this reaction was subsequently used as substrate for a sequencing reaction.

The DNA sequencing reaction contained 30 ng DNA from the Klenow fragment reaction, 20 μM dNTP, 20 μM ddGTP, 224 μM ddTTP, 22 μM ddATP, 32 μM ddCTP, 1× sequencing buffer, and 1 μl of Taq DNA polymerase FS (Perkin Elmer lot #361451005). The ratio of the four dideoxynucleotide (A:C:G:T=0.11:0.16:0.10:1.12) was taken from Rosenblum, B. B. et al., "New Dye-Labeled Terminators for Improved DNA Sequencing Pattern," *Nucleic Acids Res.* 25:4500–4 (1997), which is hereby incorporated by reference. The reaction mixture was incubated at 60° C. for 30 sec using PE GeneAmp PCR system 2400 thermocycler. The excess BigDye dideoxynucleotide was removed by loading the reaction mixture on a Centri-Sep™ spin column P/N CS-90 (Princeton Separation, Adelphia, N.J.) and microcentrifuged at 3000 rpm for 2 min. Five μl of the eluate was added to an equal volume of GeneScan stop solution (50 mM EDTA, 80% formamide, and 1% blue dextran). After heating at 94° C. for 2 min, 1 μl of the mixture was loaded on a 10% denaturing polyacrylamide gel and electrophoresed at 1000 volts, 60 mA, 150 W, and a gel temperature of 45° C. Running time took approximately 4 hours. The Run Module was set to filter E and the Matrix was set to dRhodamine Matrix. The data was analyzed with GeneScan analysis (v.3.0a). See FIG. 16B.

For comparison of the sequence results, standard dRhodamine DNA cycling sequencing was also performed. The DNA template for this sequencing reaction was PCR product which was amplified with unlabeled PCR primers. The sample was then washed twice with 10 mM Tris pH 7.5 and excess primers were removed by a Microcon 30 filter (Millipore) centrifugation step. One of the unlabelled PCR primers was then added to be used as a sequencing primer. Standard DNA sequencing was performed using an ABI Prism dRhodamine Terminator Cycle Sequencing Ready Reaction Kit (Perkin Elmer). Twenty μl of the reaction mixture, containing 8.0 μl of terminator ready reaction mix, 6.0 μl of PCR products (10 ng/l), 1.0 μl of each PCR primer (3.2 μM), and 7 μl of ddH$_2$O, was incubated in a PE Gene Amp PCR System 2400 thermocycler for 25 cycles of 96° C. for 10 sec, 50° C. for 5 sec, and 60° C. for 4 min. After the reaction, the mixture was precipitated by adding 2 μl of 3 M NaAc (pH 4.6) and 50 μl of 95% ethanol, it was placed on ice for 10 min. After microcentrifuging for 15–20 min at maximum speed, the pellets was rinsed with 70% ethanol and dried. The pellet was then suspended in 4 μl of DNA sequencing loading buffer (5 mM EDTA, 1% blue dextran, and 80% formamide). After heating at 95° C. for 2 min., 1–2 μl of the mixture was loaded on a 10% polyacrylamide denaturing gel (small plate) and electrophoresed at 1000 volts, 60 mA, 150 W, and a gel temperature of 45° C. Running time was approximately 4 hours on an ABI DNA sequencer 377. The Run Module was set to filter E, and Dye Set/Primer File was set to DT {dR Set Any-primer}. The sequencing patterns were analyzed with DNA sequencing analysis software (v. 3.0)(see FIG. 18).

The sequence results for the bottom strand are shown in FIG. 18B (micro-DNA sequencing) and FIG. 18C (standard DNA sequencing). The position where G (blue color) and A (green color) peaks overlap indicates the position of the mismatch, and shows that the mutation is G→A (C→T for the top strand).

Example 22

Detection of K-ras G12V Mutation in PCR Fragments Containing 7-deaza-dGTP

In order to explore the possibility of using nucleotide analogues with Tma endonuclease V, the same concentration of 7-deaza-dgtp was used instead of regular dgtp in PCR reaction mixture. The PCR reaction was setup to amplify k-ras exon-1 using genomic DNA from a cell line containing wild type DNA (ht29) and mutant DNA g12v(g→t) (sw620). The PCR primers and PCR program, Tma cleavage and Tsp.DNA ligation conditions were the same as the standard conditions. To compare the cleavage products from the PCR fragment containing 7-deaza-dgtp, the cleavage products from PCR fragments containing regular dgtp were also loaded on the same gel.

The 7 position in 7-deaza-dGTP is a carbon instead of nitrogen (FIG. 17A). The PCR reaction was setup to amplify K-ras exon-1 using genomic DNA from cell line containing wild type DNA (HT29) and mutant DNA G12V(G→T) (SW620). In comparison to the cleavage products from the PCR fragment containing 7-deaza-dGTP, the cleavage products from PCR fragments containing regular dGTP were also loaded on the same gel. For the heteroduplex PCR fragment containing 7-deaza-dGTP, cleavage of the top strand containing (G→T) mutation was inhibited, while cleavage of the bottom strand containing (C→A) is still present (FIG. 17B). This result indicated a possible contact between Tma endonuclease V and N-7 in Guanine. While the use of 7-deazaG did not allow for cleavage of the refractory G13D mutation, the concept of lowering the stability of G-C base pairs by using a non-cleavable analogue was shown to be robust. Several additional (non-specific) cleavage products are observed in the second lane containing deazaG. Alternative analogues may be considered, especially those which base pair with guanosine but destabilize hybridization, such as 2-pyrimidinone instead of cytosine.

Example 23

Mutant Endonucleases

Wild type *Thermotoga maritima* Endo V can identify approximately 98% of the SNPs found in the human genome. To identify the remaining SNPs, or to achieve a more robust signal on existing SNPs or mutations, modified or novel Endo V enzymes may be required. This may be achieved by either introducing mutation(s) into *Thermotoga maritima* Endo V to alter its mismatch base specificity or by utilizing an Endo V from a different organism that has a different mismatch base specificity. A mutant *Thermotoga maritima* Endo V or an alternate Endo V could be used in the same reaction with wild-type *Thermotoga maritima* Endo V, to expand the repetoire of sequences which can be recognized in this assay.

Primary sequence alignment of different eukaryotic, prokaryotic, and archea Endo V orthologs revealed a few residues which appeared to be evolutionarily conserved. Nine different site-specific mutants (D43A, Y80A, R88A, E89A, D105A, D110A, H116A, H125A and, K139A) were constructed, and 5 of these (Y80A, R88A, E89A, H116A, and K139A) appear to have useful altered specificity (See Table 7).

TABLE 7

Summary of enzymatic and binding activity of Tma EndoV mutants.

| Tma endoV Mutants | wt | D43A | Y80A | R88A | E89A | D105A | D110A | H116A | H125A | K139A |
|---|---|---|---|---|---|---|---|---|---|---|
| Cleavage | I/A | | | | | | | | | |
| MgCl$_2$ | ++/++ | −/− | +++/− | +++/− | w/− | ++/++ | −/− | +++/− | ++/++ | ++/− |
| MnCl$_2$ | +/+ | −/− | ++/− | ++/w | +/− | +/+ | −/− | ++/w | +/+ | ++/− |
| Binding | I/A | | | | | | | | | |
| MgCl$_2$ | ++ | ++ | − | ++ | − | ++ | ++ | ++ | +++ | +++ |
| CaCl$_2$ | ++ | ++ | − | 1/2+ | + | ++ | ++ | − | ++ | ++ |
| EDTA | 1/2+ | ++ | − | − | + | 1/2+ | ++ | − | − | − |

TABLE 7-continued

Summary of enzymatic and binding activity of Tma EndoV mutants.

| Tma endoV Mutants | wt | D43A | Y80A | R88A | E89A | D105A | D110A | H116A | H125A | K139A |
|---|---|---|---|---|---|---|---|---|---|---|
| Predictions | wt | Catalytic Mg binding | Stacking | O2, O6 H-bond Accept.? | N1 H-bond Doner? | wt | Catalytic Mg binding | O2,6,N7 H-bond Accept.? | Almost wt | O2,6,N7 H-bond Accept.? |

In addition, this analysis identified two aspartates, D43 and D105, as being the catalytic residues for this enzyme.

The approach used to develop useful *Thermotoga maritima* Endo V mutants is based on creating site-directed mutants at positions that are involved in protein-substrate interactions. *Thermotoga maritima* Endo V demonstrates significantly greater cleavage activity with inosine or uracil within either a matched or mismatched substrate, as compared with mismatches containing the naturally occuring deoxyribonucleotide bases (dA, dC, dG, and dT). Therefore, one can increase the relative specificity of the enzyme for a natural base by decreasing the specificity of the enzyme for inosine or uracil, and/or increasing the specificity for a natural base.

Protein specificity for a substrate typically involves interactions between amino acid side chains of the enzyme and the functional groups of the substrate. Interactions involving amino acid side chains and substrate moieties of different chemical composition (e.g. hydrophobic/polar interactions) greatly destabilize substrate binding and can dramatically decrease the ability of an enzyme to utilize a specific substrate. Since the enzyme functions in vitro with dramatically higher activity with inosine and uracil containing substrates and the natural occurring deoxyribonucleotide bases are less favorably cleaved, this strongly suggests one or more destabilizing interactions associated with a natural base. Therefore, by mutagenizing the enzyme at positions of enzyme-mismatch base interactions, the specificity of the enzyme can be altered to favor naturally occurring deoxyribonucleotide bases. A similar approach has been successful with human UDG, which recognizes uracil within DNA substrates. Kavli et al., *The EMBO Journal* 15:3442–47 (1996), which is hereby incorporated by reference.

Figure 19:
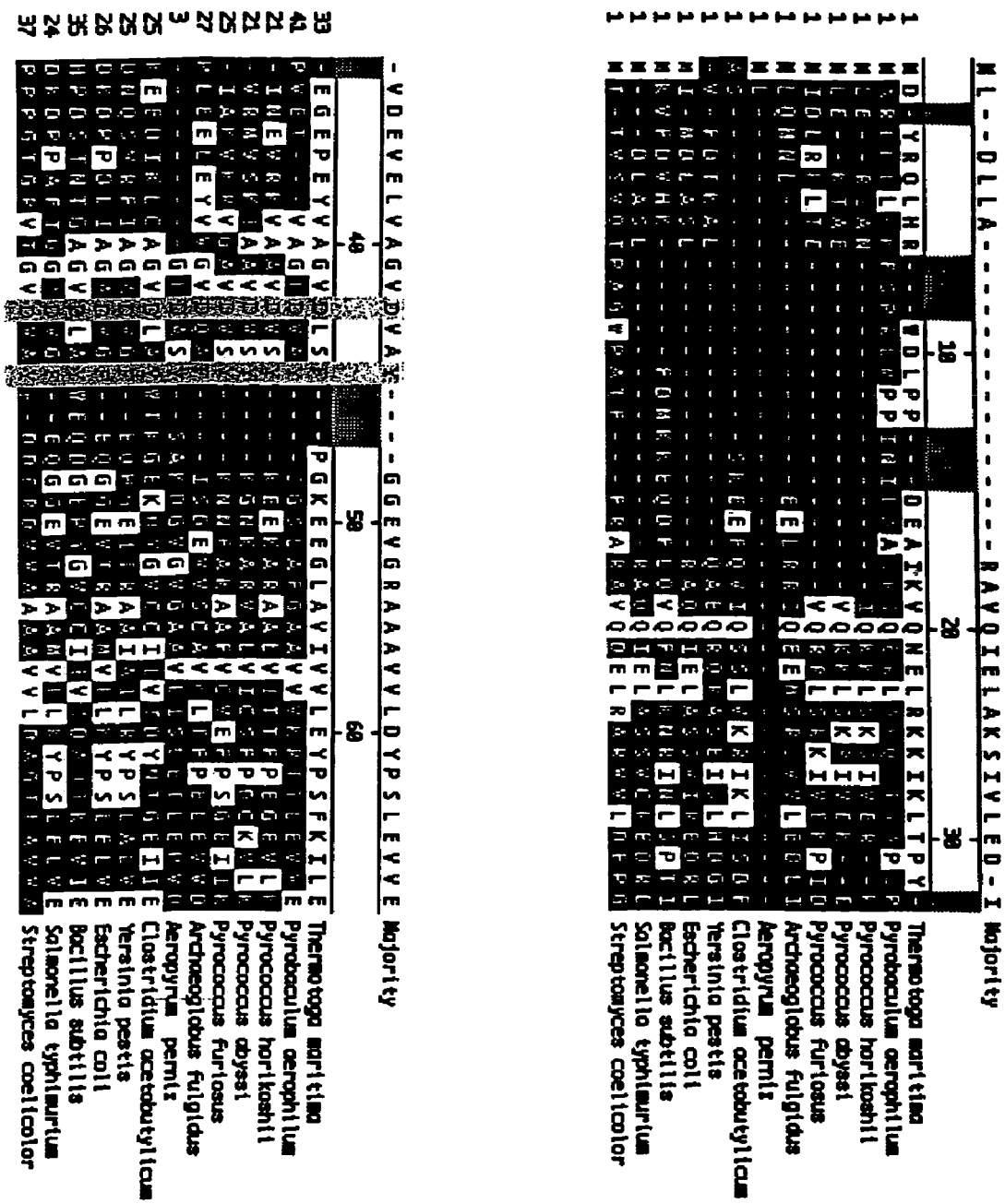
FIG. 19 presents the results of the alignment of 13 identified and putative endo V enzymes from thermophilic and mesophilic archeabacteria and eubacteria.
Figure 19:
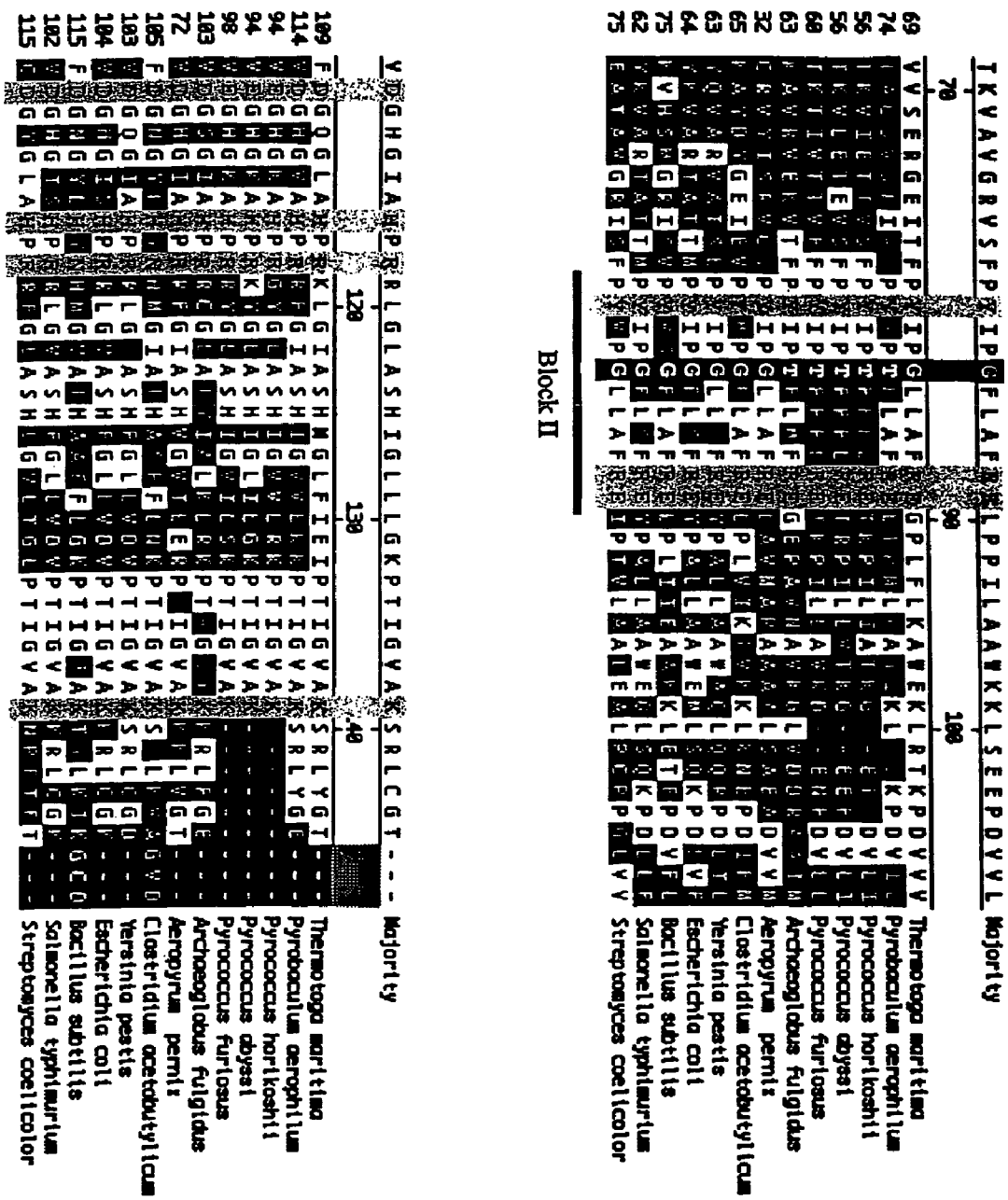

Residues that are involved directly in protein-substrate interactions have a strong tendency to be conserved among enzymes of the same family. Therefore, in a primary amino acid sequence alignment, highly conserved residues represent good candidates for mutagenesis. In order to identify positions in *Thermotoga maritima* Endo V suitable for mutagenesis, the ClustalW alignment algorithm with a PAM250 Residue Weight Table(Pairwise Alignment Parameters: Ktuple=1, Gap Penalty=3, Window=5, and Diagonals Saved=5; Multiple Alignment Parameters: Gap Penalty=10 and Gap Length Penalty=10) was used to perform a primary amino acid sequence alignment among 13 identified and putative Endo V enzymes from thermophilic and mesophulic archeabacteria and eubacteria (i.e. *Thermotoga maritima* (SEQ. ID. No. 37), *Pyrobaculum aerophilum* (SEQ. ID. No. 38), *Pyrococcus horikoshii* (SEQ. ID. No 39), *Pyrococcus abyssi* (SEQ. ID. No. 40), *Pyrococcus furiosus* (SEQ. ID. No. 41), *Archaeoglobus fulgidus* (SEQ. ID. No. 42), *Aeropyrum pernix* (SEQ. ID. No. 43), *Clostridium acetobutylicum* (SEQ. ID. No. 44), *Yersinia pestis* (SEQ. ID. No. 45), *Escherichia coli* (SEQ. ID. No. 46), *Bacillus subtilis* (SEQ. ID. No. 47), *Salmonella typhimurium* (SEQ. ID. No. 48), and *Streptomyces coelicolor* (SEQ. ID. No. 49), majority sequence, top line (SEQ. ID. No. 50) (FIG. 19)). Since the majority of enzymes utilized in the alignment are putative Endo V enzymes, the mismatch specificity of most of these enzymes is unknown. As a result, when utilizing the alignment to identify candidate residues in *Thermotoga maritima* Endo V, one can either assume that the homologous enzymes have similar or different specificities. If one assumes similar specificities, then residues that are highly conserved for the majority of Endo V provides candidates. Whereas if one assumes different specificities, then positions where there exists two sets of highly conserved residues represent candidates.

In analysis assuming similar mismatch specificity among the family of endo Vs, 12 residues (D43, F46, Y80, R88, E89, D105, D110, H116, R118, H125, K139, and F180) in *Thermotoga maritima* Endo V have been identified that were 1) highly conserved for the majority of Endo V enzymes and were 2) best suited for mutagenesis. Although aliphatic hydrocarbon chains (i.e. L, I, V, and M residues) can play a role in protein-substrate interactions, positions of high conservation with these residues are not listed, since they can also play a role in stabilizing the hydrophobic core of the enzyme. In addition, highly conserved prolines and glycines should be avoided for mutagenesis due to the unique chemical and structural influences associated with these amino acid residues. From the initial set of 12, 9 different site-specific mutants (D43A, Y80A, R88A, E89A, D105A, D110A, H116A, H125A and, K139A) and 5 of these mutant endo Vs (Y80A, R88A, E89A, H116A, and K139A) appear to have useful altered specificity. These results demonstrate that the present invention is useful for identifying *Thermotoga maritima* Endo V positions to mutate in order to confer altered specificity. Since the chemical nature of the polar group (e.g., hydrogen bond donator vs. hydrogen bond acceptor) can also have a strong influence on substrate specificity, further mutations at these positions can facilitate the generation of a mutant Endo V enzymes that extend the capabilities of the current invention (Table 8).

TABLE 8

EndoV Mutants, Group 1.

| | Remove Destabilizing Residue | Add Stabilizing Residue | Modify Stability |
|---|---|---|---|
| F46 | F46A | F46Y | F46(L,I,V,M) |
| Y80 | Y80A | Y80F | Y80(L,I,V,M) |
| R88 | R88A | R88(L,I,V,M) | R88K |
| | | | R88(N,Q) |
| | | | R88(D,E) |
| | | | R88(T,S) |

TABLE 8-continued

EndoV Mutants, Group 1.

| | Remove Destabilizing Residue | Add Stabilizing Residue | Modify Stability |
|---|---|---|---|
| E89 | E89A | E89(L,I,V,M) | E89D |
| | | | E89(T,S) |
| | | | E89(R,K) |
| | | | E89(Q,N) |
| H116 | H116A | H116(L,I,V,M) | H116(R,K) |
| | | | H116(N,Q) |
| | | | H116(D,E) |
| | | | H116(T,S) |
| R118 | R118A | R118(L,I,V,M) | R118K |
| | | | R118(N,Q) |
| | | | R118(D,E) |
| | | | R118(T,S) |
| K139 | K139A | K139(I,L,V,M) | K139R |
| | | | K139(N,Q) |
| | | | K139(D,E) |
| | | | K139(T,S) |
| F180 | F180A | F180Y | F180(I,L,V,M) |

In the examples provided infra, substituting an alanine would be predicted to remove destabilizing residues for a naturally occuring base at a mismatch. Alternatively, altering a charged polar residue with a pure hydrophobic residue may increase the stability or binding affinity of a naturally occuring base at a mismatch. In addition, changing a residue from a positive to negative charge may alter the specificity of the enzyme, such that a natural base at a mismatch is preferred. Since interactions between substrate and enzyme may involve complex hydrogen bond networks, altering two or more of the residues listed in Table 7 may be required to obtain better activity of the enzyme to mismatches containing natural bases. Further, subtle changes in the catalytic residues, such as D43E or D105E, may assist in catalysis of naturally occuring base at a mismatch.

In analysis assuming dissimilar mismatch specificity among some members of the Endo V family, 2 residues (G83 and I179) were identified that contain two separate sets of conserved sequence. For example, the residues homologous to I179 of *Thermotoga maritima* Endo V, are either a polar-charged residue (K) or an aliaphatic residue (L, I, or V). If this position is involved in making an interaction with a DNA base at the mismatch, the composition of the residue (polar and charged vs. hydrophobic) would influence which substrates are preferred. The conserved set different from *Thermotoga maritima* endo V at the given position as the basis for initial mutagenesis (e.g., I179K) (Table 9) was used.

TABLE 9

EndoV Mutants, Group 2.

| | Remove Destabilizing Residue | Add Stabilizing Residue | Modify Stability |
|---|---|---|---|
| G83 | | | G83(T,S) |
| | | | G83(N,Q) |
| | | | G83(D,E) |
| | | | G83(R,K) |
| | | | G83A |
| | | | G83(L,I,V,M) |
| I179 | I179A | | I179(R,K) |
| | | | I179(N,Q) |
| | | | I179(D,E) |
| | | | I179(T,S) |

In addition to developing mutant *Thermotoga maritima* Endo V enzymes, the cloning of other thermostable Endo V enzymes provides a source of alternative, but functionally similar, enzymes for use in the present invention. This invention is capable of utilizing other thermostable Endo V enzymes, or other endonucleolytic enzymes as long as the products are compatible with the thermostable ligase step of the invention. By utilizing a themostable Endo V with different substrate specificities from *Thermotoga maritima* Endo V, the capabilities of the present invention can be further extended.

Example 24

Mutation Scanning Using a Combined Endo V/DNA Ligase Assay

An analysis of p53 mutations in colon tumor DNA using a combination of both PCR/LDR/array and Endo V/Ligase mutation scanning proved superior to automated sequencing (see Table 10). Of 23 samples shown to have 26 p53 mutations by PCR/LDR combined with Endo V/ ligase, 8 samples were missed by automated sequencing (65% true positive, 35% false negative). Mutation detection in five samples called positive with Endo V/Ligase mutation scanning, required gel purification of PCR fragments, and re-sequencing of both strands with manual reading. Significantly, Endo V/Ligase mutation scanning scored all four frameshift mutations, which accounts for almost 20% of the samples with p53 mutations. Such frameshift mutations are beyond the detection capacity of commercially available p53 hybridization chips.

TABLE 10

Detecting p53 mutations in tumor samples: Comparisons of using a combined analysis with PCR/LDR and EndoV/ligase mutation scanning to Dideoxysequencing.

| Sample #: (50 total) | PCR/LDR Universal Array | Endov/Ligase Mutation Scanning | Dna sequencing, Automated Read | Resequencing of both strands, Manual read |
|---|---|---|---|---|
| 53 | (5) R175 G2-A | | (5) R175 G2-A | |
| 55 | (8) E285 G1-A | (8) E285 G1-A | (8) E285 G1-A | |
| 59 | (8) R273 C-T | | (8) R273 C-T | |

TABLE 10-continued

Detecting p53 mutations in tumor samples: Comparisons of using a combined analysis with PCR/LDR and EndoV/ligase mutation scanning to Dideoxysequencing.

| Sample #: (50 total) | PCR/LDR Universal Array | Endov/Ligase Mutation Scanning | Dna sequencing, Automated Read | Resequencing of both strands, Manual read |
|---|---|---|---|---|
| 60 | (8) R282 C-T, (8) R306 C-T | (5) K164 A-T | | (5) K164 A-T, (8) R306 C-T) |
| 65 | (5) R175 G2-A | | (5) R175 G2-A | |
| 66 | (7) R248 G-A | (7) R248 G-A | | (7) R248 G-A |
| 67 | (8) R282 C-T | (8) R282 C-T | | (8) R282 C-T |
| 68 | | (6) Y205 A-T | | (6) Y205 A-T* |
| 71 | (8) R273 C-T | | (8) R273 C-T | |
| 73 | (8) R282 C-T | (5) Q167 delGT, (8) R282 C-T | (8) R282 C-T | (5) Q167 delGT* (8) R282 C-T |
| 77 | | (7) S261 T-G | (7) S261 T-G | |
| 78 | (7) R248 C-T | (7) R248 C-T | | (7) R248 C-T |
| 79 | | (7) S240 delA | | (7) S240 delA* |
| 80 | (5) R175 G2-A | | (5) R175 G2-A | |
| 81 | (5) R175 G2-A | | (5) R175 G2-A | |
| 84 | | (7) S261 T-G | (7) S261 T-G | |
| 89 | | (6) Q192 C-T | (6) Q192 C-T | |
| 90 | | (6) H214 delT | | (6) His 214 delT* |
| 93 | (5) R175 G2-A | | (5) R175 G2-A | |
| 94 | | (6) H214 delT | | (6) His 214 delT* |
| 96 | (8) R273 G-A | (8) R273 G-A | (8) R273 G-A | |
| 97 | | (8) R276 C-G | (8) R276 C-G | |
| 98 | (8) R282 C-T | (8) R282 C-T | (8) R282 C-T | |
| (27 samples) | No Mutation | No Mutation | Not determined# | Not determined# |
| Score | 15/23 (16 known, 4 new, 4 deletions) | 16/23 (2 resistant sites, observed 6 times) | 15/26 | 20/26 |
| Percent | 65% | 70% | 57% | 77% |
| Combined | | 100% | | 83% |
| Adjusted | 16/16 | 16/17 | 15/23 | 23/23 |
| Percent | 100% | 94% | 65% | (100%) |

*Required gel purification of PCR product to obtain sequencing result.
Sequencing of 5 random samples of 27 called negative by PCR/LDR and EndoV/Ligase reveal no new mutations.

Mixing experiments using three different K-ras mutations demonstrated that the Endo V/ ligase reaction is also a sensitive assay: mutation can be detected above background when 1 mutant sequence is diluted with 20 wild-type sequences.

The colon tumor DNA was isolated from non-microdissected samples, with stromal cell infiltration from about 10%–50%. Mutation of one p53 allele is invariably accompanied by loss of heterozygosity ("LOH") of the other allele, occuring either through chromosome loss or through mitotic nondisjunction (i.e. both mutant chromosomes migrate to the daughter cell). Thus, DNA from the above samples would have a range of mutant p53: wild-type allele of from about 90%:10% (for nondisjunction with 10% stroma) to 33%: 67% (for chromosome loss with 50% stroma). When the above samples were reanalyzed for p53 mutations in pools of 3 samples, the Endo V mutation scanning assay could still identify the presence of all the mutants. Several of the pooled sample bands were even stronger than from individual samples (suggesting the original sample was mostly mutant DNA), while a few bands were weaker but could still be detected (suggesting the original sample had substantial stromal contamination). The ability to detect mutations in pools of 5 or even 10 samples would significantly improve cancer mutation scoring.

Example 25

Site-Directed Mutagenesis of Tma EndoV

Alanine scanning mutagenesis was performed at nine conserved positions of *Thermotoga maritima* endoV to identify amino acid residues important for its endonuclease activity (Table 11). Alanine substitution at the DDE motif residues D43, E89, D110, abolish or substantially reduce inosine cleavage activity. These mutants also gain binding affinity to double-stranded or single-stranded inosine substrate in the absence of a metal ion, suggesting that these residues are involved in the coordination of catalytic $Mg^{2+}$. Y80A, H116A, and, to a lesser extent, R88A, demonstrate reduced affinity to double-stranded or single-stranded inosine substrate or nicked product. The lack of tight binding to nicked inosine product accounts for an observed increase in turnover of inosine substrate since the product release is less rate-limiting. Y80A, R88A, K139A, and, to a lesser extent, H116A show reduced activity towards AP and uracil substrates. Consistent with their location in or near the base recognition pocket, these residues may play a role in substrate recognition.

TABLE 11

DNA Cleavage Activity of Nine Tma Endov Mutants[a]

| Tma endoV Mutants | wt | D43A | Y80A | R88A | E89A | D105A | D110A | H116A | H125A | K139A |
|---|---|---|---|---|---|---|---|---|---|---|
| I/A | ++ | − | ++ | ++ | + | ++ | − | ++ | ++ | ++ |
| A/U | +++ | − | − | − | − | +++ | − | + | ++ | − |
| G/U | +++ | − | − | + | − | +++ | − | ++ | +++ | + |
| T/U | +++ | − | − | ++ | − | +++ | − | ++ | +++ | + |
| AP | +++ | − | − | − | − | +++ | − | + | +++ | − |
| ssI | ++ | − | ++ | ++ | + | ++ | − | ++ | ++ | ++ |

[a]The cleavage reactions were performed at 65° C. for 30 minute in a 20 μl reaction mixture containing 10 mM HEPES (pH 7.4), 1 mM DTT, 2% glycerol, 5 mM MgCl$_2$, 10 nM DNA substrate, 100 nM purified Tma endoV mutants. The reactions were terminated by adding an equal volume of GeneScan stop solution. The reaction mixtures were then heated at 94° C. for 2 min. and cooled on ice. Three microliters of samples were loaded onto a 10% GeneScan denaturing polyacrylamide gel (Perkin Elmer). Electrophoresis was conducted at 1500 voltage for 1 hr using an ABI 377 sequencer (Perkin Elmer). ss I: single stranded inosine-containing substrate. The number of plus signs represents the extent of cleavage of inosine-, uracil-, or AP site-containing strand. +++ = about 10%; ++ = about 5%; + = about 2%; − no cleavage observed.

Figure 20:
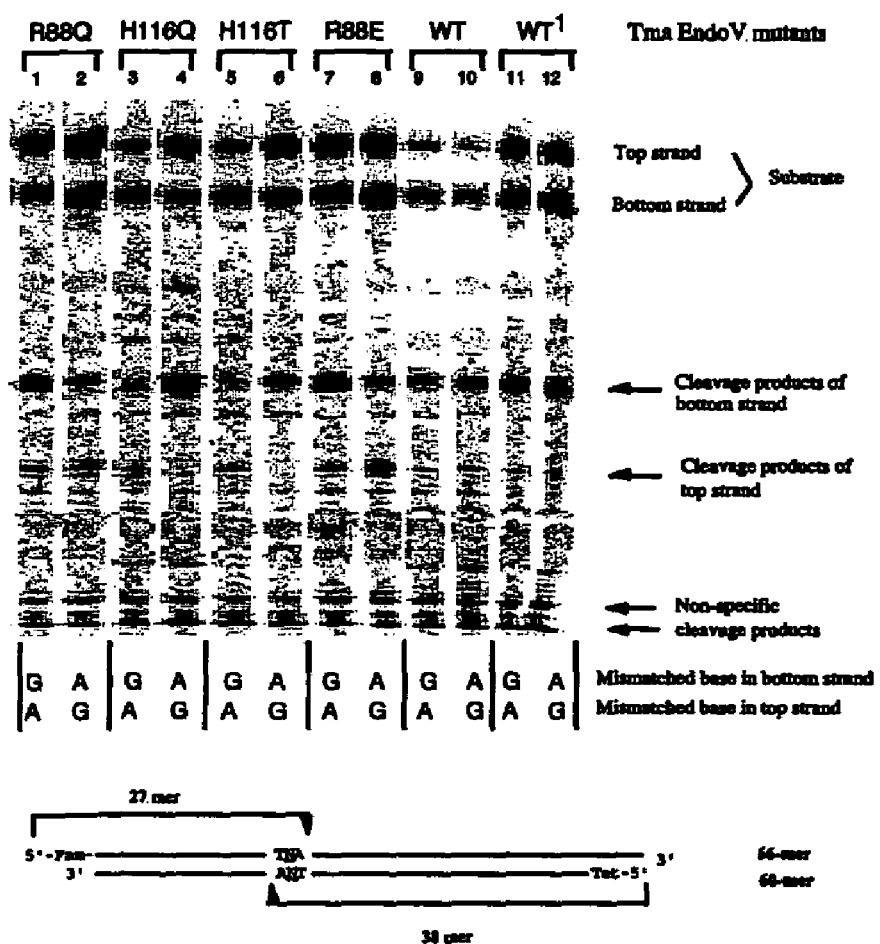
FIG. 20 shows the activities of mutant Endo V R88Q, R88E, H116Q, and H116T on synthetic substrates containing A:G and G:A mismatches. The cleavage reactions were performed at 65° C. for 30 minute in a 20 μl reaction mixture containing 10 mM HEPES (pH 7.4), 1 mM DTT, 2% glycerol, 1 mM $MnCl_2$, 20 nM DNA substrate, and 20 nM purified Tma endo V mutants. The reactions were terminated by adding an equal volume of GeneScan stop solution. The reaction mixtures were then heated at 94° C. for 2 min. and cooled on ice. Three microliters of samples were loaded onto a 10% GeneScan denaturing polyacrylamide gel (Perkin Elmer, Foster City, Calif.). Electrophoresis was conducted at 1500 voltage for 1 hr using an ABI 377 sequencer (Perkin Elmer). Lane 1–12 indicated the cleavage products as analyzed on a 10% denaturing polyacrylamide gel. As a control, wild-type Endo V was also assayed at 10 nM (WT, lane 9, 10) and 3 nM (WT[1]lane 11 and 12), respectively.

Site-specific mutagenesis was used to generate additional mutations at R88 (-→K, Q, E), H116 (-→Q, T, E), and K139 (-→Q, E). These mutants substantially lost activity using Mg$^{2+}$ as cofactor. Four of the mutants (R88Q, R88E, H116Q, and H116T) cleaved certain substrates in Mn$^{2+}$ better than wild-type enzyme does (See FIG. 20, lanes 4 & 6 compared to lane 12, and Table 12). This result is not surprising since the mutant presumably binds the substrate less well than wild-type enzyme, and, consequently, there is less non-specific binding and cleavage. The R88Q and R88E enzymes demonstrated a stronger preference for cleaving the G base in both G:A and A:G mismatched substrate than wild-type enzyme. Significantly, the preferred cleavage site of the "G" strand is now predominantly at the 3' side of the mismatched base (See FIG. 20, Lane 1 & 7, Table 12). Wild-type enzyme does not cleave the C strand in the A:C substrate, while the R88 mutant had medium level activity, with the preferred cleavage site of the "C" strand now two bases from the 3' end of the mismatch (Table 12).

TABLE 12

Cleavage Intensities of various substrates treated with wild-type and mutant Tma EndoV.

| Metal/Substr. | WT | WT | R88Q | R88Q | R88E | R88E | H116Q | H116Q | H116T | H116T |
|---|---|---|---|---|---|---|---|---|---|---|
| Mn2+ | G: ++ | A: +++ | G: +++[2] | A: ++[4] | G: ++++[2] | A: ++[4] | G: +[1] | A: ++++ | G: | A: +++[4] |
| | A: w | G: + | A: ++[4] | G: +++ | A: ++[4] | G: +++ | A: ++[3] | G: | A: ++[4] | G: |
| | A: ++++ | G: +++ | A: +++[4] | G: ++[2] | A: ++++ | G: ++++ | A: ++++ | G: | A: ++++ | G: |
| | A: +++ | G: ++ | A: ++ | G: ++[3] | A: +++ | G: +++[3] | A: ++ | G: | A: +++ | G: |
| | C: + | A: +++ | C: | A: +++[4] | C: | A: ++[4] | C: + | A: ++ | C: + | A: +++ |
| | A: ++ | C: | A: ++[4] | A: ++[6] | A: ++[4] | C: +[6] | A: w | C: w | A: ++[4] | C: +[6] |
| | T: ++++ | G: ++++ | T: w | G: +[2] | T: +[4] | G: +++[2] | T: +++ | G: w | T: ++ | G: w |
| | G: +++ | T: +++ | G: +[3] | T: +[4] | G: ++[3] | T: +[5] | G: | T: ++ | G: | T: +[4] |
| Mg2+ | A: ++++ | G: + | A: | G: | A: w | G: | A: w | G: | A: ++ | G: |
| | A: + | G: w | A: | G: | A: | G: | A: | G: | A: w | G: |

Endo V cleavage 0, 1, 2 nucleotides 3' to the mismatch.
(6) ↓ >95% cleavage two nucleotides 3' to the mismatch.
(5) ↓↓ 80% cleavage one nucleotide 3' to the mismatch, 20% two nucleotides 3' to the mismatch
(4) ↓ >95% cleavage one nucleotide 3' to the mismatch.
(WT) ↓↓↓ 80%–90% cleavage one nucleotide 3' to the mismatch, equal minor bands, both sides.
(3) ↓↓ 50% cleavage 3' to the mismatch, 50% one nucleotide 3' to the
(2) ↓↓ 70% cleavage 3' to the mismatch, 30% one nucleotide 3' to the
(1) ↓ >95% cleavage 3' to the mismatch.

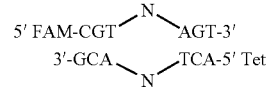

5' FAM-CGT   N   AGT-3'
3'-GCA   N   TCA-5' Tet

Superscripts (1–6) indicate cleavage patterns and relative intensities. No superscript indicates cleavage pattern was similar to wild-type (WT) enzyme. Overall cleavage intensities estimated based on uncut starting substrate. (++++) = about 30%; (+++) = about 20%; (++) = about 10%; (+) = about 5%; (w) = about 2%.

Both Tma EndoV H116Q and H116T exhibited almost exclusive activity towards adenosine containing substrates (FIG. 20, Table 12, lanes 4 and 6), with cleavage at the correct penultimate position. There was almost no activity towards the "G" containing strand, suggesting these mutant enzymes are the first step towards development of stronger enzymes for specific mismatched sequences. The change in cleavage site for the R88 and H116 mutants suggests significant plasticity in binding specific mismatched DNA by variant enzymes, further emphasizing the need for multiple crystal structures to understand non-classical cleavage for specific mismatches.

Example 26

Alanine Scanning Mutagenesis

An overlapping extension PCR procedure was used for site-directed mutagenesis (Ho, S. et al., *Gene* 77:51–59 (1989), which is hereby incorporated by reference in its entirety). PCR products digested with a pair of NdeI and SpeI were ligated to cloning vector pEV5 treated with the same pair of restriction endonucleases. The ligated vectors were transformed into *E. coli* strain AK53 (mrrB⁻, MM294). Plasmids containing inserts were reisolated and sequenced on a ABI sequencer using Dye-dideoxy terminator chemistry to identify mutated sequence and ensure that the constructs were free of PCR error. Strains containing mutated Tma endonulcease V (nfi) genes were expressed in 5 ml of MOPS medium supplemented with 50 µg/ml ampicillin (Neidhart, F. C., et al., *J. Bacteriol.* 119(3):736–47 (1974), which is hereby incorporated by reference in its entirety) at 37° C. overnight. Cell pastes were suspended in 300 µl of sonication buffer and sonicated 4×10 sec at 4° C. using a Sonifier Cell Disruptor 350 (Branson). After removing cell debris by centrifugation, the supernatants containing Tma endonuclease V proteins were incubated at 70° C. for 15 min to inactivate host proteins. The denatured proteins were separated from soluble Tma endonuclease V proteins by centrifugation. The protein concentrations of Tma endonuclease V mutants were quantified by scanning a 12.5% SDS-PAGE gel loaded with known amounts of wild-type Tma endonuclease V. Partially purified proteins were diluted to 1 µM with 1×TaqI storage buffer and stored at −20° C. prior to use.

Example 27

DNA Cleavage Reaction For Assaying Variant Endonucleases

The fluorescence labeled deoxyoligonucleotide substrates were prepared as described (Huang, J., et al., *Biochemistry* 40(30):8738–8748 (2001), which is hereby incorporated by reference in its entirety). The sequence of a typical inosine substrate (SEQ. ID. Nos. 1–2, respectively) is as follows:

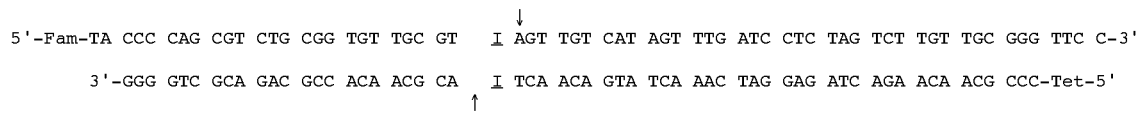

A nick event at the top strand generates a 27 nt labeled product while that at the bottom strand generates a 38 nt labeled product. The cleavage reactions were performed at 65° C. for 30 minute in a 20 µl reaction mixture containing 10 mM HEPES (pH 7.4), 1 mM DTT, 2% glycerol, 5 mM MgCl₂ unless otherwise specified, 10 nM DNA substrate, indicated amount of purified Tma endonuclease V protein. The reaction was terminated by adding an equal volume of GeneS can stop solution. The reaction mixtures were then heated at 94° C. for 2 mm and cooled on ice. Three microliter of samples were loaded onto a 10% GeneS can denaturing polyacrylamide gel (Perkin Elmer). Electrophoresis was conducted at 1500 voltage for 1 hr using an ABI 377 sequencer (Perkin Elmer). Cleavage products and remaining substrates quantified using the GeneScan analysis software versions 2.1 or 3.0.

Example 28

Gel Mobility Shift Assay

The binding reaction mixture contains 100 nM double stranded fluorescence-labeled oligonucleotide DNA substrates, 5 mM MgCl₂ or CaCl₂ or 2 mM EDTA, 20% glycerol, 10 mM HEPES (pH 7.4), 1 mM DTT, and 75 nM of Tma endonuclease V protein. The binding reactions were carried out at 65° C. for 30 min. Samples was electrophoresed on a 6% native polyacrylamide gel in 1×TB buffer supplemented with 10 mM MgCl₂ or CaCl₂ or 2 mM EDTA. The bound and free DNA species were analyzed using FluorImager 595 (Molecular Dynamics) with the following settings: PMT at 1000 Volt, excitation at 488 nm, emission at 530 nm (Filter 530 DF30). Data analysis was carried out using ImageQuaNT v4.1 (Molecular Dynamics).

Example 29

DNA Cleavage By Variant Endonucleases

Tma endo V mutants were generated through an overlapping PCR procedure and partially purified through heat-treatment at 75° C. for 15 min. The resulting mutant proteins are devoid of the indigenous *E. coli* endonuclease V (Huang, J., et al., *Biochemistry* 40(30):8738–8748 (2001), which is hereby incorporated by reference in its entirety). The cleavage assays were performed using oligonucleotide substrates fluorescently labeled at both strands. Previous studies have shown that the wild-type Tma endo V nicks at inosine sites. When the enzyme is in excess, it cleaves the complementary strand opposite of the inosine-containing strand (Huang, J., et al., *Biochemistry* 40(30):8738–8748 (2001), which is hereby incorporated by reference in its entirety). As expected for the wild-type control, a blue band was observed which represented the top inosine cleavage product and a green band which represented the bottom complementary strand cleavage product (FIG. 21A). Some lower molecular weight nonspecific cleavage products were also observed. D43A and D110A lost DNA endonuclease activity for cleaving either of the strands. E89A exhibited limited cleavage of the inosine strand with no detectable cleavage of the complementary strand. Y80A, R88A, H116A, and K139A maintained wt level cleavage activity towards inosine strand but lost complementary strand cleavage activity. D105A and H125A essentially maintained wt cleavage activity toward both the inosine-containing strand and the complementary strand in the double-stranded substrate (FIGS. 21A–C). Mn²⁺ enhanced non-specific cleavage activity but the overall cleavage profiles of the mutants remained similar to Mg²⁺ (FIGS. 21B–C).

Example 30

Binding to Inosine Substrate by Variant Endonucleases

A fluorescence-based gel mobility shift assay was used to compare substrate binding among the nine alanine-substituted mutants (Huang, J., et al., *Biochemistry* 40(30):8738–8748 (2001), which is hereby incorporated by reference in its entirety). As previously reported, the wt Tma endo V did not form a stable complex with the inosine substrate in the absence of a metal cofactor ((Huang, J., et al., *Biochemistry* 40(30):8738–8748 (2001), which is hereby incorporated by reference in its entirety) and FIG. 22A). Interestingly, the two catalytically inactive mutants D43A and D110A now formed a distinct complex with the inosine substrate. Although not observed in most mutational studies performed on endonucleases, the restriction endonuclease MunI does show such a peculiar property, i.e., elimination of the negative charges at some metal binding residues confer binding specificity to the cognate sequence (Lagunavicius, A., et al., *Biochemistry* 36(37):11086–11092 (1997), which is hereby incorporated by reference in its entirety). It is suggested that the negative charges may cause electrostatic repulsion between the carboxylates and the phosphate in the absence of a neutralizing metal ion. By substituting the negatively charged Asp or Glu with Ala, the mutants become capable of binding to the cognate sequence even without a metal ion. A similar notion can be applied to explain the binding behavior of D43A and D110A mutants, which implies that D43A and D110A are involved in the coordination of a divalent metal ion required for catalysis.

In the presence of a metal cofactor such as $Mg^{2+}$ or $Ca^{2+}$, most of mutants showed a binding affinity to the double-stranded inosine substrate comparable to that of the wt enzyme (FIG. 22B). Since $Ca^{2+}$ only supports binding but not catalysis (Huang, J., et al., *Biochemistry* 40(30):8738–8748 (2001), which is hereby incorporated by reference in its entirety), the shifted bands represent an ES (enzyme-substrate) complex. The shifted bands observed with $Mg^{2+}$, on the other hand, may represent an enzyme-nicked product complex due to strand cleavage. Apparently, Y80A and H116A no longer bind to the intact inosine substrate at tightly as the wt enzyme as judged by gel shift data with $Ca^{2+}$ (FIG. 22B). Further, the gel shift data with $Mg^{2+}$ suggested that Y80A and H116 may have reduced binding affinity to the nicked product as well (FIG. 22C). To more definitively assess the impact of alanine-substituted mutants had on endonuclease binding to the nicked product, gel mobility shift analysis was performed using a synthesized inosine oligonucleotide substrate with a preexisting nick (FIG. 23). It is evident from the gel shift experiments with $Ca^{2+}$ that Y80A, R88A, and H116A failed to bind to the nicked inosine product as tightly as the wildtype (i.e. wt) enzyme (FIG. 23A). Using the catalytically competent metal ion $Mg^{2+}$ as the metal cofactor, H116A bound the nicked inosine product about half as tightly as the wt enzyme (FIG. 23B). Y80A did not maintain bound to the nicked product with a long enough half-life to allow the detection of a distinct band shift (FIGS. 23B–C). These results suggested that some endo V variants such as Y80A and H116A may have affected both ES and EP binding, while R88A may primarily have affected product release.

A time course analysis was performed to assess how the altered binding behavior changed cleavage kinetics of the inosine-containing strand in a double-stranded sequence. When the enzyme is in deficit (E:S=1:10), the wt enzyme only cleaved a limited amount of the substrate as it remained bound to the nicked product (FIG. 24). Likewise, the mutant H125A, which showed wt level cleavage activity and binding affinity, also failed to turnover this inosine-containing double-stranded substrate. The three mutants Y80A, R88A, and H116A, which showed reduced affinities to the nicked inosine substrate by gel mobility shift analysis (FIG. 23), now were able to release the product and nicked the inosine strand in a multiple-turnover fashion (FIG. 24A). Most prominently, the cleavage reaction by Y80A proceeded close to completion with an apparent first order rate constant of 0.04 $min^{-1}$. The kinetic analysis, combined with the binding data, suggests that some of the mutants (as represented by Y80A) have changed the reaction kinetics by increasing the product release rate constant $k_3$ to facilitate multiple turnover (FIG. 24B).

Example 31

Cleavage and Binding of Single-Stranded Inosine Substrate By Variant Endonucleases To assess the single-stranded endonuclease activity, cleavage was examined using fluorescently labeled (Tet) inosine-containing single-stranded oligonucleotide. Most of the endo V variants retained wt cleavage activity toward the single-stranded inosine-containing substrate (FIG. 25A). Consistent with the cleavage results obtained using the double-stranded inosine-containing substrate (FIG. 21), E89A had a significantly reduced cleavage activity, while D43A and D110A were inactive toward the single-stranded inosine-containing substrate (FIG. 25A). The binding of single-stranded inosine-containing substrate also required a metal cofactor for most of the mutants. D43A, D110A, and E89A, however, were able to bind to the single-stranded inosine-containing substrate without a metal ion (FIG. 25B), suggesting a similar interaction among the enzyme, inosine substrate, and metal ion for both single-stranded or double-stranded substrates. The formation of a distinct shifted band by E89A in the absence of a metal ion using the single-stranded inosine substrate suggests that E89 may play an analogous role in metal binding similar to D43 and D110 (FIGS. 22A and 25B).

The binding pattern of the single-stranded inosine-containing substrate in the presence of $Ca^{2+}$ is essentially identical to that of the double-stranded substrate, i. e., most of the mutants exhibited a binding affinity at least as strong as the wt enzyme. Y80A and H116A again showed lower affinity to the inosine substrate (FIG. 25C). In the presence of $Mg^{2+}$, Y80A and H116A showed an intense lower molecular weight band with concurrent disappearance of the free DNA band, suggesting that most of the single-stranded substrate were cleaved (FIG. 25D). Given the reduced binding seen with $Ca^{2+}$, it is likely that these two mutants no longer bind to the single-stranded nicked product tightly, thereby dissociating from the product. D43A, D110A, and E89A were unable to cleave the inosine substrate or cleave at a much reduced rate (FIG. 25A). As expected, they formed a distinct stable complex as seen by mobility shift gel (FIG. 25D). However, they migrated faster than the wt and other catalytically active endo V mutants. One scenario to explain the different migration patterns is that the binding of the wt enzyme and some other active mutants may cause bending of the nicked inosine product (FIG. 25D), resulting in a slower migration (Lane, D., et al., *Microbiol Rev* 56(4):509–28 (1992), which is hereby incorporated by reference in its entirety). D43A, D110A, and E89A mutants may have lost the ability to bend the DNA due to the loss of the negative charges.

Example 32

Cleavage of Uracil and AP Site Substrates by Variant Endonucleases

Uracil endonuclease activity of Tma endo V mutants were assessed using A/U, G/U, and T/U substrates. D43A, D110A, and E89A were inactive toward any of the uracil substrates, which is consistent with the proposed metal binding role (FIGS. 26A–C). D105A, which showed wild-type activity towards various inosine substrates, maintained essentially wild-type activity with uracil-containing substrates. H125A cleaved the G/U and T/U substrates as well as the wild-type enzyme (FIGS. 26B–C); however, it had reduced activity against the perfectly base-paired substrate A/U (FIG. 26A). Y80A had minimal uracil cleavage activity. R88A, H116A, and K139A exhibited reduced uracil cleavage. The degree of uracil cleavage by these three mutants appeared to be affected by the nature of the base-pair. When the substrate contained a Watson-Crick base-pair such as A/U (FIG. 26A), the uracil cleavage activity was lowest. When the substrate contained a mismatch such as G/U or T/U, the uracil cleavage activity was enhanced (FIGS. 26B–C). These results are in keeping with the previous time course analysis of the wt enzyme using A/U and T/U substrates (Huang, J., et al., Biochemistry 40(30):8738–48 (2001), which is hereby incorporated by reference in its entirety), suggesting that a uracil in a locally distorted mismatch environment provides a better signal for base recognition.

AP endonuclease activity of Tma endo V mutants was assessed using the A/AP substrate. E. coli endonuclease IV is a thermostable 5' AP endonuclease (Ljungquist, S., J Biol Chem 252(9):p 2808–04 (1977), which is hereby incorporated by reference in its entirety). To prevent the interference of the host AP endonuclease, the wt and mutant endo V were further purified by HiTrap SP column chromatography (Amersham Pharmacia Biotech). Using column purified mutant proteins, AP endonuclease activity was only observed with D105A and H125A (FIG. 26D), both of which had consistently showed wt DNA cleavage activities towards other substrates. Under the 65° C. assay conditions, the AP substrate underwent spontanous cleavage, generating a weak background as seen in the control lane (FIG. 26D). Some marginal AP endonuclease activity may be associated with H116A, but all other mutants abrogated AP cleavage.

Figure 26:
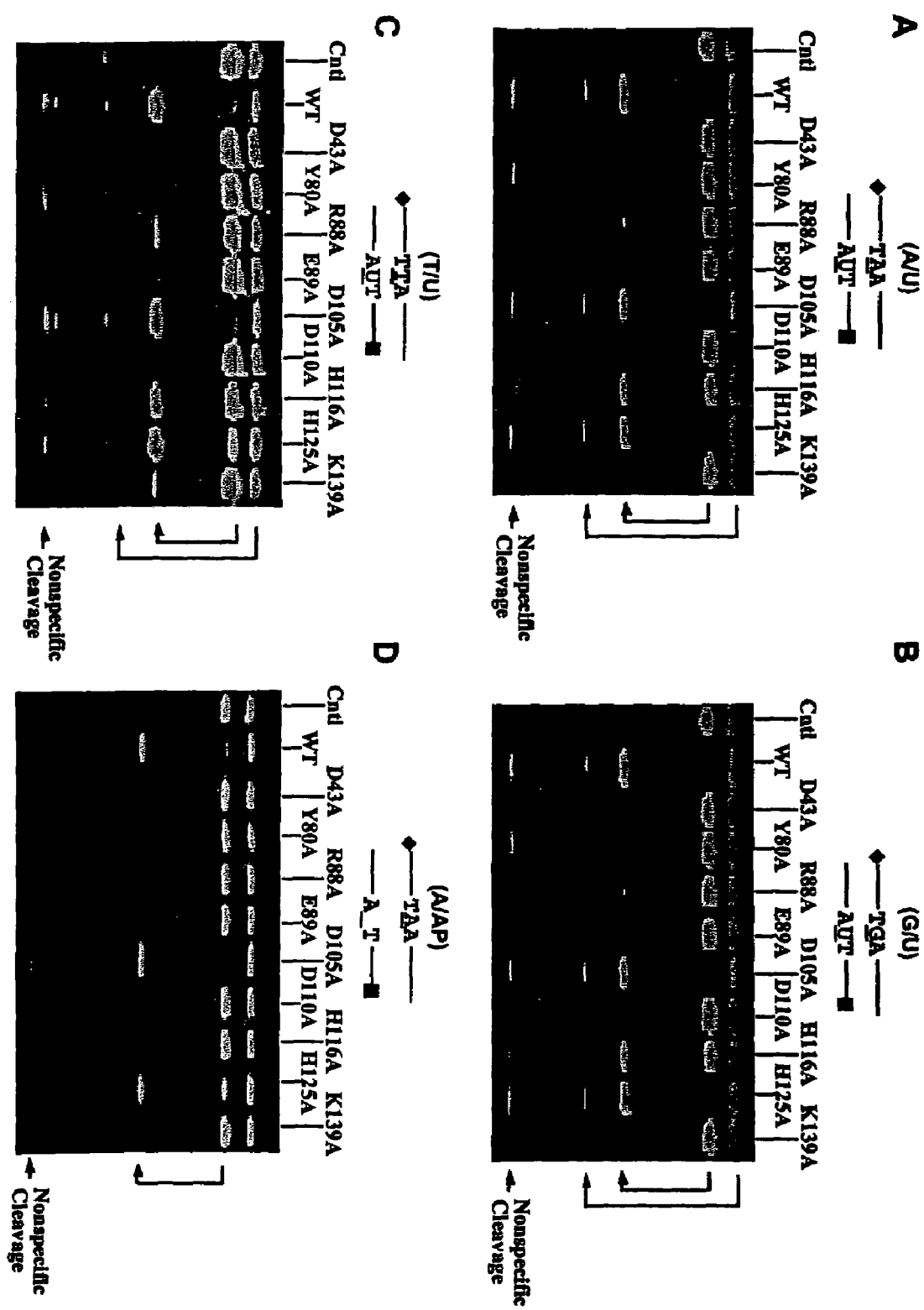
FIGS. 26A–D show cleavage activities of Tma endo V mutants on uracil and AP site substrates. The cleavage reactions were performed with E:S (enzyme:substrate) ratio of 10:1 (S=10 nM) in the presence of 5 mM MgCl$_2$. Cntl: substrate control.

Metal binding and active site (D43, D110, E89) One of the significant findings from this study is identification of amino acid residues involved in metal binding and catalysis. It is known from biochemical studies that endonuclease V is a metal-dependent DNA endonuclease (Huang, J., et al., Biochemistry 40(30):8738–48 (2001) and Yao, M., et al., J. Biol Chem 269(23):16260–08 (1994), which are hereby incorporated by reference in their entirety). The enzyme is most active with $Mg^{2+}$ or $Mn^{2+}$ as the metal cofactor. Previous binding studies have demonstrated that a divalent metal ion is not only required for catalysis but also for formation of a stable enzyme-substrate complex (Huang, J., et al., Biochemistry 40(30):8738–48 (2001), which is hereby incorporated by reference in its entirety). For many endonucleases, a few negatively charged amino acid residues, such as Asp and Glu, are involved in metal binding (Cao, W., et al., J Biol Chem 273(49):33002–10 (1998); Kim, D. R., et al., Genes Dev 13(23):3070–80 (1999) and Koval, R. A., et al., Curr Opin Chem Biol 3(5):578–83 (1999), which are hereby incorporated by reference in their entirety). Out of four such residues mutated, three of them (D43, D11010, E89) appear important for coordinating metal ion(s). D43A and D110A abolish the endonuclease activities towards all substrates tested, which include double-stranded and single-stranded inosine substrates (FIG. 21) and double-stranded uracil and AP site substrates (FIG. 26). E89A had substantially reduced catalytic activities. However, all three mutants retain wild-type binding affinity towards inosine substrates, indicating their important role in catalysis. Most interestingly, D43A and D110A, and in some case E89A, bind to inosine substrates in the absence of a metal ion. D83A and E98A in restriction endonuclease MunI have shown a similar binding behavior (Laugnavicius, A., et al., Biochemistry 36(37):11086–92 (1997), which is hereby incorporated by refernce in its entirety). More recently, the MunI crystal structure complexed with cognate DNA positions D83A and E98A at the active site (Deibert, M., et al., Embo J 18(21): 5805–16 (1999), which is hereby incorporated by reference in its entirety). It is likely that D43 and D110 in Tma endo V, and possibly E89, are involved in binding catalytic metal(s) for the hydrolysis of the scissile phosphate bond. $Ca^{2+}$ competition has been used as a probe to assess the numbers of metal ions involved in DNA cleavage by EcoRV (Cao, W., et al., Biochim Biophys Acta 1546(1):253–60 (2001) and Vipond, I.B., et al., Biochemistry 34(2):697–704 (1995), which are hereby incorporated by reference in their entirety). A stimulatory effect by $Ca^{2+}$ on cognate site cleavage has been taken as an indication of two-metal catalytic mechanism. No enhancement of inosine cleavage was observed in $Ca^{2+}$—$Mg^{2+}$ competition. Thus, the number of metal ions involved in strand cleavage in endonuclease V remains to be determined.

Y80 Alanine substitution at Y80 substantially reduced the affinity of endo V to the double- and single-stranded inosine substrate (FIGS. 22 and 25), as well as the nicked inosine product (FIG. 23). Evidently, weak binding helps endo V dissociate from the product, thereby allowing rapid turnover of the inosine substrate (FIG. 24). The loss of AP endonuclease and uracil endonuclease activities may also be attributed to a weaker binding affinity (FIG. 26). These results suggest that Y80 plays an important role in maintaining a stable complex between the enzyme and the repair-intermediate. Y80 may play such a role by making direct contact to the substrate and the product through base contact or phosphate backbone interaction, or by organizing a network of contacts mediated by other amino acid residues. The kinetic property of accelerated product release is analogous to R177A in human AP endonuclease APE1 (Mol, C. D., et al., Nature 403(6768):451–56 (2000), which is hereby incorporated by reference in its entirety). In a DNA-bound structure, R177 makes a direct contact to the 3' phosphate at the AP site to lock APE1 onto the AP site (Mol, C. D., et al., Nature 403(6768):451–56 (2000), which is hereby incorporated by reference in its entirety). Thus, a phosphate backbone contact may contribute to tight product binding.

Figure 24:
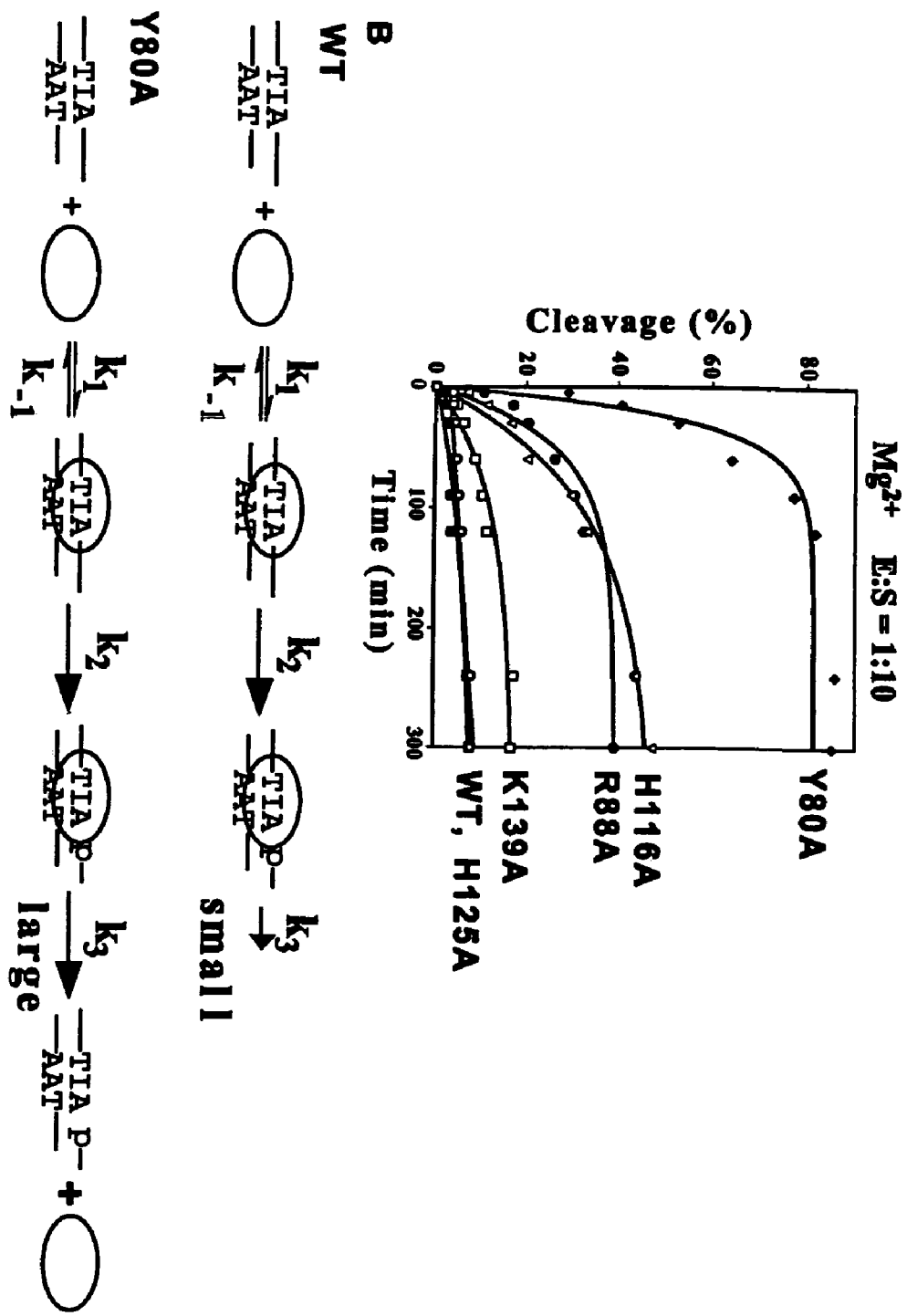
FIGS. 24A–B show a time-course analysis of inosine cleavage by Tma endo V mutants. The cleavage reactions were performed with E:S (enzyme: substrate) ratio of 1:10 (S=10 nM) in the presence of 5 mM $MgCl_2$. Reactions were terminated at specific time points for GeneScan analysis. Oval: Tma endo V.
Figure 25:
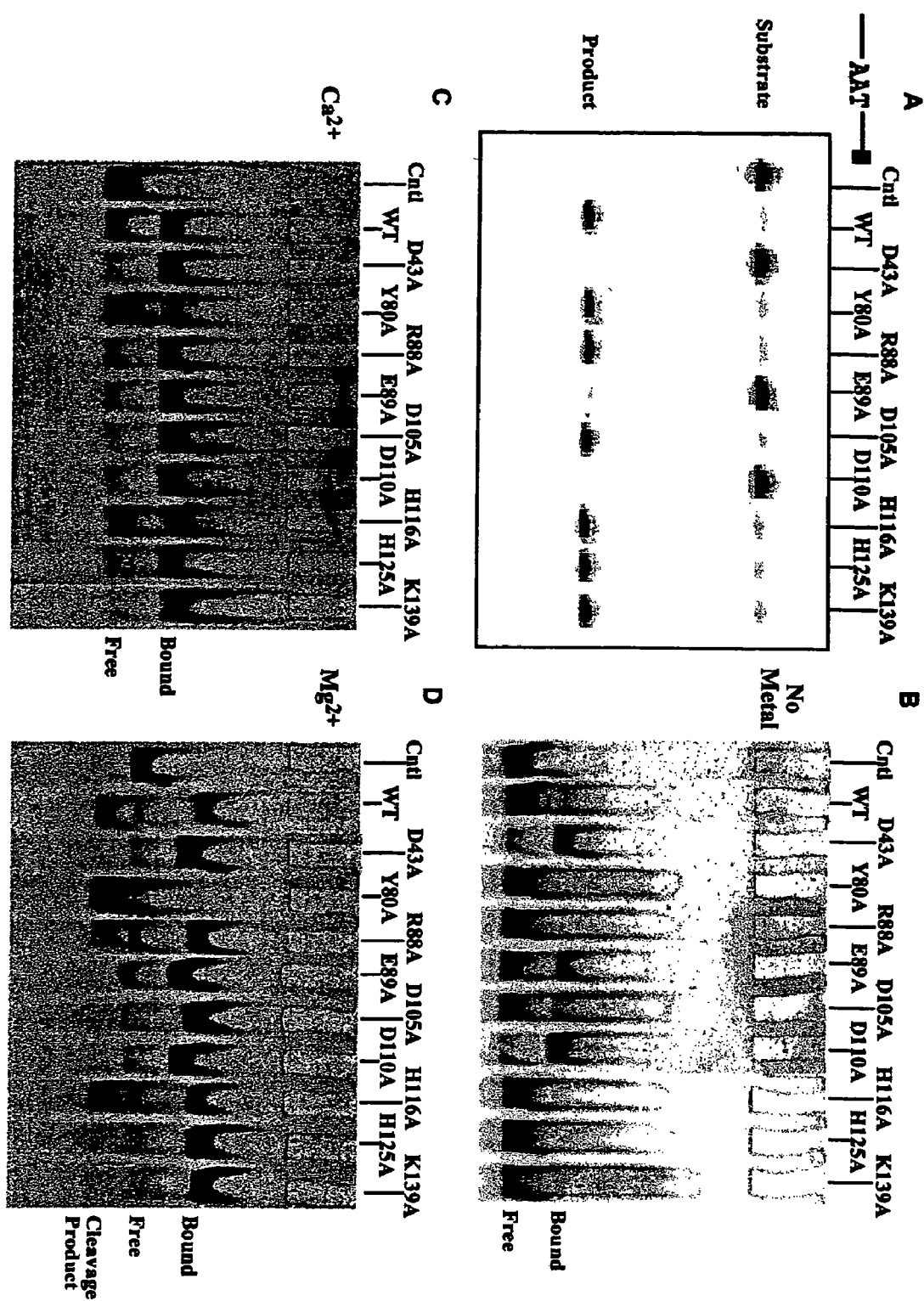
FIGS. 25A–D show the binding and cleavage of single-stranded inosine substrate. Cntl: substrate control.

R88 and H116 R88A and H116A exhibit similar properties. Both of these variants have reduced affinity to the double-stranded inosine substrate and nicked product (FIGS. 22–23), which results in a higher turnover (FIG. 24). They maintain wt level single-stranded inosine cleavage activity (FIG. 25). The major difference between R88A and H116A is at uracil substrates. H116A is about 9-fold more active than R88A for G/U substrate and 5-fold more active for T/U substrate (FIG. 26). Apparently, R88 plays a more important role in uracil recognition.

Figure 21:
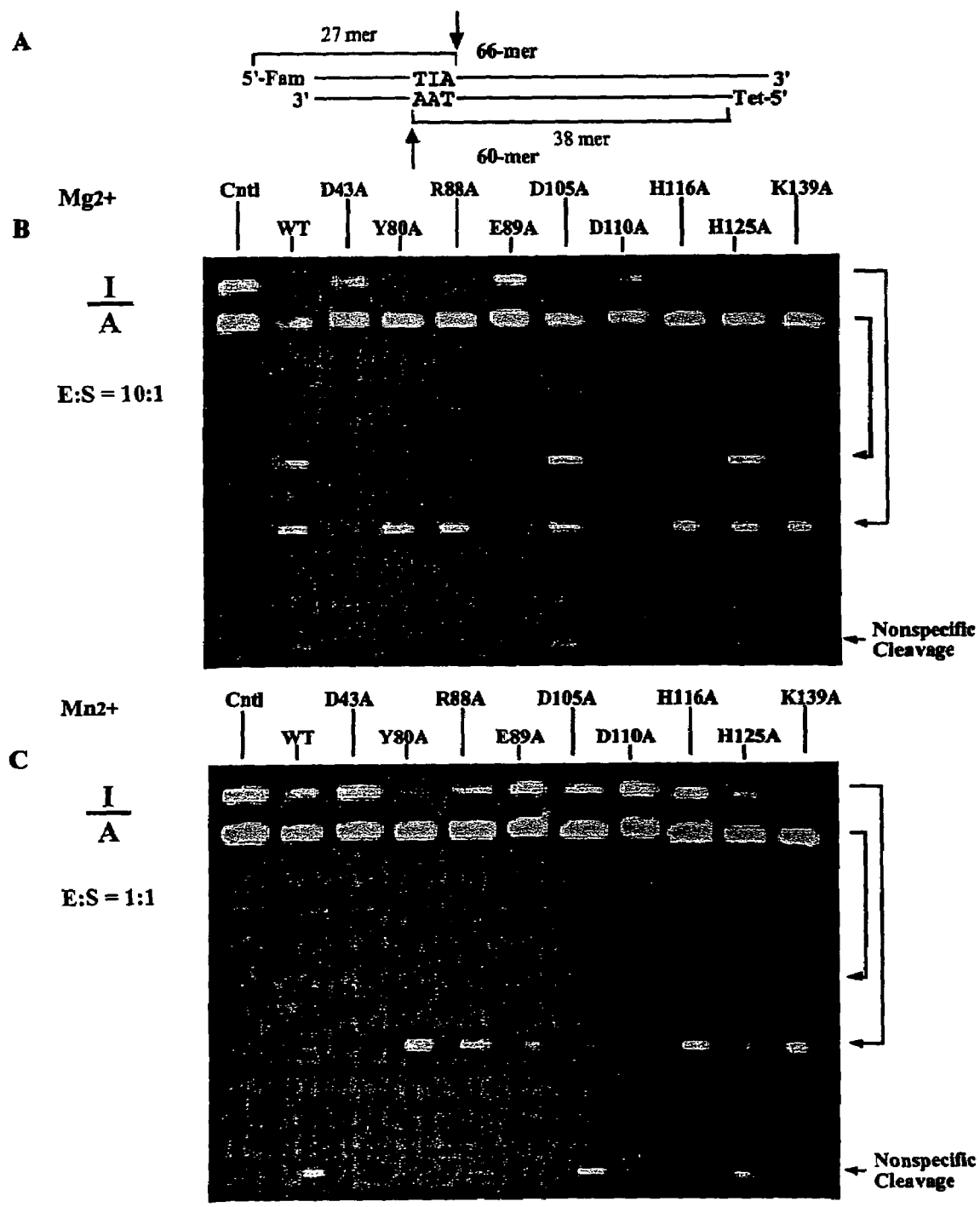
FIGS. 21A–C show cleavage activities of Tma endonuclease V mutants on a double-stranded inosine-containing substrate (I/A). The inosine-containing strand (top strand) is Fam labeled and the opposite strand (bottom strand) is Tet labeled. Cntl: substrate control (FIG. 21A).
Figure 22:
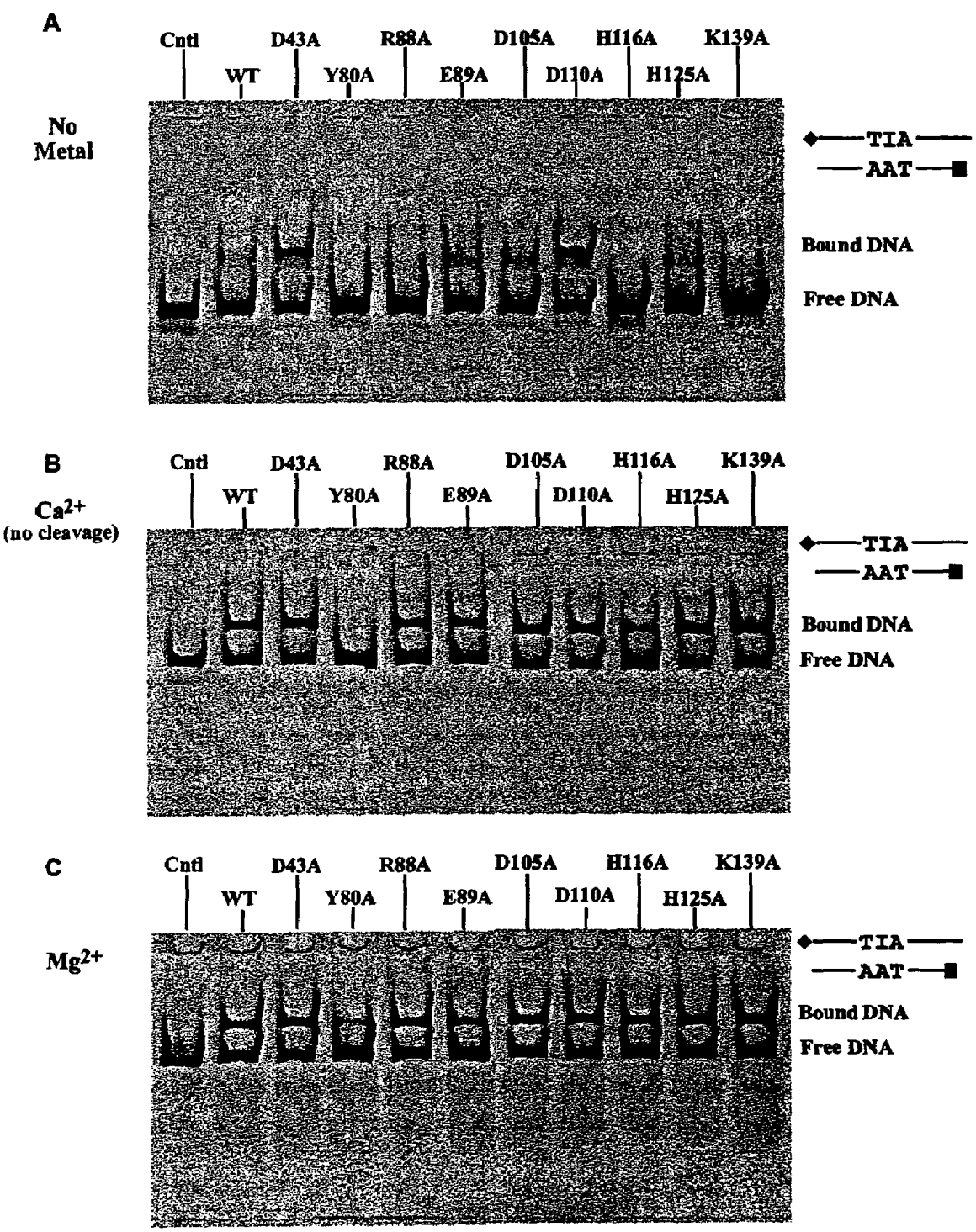
FIGS. 22A–C show gel mobility shift of Tma endonuclease V mutants. Cntl: substrate control.
Figure 23:
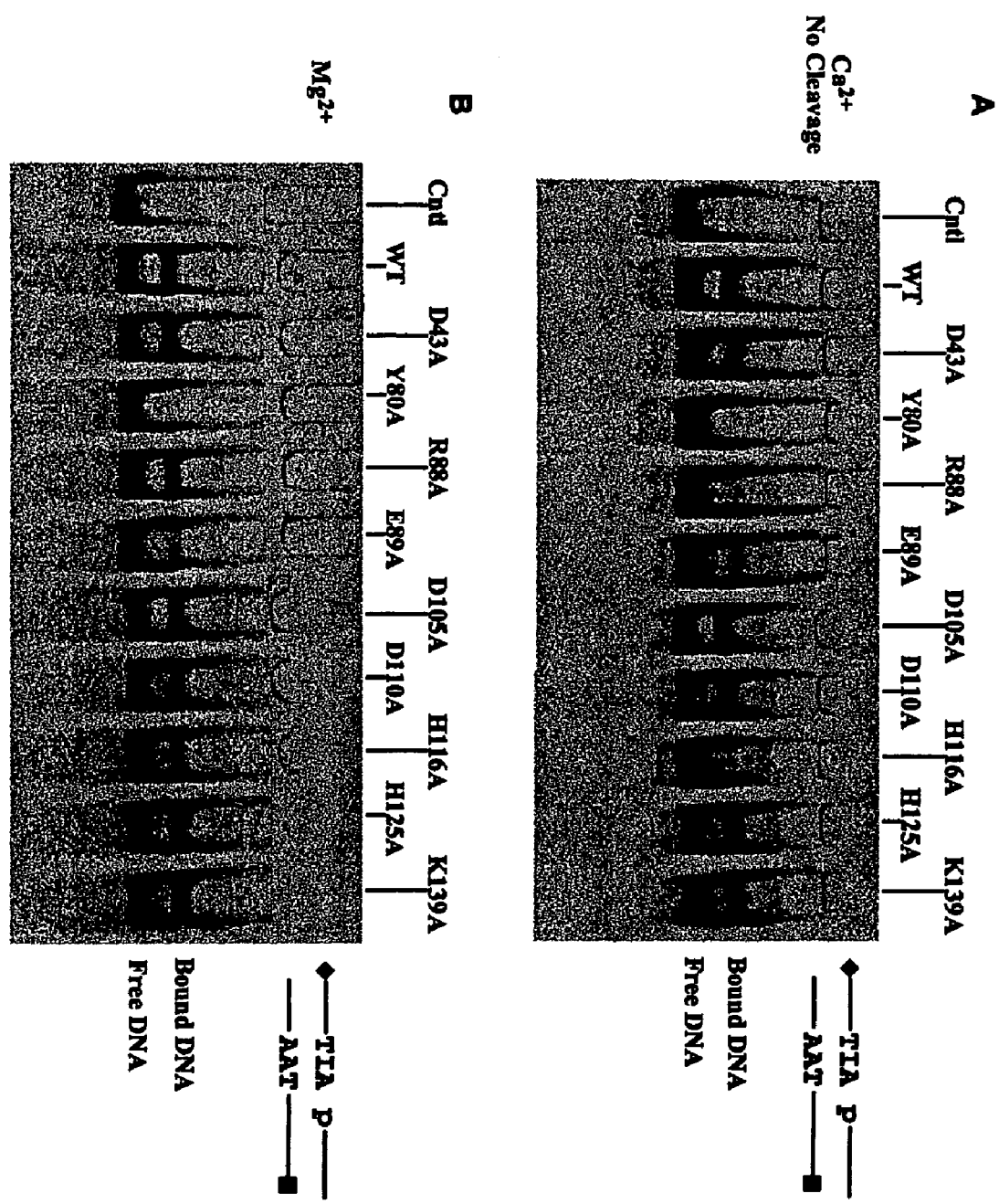
FIGS. 23A–B show gel mobility shift of Tma endonuclease V mutants with nicked inosine product. Cntl: substrate control.

K139 Alanine substitution at K139 has little effect on binding (FIGS. 22–23, 25). K139A maintains wt level cleavage activity toward the double-stranded inosine substrate I/A (FIG. 21). Similar to the wt enzyme, K139A remains bound even after cleaving inosine substrate due to tight product binding (FIG. 24). The main effects of K139A substitution on endo V is at cleavage of non-inosine substrates. In addition to lack of AP endonuclease activity, K139A has a substantially reduced uracil endonuclease activity (FIG. 26). A more detailed kinetic analysis is required to understand the precise catalytic role K139 may play with different substrates.

As the first step to elucidate the structural basis of endonuclease V catalytic and recognition mechanism, an alanine scanning mutagenesis was carried out at nine conserved positions of Tma endonuclease V. D43 and D110, along with E89 may coordinate metal ion(s) for the scissile phosphate bond hydrolysis and are part of the active site. Y80 makes substantial contribution to substrate and nicked product binding. While the lack of strong binding to substrate may account for loss of AP site and uracil cleavage activity, this same property also changes the kinetics of cleaving inosine-containing substrates, such that the product release step is no longer rate limiting. R88A and H116A affect binding steps as well, resulting in diminishing endonuclease activities toward non-inosine substrates. The tight binding by K139A limits the turnover of inosine substrates. The lack of AP site and uracil cleavage suggests that K139A may affect steps other than substrate or product binding. A fill understanding of the mutational effects described here awaits determination of the endo V-DNA complex structure.

Generation of additional Tma endonuclease V mutants at the above mentioned positions revealed four of these variants (R88Q, R88E, H116Q, and H116T) which preferentially nicked or cleaved at least one heteroduplexed DNA containing mismatched bases better than wild-type enzyme in selected buffer conditions. The R88Q and R88E enzymes demonstrated a stronger preference for cleaving the G base in both G:A and A:G mismatched substrate than wild-type endonuclease. The H116Q and H116T enzymes exhibited almost exclusive activity towards "A" base containing substrates. There was almost no activity towards the "G" containing strand, suggesting these variant enzymes are proof of principle that stronger enzymes for specific mismatched sequences can be developed. Such enzymes will improve signal-to-noise in scoring of unknown mutations and polymorphisms, both in pooling experiments, and for mutations in difficult sequence environments.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed is:

1. A method for identifying a mutant nucleic acid sequence differing by one or more single-base changes, insertions, or deletions, from a normal target nucleotide sequences, said method comprising:

providing a sample potentially containing the normal target nucleotide sequence as well as the mutant nucleic acid sequence;

providing two labeled oligonucleotide primers suitable for hybridization on complementary strands of the target nucleotide sequence and the mutant nucleic acid sequence;

providing a polymerase;

blending the sample, the labeled oligonucleotide primers, and the polymerase to form a polymerase chain reaction mixture;

subjecting the polymerase chain reaction mixture to one or more polymerase chain reaction cycles comprising a hybridization treatment, wherein oligonucleotide primers hybridize to the target nucleotide sequence and/or the mutant nucleic acid sequence, an extension treatment, wherein the hybridized oligonucleotide primer is extended to form an extension product complementary to the target nucleotide sequence and/or the mutant nucleic acid sequence to which the oligonucleotide primer is hybridized, and a denaturation treatment, wherein hybridized nucleic acid sequences are separated;

inactivating the polymerase;

denaturing the polymerase chain reaction extension products;

annealing the polymerase chain reaction extension products to form heteroduplexed products potentially containing the normal target nucleotide sequence and the mutant nucleic acid sequence;

providing an endonuclease which preferentially nicks or cleaves heteroduplexed DNA at a location one base away from mismatched base pairs;

blending the heteroduplexed products and the endonuclease to form an endonuclease cleavage reaction mixture;

incubating the endonuclease cleavage reaction mixture so that the endonuclease preferentially nicks or cleaves heteroduplexed products at a location one base away from mismatched base pairs;

providing a ligase;

blending the potentially nicked or cleaved heteroduplexed products and the ligase to form a ligase resealing reaction mixture;

incubating the ligase resealing reaction mixture to seal the nicked heteroduplexed products at perfectly matched base pairs but with substantially no resealing of nicked heteroduplexed products at locations adjacent to mismatched base pairs;

separating products resulting from said incubating the ligase resealing reaction mixture by size or electrophoretic mobility; and detecting the presence of the normal target nucleotide sequence and the mutant nucleic acid sequence in the sample by distinguishing the separated products resulting from said incubating the ligase resealing reaction mixture.

2. A method according to claim 1, wherein the target nucleotide sequence is genomic DNA.

3. A method according to claim 1, wherein the target nucleotide sequence is isolated from tumor samples.

4. A method according to claim 1, wherein the target nucleotide sequence is a double stranded cDNA copy of mRNA.

5. A method according to claim 1, wherein the target nucleotide sequence is a PCR amplified fragment.

6. A method according to claim 1, wherein the two labeled oligonucleotide primers are labeled with fluorescent dyes, IR dyes, or radioactive groups.

7. A method according to claim 6, wherein the two labeled oligonucleotide primers are labeled at their 5' ends.

8. A method according to claim 1, wherein the polymerase is either a native or recombinant thermostable polymerase from *Thermus aquaticus, Thermus thermophilus, Pyrococcus furiosus,* or *Thermotoga maritima*.

9. A method according to claim 1, wherein the polymerase chain reaction is initiated by adding either the polymerase or metal co-factors at temperatures above 65° C. to the polymerase chain reaction mixture.

10. A method according to claim 1, wherein said denaturing the polymerase chain reaction extension products is carried out by heating to a temperature of 80–105° C.

11. A method according to claim 1, wherein said annealing the polymerase chain reaction extension products is carried out by cooling first to a temperature of 20–85° C. and then to room temperature.

12. A method according to claim 1, wherein the endonuclease is Endonuclease V from *Thermotoga maritima*.

13. A method according to claim 1, wherein the endonuclease nicks or cleaves heteroduplexed products at a location 3' from mismatched base pairs.

14. A method according to claim 1, wherein said incubating the ligase resealing reaction mixture is carried out at a pH value between 7.2 and 7.8 when measured at 25° C.

15. A method according to claim 1, wherein the endonuclease cleavage reaction mixture further comprises $MgCl_2$ at a concentration of 2–7 mM.

16. A method according to claim 15, wherein the endonuclease to heteroduplexed product ratio in the endonuclease cleavage reaction mixture is in a range of 10:1 to 100:1.

17. A method according to claim 15, wherein the endonuclease cleavage reaction mixture contains substantially no NaCl or KCl.

18. A method according to claim 1, wherein the endonuclease cleavage reaction mixture further comprises $MnCl_2$ at a concentration of 0.4–1.2 mM.

19. A method according to claim 18, wherein the endonuclease to heteroduplexed product ratio in the endonuclease cleavage reaction mixture is in a range of 1:1 to 1:10.

20. A method according to claim 18, wherein the endonuclease cleavage reaction mixture comprises 50–100 mM NaCl or KCl.

21. A method according to claim 1, wherein the endonuclease cleavage reaction mixture contains DMSO in a range of 2.5 to 10 volume %.

22. A method according to claim 1, wherein the endonuclease cleavage reaction mixture contains betaine in a concentration of 0.5M to 1.5M.

23. A method according to claim 1, wherein said incubating the endonuclease cleavage reaction mixture is carried out at 50–65° C.

24. A method according to claim 1, wherein the ligase is a thermostable ligase.

25. A method according to claim 24, wherein the ligase is from *Thermus* species AK16D.

26. A method according to claim 24, wherein the ligase is from *Thermus aquaticus, Thermus thermophilus, Pyrococcus furiosus,* or *Thermotoga maritima.*

27. A method according to claim 24, wherein the ligase resealing reaction mixture contains 50–150 mM KCl to inhibit further endonucleolytic cleavage.

28. A method according to claim 1, wherein said separating is carried out by using denaturing polyacrylamide gel electrophoresis.

29. A method according to claim 1, wherein said separating is carried out by using capillary gel electrophoresis.

30. A method according to claim 1, wherein the ratio of the mutant nucleic acid sequence to the normal target nucleotide sequence is in a range of 1:20 to 20:1.

31. A method according to claim 1, wherein the polymerase chain reaction extension products have a length in the range of 50 bp to 1,700 bp.

32. A method according to claim 1, wherein the endonuclease preferentially cleaves mismatches within the heteroduplexed products selected from the group consisting of A/A, G/G, T/T, A/G, A/C, G/A, G/T, T/G, T/C, C/A, and C/T.

33. A method according to claim 1, wherein the endonuclease preferentially nicks or cleaves at least one of the heteroduplexed products formed for any single base mutation or polymorphism, except those having a sequence selected from the group consisting of gRcg, rcRc, cgYc and gYgy, where the position of the mismatch is underlined and shown in upper case.

34. A method according to claim 1, wherein the endonuclease preferentially nicks or cleaves one, two, and three base insertions or deletions within the heteroduplexed products.

35. A method according to claim 1, wherein said method distinguishes an inherited or sporadic mutation or polymorphism from a polymorphism in the normal target sequence.

36. A method according to claim 1, wherein the inherited or sporadic mutation or polymorphism is distinguished in a tumor suppressor gene, oncogene, or DNA replication or repair gene.

37. A method according to claim 36, wherein the gene is selected from the group consisting of Bcl2, Mdm2, Cdc25A, Cyclin D1, Cyclin E1, Cdk4, survivin, HSP27, HSP70, p53, $p21^{Cip}$, $p16^{Ink4a}$, $p19^{ARF}$, $p15^{INK4b}$, $p27^{Kip}$, Bax, growth factors, EGFR, Her2-neu, ErbB-3, ErbB-4, c-Met, c-Sea, Ron, c-Ret, NGFR, TrkB, TrkC, IGF1R, CSF1R, CSF2, c-Kit, AXL, Flt-1 (VEGFR-1), Flk-1 (VEGFR-2), PDGFRα, PDGFRβ, FGFR-1, FGFR-2, FGFR-3, FGFR-4, other protein tyrosine kinase receptors, β-catenin, Wnt(s), Akt, Tcf4, c-Myc, n-Myc, Wisp-1, Wisp-3, K-ras, H-ras, N-ras, c-Jun, c-Fos, PI3K, c-Src, Shc, Raf1, TGFβ, and MEK, E-Cadherin, APC, TβRII, Smad2, Smad4, Smad 7, PTEN, VHL, BRCA1, BRCA2, ATM, hMSH2, hMLH1, hPMS1, hPMS2, and hMSH3.

38. A method according to claim 1, wherein the endonuclease is a thermostable endonuclease which preferentially nicks or cleaves heteroduplexed DNA at a location where base pairs are mismatched or one base beyond the mismatch and generates ends which are suitable for ligation when nicking perfectly matched DNA.

39. A method according to claim 1, wherein the endonuclease is a thermostable endonuclease which preferentially nicks or cleaves heteroduplexed DNA at A/A, G/G, T/T, A/G, A/C, G/A, G/T, T/G, T/C, C/A, or C/T mismatched base pairs at a location where the base pairs are mismatched or one base beyond the mismatch and generates ends which are suitable for ligation when nicking perfectly matched DNA.

40. A method according to claim 1, wherein the endonuclease is a thermostable endonuclease which preferentially nicks or cleaves at least one heteroduplex formed for any single base mutation or polymorphism, except those having gRcg, rcRc, cgYc, or gYgy sequences, where the position of the mismatch is underlined and shown in upper case, and generates ends which are suitable for ligation when nicking perfectly matched DNA.

41. A method according to claim 1, wherein the endonuclease is a thermostable endonuclease which preferentially nicks or cleaves heteroduplexed DNA containing one, two, and three base insertions or deletions, at a location where the base pairs are mismatched or one base beyond the unpaired bases, and generates ends which are suitable for ligation when nicking DNA at perfect matched DNA.

42. A method for identifying a mutant nucleic sequence differing by one or more single-base changes, insertions, or deletions from a normal target nucleic acid sequence, said method comprising:

providing a sample potentially containing the mutant nucleic acid sequence but not necessarily the normal target nucleic acid sequence;

providing a standard containing the normal target nucleic acid sequence;

providing two labeled oligonucleotide primers suitable for hybridization on complementary strands of the mutant nucleic acid sequence;

providing a polymerase;

blending the sample, the standard, the labeled oligonucleotide primers, and the polymerase to form a first polymerase chain reaction mixture;

subjecting the first polymerase chain reaction mixture to one or more polymerase chain reaction cycles comprising a hybridization treatment, wherein the labeled oligonucleotide primers hybridize to the mutant nucleic acid sequence, an extension treatment, wherein the hybridized oligonucleotide primer is extended to form an extension product complementary to the mutant nucleic acid sequence to which the oligonucleotide primer is hybridized, and a denaturation treatment, wherein hybridized nucleic acid sequences are separated;

inactivating the polymerase;

providing the normal target nucleic acid sequence;

blending the normal target nucleic acid sequence, the labeled oligonucleotide primers, and the polymerase to form a second polymerase chain reaction mixture;

subjecting the second polymerase chain reaction mixture to one or more polymerase chain reaction cycles comprising a hybridization treatment, wherein the labeled oligonucleotide primers hybridize to the normal target nucleic acid sequence, an extension treatment, wherein the hybridized oligonucleotide primer is extended to form an extension product complementary to the normal target nucleic acid sequence to which the oligonucleotide primer is hybridized, and a denaturation treatment, wherein hybridized nucleic acid sequences are separated;

inactivating the polymerase;

blending the first and second polymerase chain reaction extension products;

denaturing the first and second polymerase chain reaction extension products;

annealing the first and second polymerase chain reaction extension products to form heteroduplexed products potentially containing the normal target nucleic acid sequence and the mutant nucleic acid sequence;

providing an endonuclease which preferentially nicks or cleaves heteroduplexed DNA at a location one base away from mismatched base pairs;

blending the heteroduplexed products and the endonuclease to form an endonuclease cleavage reaction mixture;

incubating the endonuclease cleavage reaction mixture so that the endonuclease preferentially nicks or cleaves heteroduplexed products at a location one base away from mismatched base pairs;

providing a ligase;

blending the potentially nicked or cleaved heteroduplexed products and the ligase to form a ligase resealing reaction mixture;

incubating the ligase resealing reaction mixture to seal the nicked heteroduplexed products at perfectly matched base pairs but with substantially no resealing of nicked heteroduplexed products at locations adjacent to mismatched base pairs;

separating products resulting from said incubating the ligase resealing reaction mixture by size or electrophoretic mobility; and detecting the presence of the normal target nucleic acid sequence and the mutant nucleic acid sequence target nucleotide in the sample by distinguishing the separated products resulting from said incubating the ligase resealing reaction mixture.

43. A method according to claim 42, wherein the target nucleotide sequence is genomic DNA.

44. A method according to claim 42, wherein the target nucleotide sequence is isolated from tumor samples.

45. A method according to claim 42, wherein the target nucleotide sequence is a double stranded cDNA copy of mRNA.

46. A method according to claim 42, wherein the target nucleotide sequence is a PCR amplified fragment.

47. A method according to claim 42, wherein the two labeled oligonucleotide primers are labeled with fluorescent dyes, IR dyes, or radioactive groups.

48. A method according to claim 47, wherein the two labeled oligonucleotide primers are labeled at their 5' ends.

49. A method according to claim 42, wherein the polymerase is either a native or recombinant thermostable polymerase from *Thermus aquaticus, Thermus thermophilus, Pyrococcus furiosus*, or *Thermotoga maritima*.

50. A method according to claim 42, wherein the polymerase chain reaction is initiated by adding either the polymerase or metal co-factors at temperatures 65–94° C. to the polymerase chain reaction mixture.

51. A method according to claim 42, wherein said denaturing the polymerase chain reaction extension products is carried out by heating to a temperature above 94° C.

52. A method according to claim 42, wherein said annealing the polymerase chain reaction extension products is carried out by cooling first to 50–85° C. and then to room temperature.

53. A method according to claim 42, wherein the endonuclease is Endonuclease V from *Thermotoga maritima*.

54. A method according to claim 42, wherein the endonuclease nicks or cleaves heteroduplexed products at a location on the 3' side one base away from mismatched base pairs.

55. A method according to claim 42, wherein said incubating the ligase resealing reaction mixture is carried out at a pH value between 7.2 and 7.8 when measured at 25° C.

56. A method according to claim 42, wherein the endonuclease cleavage reaction mixture further comprises $MgCl_2$ at a concentration of 2–7 mM.

57. A method according to claim 56, wherein the endonuclease to heteroduplexed product ratio in the endonuclease cleavage reaction mixture is in a range of 10:1 to 100:1.

58. A method according to claim 56, wherein the endonuclease cleavage reaction mixture contains substantially no NaCl or KCl.

59. A method according to claim 42, wherein the endonuclease cleavage reaction mixture further comprises $MnCl_2$ at a concentration of 0.4–1.2 mM.

60. A method according to claim 59, wherein the endonuclease to heteroduplexed product ratio in the endonuclease cleavage reaction mixture is in a range of 1:1 to 1:10.

61. A method according to claim 59, wherein the endonuclease cleavage reaction mixture comprises 25–75 mM NaCl or KCl.

62. A method according to claim 42, wherein the endonuclease cleavage reaction mixture contains DMSO in a range of 2.5% to 10 volume %.

63. A method according to claim 42, wherein the endonuclease cleavage reaction mixture contains betaine in a concentration of 0.5M to 1.5M.

64. A method according to claim 42, wherein said incubating the endonuclease cleavage reaction mixture is carried out at 65° C. for 1 hour.

65. A method according to claim 42, wherein the ligase is a thermostable ligase.

66. A method according to claim 65, wherein the ligase is from *Thermus* species AK16D.

67. A method according to claim 65, wherein the ligase is from *Thermus aquaticus, Thermus thermophilus, Pyrococcus furiosus*, or *Thermotoga maritima*.

68. A method according to claim 65, wherein the ligase resealing reaction mixture contains 25–75 mM KCl to inhibit further endonucleolytic cleavage.

69. A method according to claim 42, wherein said separating is carried out by using denaturing polyacrylamide gel electrophoresis.

70. A method according to claim 42, wherein said separating is carried out by using capillary gel electrophoresis.

71. A method according to claim 42, wherein the ratio of the mutant nucleic acid sequence to the normal target nucleotide sequence is in a range of 1:20 to 20:1.

72. A method according to claim 42, wherein the polymerase chain reaction extension products have a length in the range of 50 bp to 1,700 bp.

73. A method according to claim 42, wherein the endonuclease preferentially cleaves mismatches within the heteroduplexed products selected from the group consisting of A/A, G/G, T/T, A/G, A/C, G/A, G/T, T/G, T/C, C/A, and C/T.

74. A method according to claim 42, wherein the endonuclease preferentially nicks or cleaves at least one of the heteroduplexed products formed for any single base mutation or polymorphism, except those having a sequence selected from the group consisting of gRcg, rcRc, cgYc and gYgy, where the position of the mismatch is underlined and shown in upper case.

75. A method according to claim 42, wherein the endonuclease preferentially nicks or cleaves one, two, and three base insertions or deletions within the heteroduplexed products.

76. A method according to claim 42, wherein said method distinguishes an inherited or sporadic mutation or polymorphism from a polymorphism in the normal target sequence.

77. A method according to claim 42, wherein the inherited or sporadic mutation or polymorphism is distinguished in a tumor suppressor gene, oncogene, or DNA replication or repair gene.

78. A method according to claim 77, wherein the gene is selected from the group consisting of Bcl2, Mdm2, Cdc25A, Cyclin D1, Cyclin E1, Cdk4, survivin, HSP27, HSP70, p53, $p21^{Cip}$, $p16^{Ink4a}$, $p19^{ARF}$, $p15^{INK4b}$, $p27^{Kip}$, Bax, growth factors, EGFR, Her2-neu, ErbB-3, ErbB-4, c-Met, c-Sea, Ron, c-Ret, NGFR, TrkB, TrkC, IGF1R, CSF1R, CSF2, c-Kit, AXL, Flt-1 (VEGFR-1), Flk-1 (VEGFR-2), PDGFRα, PDGFRβ, FGFR-1, FGFR-2, FGFR-3, FGFR-4, other protein tyrosine kinase receptors, β-catenin, Wnt(s), Akt, Tcf4, c-Myc, n-Myc, Wisp-1, Wisp-3, K-ras, H-ras, N-ras, c-Jun, c-Fos, PI3K, c-Src, Shc, Raf1, TGFβ, and MEK, E-Cadherin, APC, TβRII, Smad2, Smad4, Smad 7, PTEN, VHL, BRCA1, BRCA2, ATM, hMSH2, hMLH1, hPMS1, hPMS2, and hMSH3.

79. A method according to claim 42, wherein the endonuclease is a thermostable endonuclease which preferentially nicks or cleaves heteroduplexed DNA at a location where base pairs are mismatched or one base beyond the mismatch and generates ends which are suitable for ligation when nicking perfectly matched DNA.

80. A method according to claim 42, wherein the endonuclease is a thermostable endonuclease which preferentially nicks or cleaves heteroduplexed DNA at A/A, G/G, T/T, A/G, A/C, G/A, G/T, T/G, T/C, C/A, or C/T mismatched base pairs at a location where the base pairs are mismatched or one base beyond the mismatch and generates ends which are suitable for ligation when nicking perfectly matched DNA.

81. A method according to claim 42, wherein the endonuclease is a thermostable endonuclease which preferentially nicks or cleaves at least one heteroduplex formed for any single base mutation or polymorphism, except those having gRcg, rcRc, cgYc, or gYgy sequences, where the position of the mismatch is underlined and shown in upper case, and generates ends which are suitable for ligation when nicking perfectly matched DNA.

82. A method according to claim 42, wherein the endonuclease is a thermostable endonuclease which preferentially nicks or cleaves heteroduplexed DNA containing one, two, and three base insertions or deletions, at a location where the base pairs are mismatched or one base beyond the unpaired bases, and generates ends which are suitable for ligation when nicking DNA at perfect matched DNA.

83. A method for identifying a mutant nucleic acid sequence differing by one or more single-base changes, insertions, or deletions, from a normal target nucleic acid sequence, said method comprising:

providing a sample potentially containing the normal target nucleic acid sequence as well as the mutant nucleic acid sequence;

providing two labeled oligonucleotide primers suitable for hybridization on complementary strands of the target nucleic acid sequence and the mutant nucleic acid sequence;

providing a polymerase;

blending the sample, the labeled oligonucleotide primers, and the polymerase to form a polymerase chain reaction mixture;

subjecting the polymerase chain reaction mixture to one or more polymerase chain reaction cycles comprising a hybridization treatment, wherein oligonucleotide primers hybridize to the target nucleic acid sequence and/or the mutant nucleic acid sequence, an extension treatment, wherein the hybridized oligonucleotide primer is extended to form an extension product complementary to the target nucleic acid sequence and/or the mutant nucleic acid sequence to which the oligonucleotide primer is hybridized, and a denaturation treatment, wherein hybridized nucleic acid sequences are separated;

inactivating the polymerase;

denaturing the polymerase chain reaction extension products;

annealing the polymerase chain reaction extension products to form heteroduplexed products potentially containing the normal target nucleic acid sequence and the mutant nucleic acid sequence;

providing an endonuclease which preferentially nicks or cleaves heteroduplexed DNA at a location one base away from mismatched base pairs;

blending the heteroduplexed products and the endonuclease to form an endonuclease cleavage reaction mixture;

incubating the endonuclease cleavage reaction mixture so that the endonuclease preferentially nicks or cleaves heteroduplexed products at a location one base away from mismatched base pairs;

providing a ligase;

blending the potentially nicked or cleaved heteroduplexed products and the ligase to form a ligase resealing reaction mixture;

incubating the ligase resealing reaction mixture to seal the nicked heteroduplexed products at perfectly matched base pairs but with substantially no resealing of nicked heteroduplexed products at locations adjacent to mismatched base pairs;

providing a polymerase with 3'-5' exonuclease activity;

blending the potentially nicked or cleaved heteroduplexed products and the polymerase with 3'-5' exonuclease activity to form a polymerase exonucleolytic degradation reaction mixture;

incubating the polymerase exonucleolytic degradation reaction mixture under conditions effective for the 3'-5' exonucleolytic activity to remove several bases 3' to the nick;

inactivating the polymerase with 3'-5' exonuclease activity:

providing a polymerase without 3'-5' activity;

blending the incubated polymerase degradation reaction mixture, the polymerase without 3'-5' activity, labeled dideoxyterminator triphosphate nucleotides, and deoxyribonucleotide triphsophates to form a polymerase mini-sequencing reaction mixture;

incubating the polymerase mini-sequencing reaction mixture under conditions effective for the polymerase without 3'-5' activity to extend the 3' end of the nicked or cleaved heteroduplexed products to form mini-sequencing reaction products;

separating the mini-sequencing products by size or electrophoretic mobility; and detecting the presence of normal target nucleic acid sequence and the mutant nucleic acid sequence by distinguishing the separated mini-sequencing products resulting from said incubating the polymerase mini-sequencing reaction mixture.

* * * * *

UNITED STATES PATENT AND TRADEMARK OFFICE
CERTIFICATE OF CORRECTION

PATENT NO. : 7,198,894 B2
APPLICATION NO. : 09/998481
DATED : April 3, 2007
INVENTOR(S) : Barany et al.

It is certified that error appears in the above-identified patent and that said Letters Patent is hereby corrected as shown below:

Col. 1 at lines 8-11, delete "The present invention arose from research sponsored by the National Institutes of Health under Grant Nos. ROI-CA65930 and ROI-CA 81467. The United States Government may have certain rights." and insert --This invention was made with government support under grants ROI-CA65930 and ROI-CA 81467 awarded by National Institutes of Health. The government has certain rights in the invention-- in its place.

Signed and Sealed this

Seventh Day of April, 2009

JOHN DOLL
*Acting Director of the United States Patent and Trademark Office*

```
                               SEQUENCE LISTING

<160> NUMBER OF SEQ ID NOS: 50

<210> SEQ ID NO 1
<211> LENGTH: 66
<212> TYPE: DNA
<213> ORGANISM: Thermotoga maritima
<220> FEATURE:
<221> NAME/KEY: misc_feature
<222> LOCATION: (26)
<223> OTHER INFORMATION: N at position 26 is inosine

<400> SEQUENCE: 1
taccccagcg tctgcggtgt tgcgtnagtt gtcatagttt gatcctctag tcttgttgcg      60
ggttcc                                                                66

<210> SEQ ID NO 2
<211> LENGTH: 60
<212> TYPE: DNA
<213> ORGANISM: Thermatoga maritima
<220> FEATURE:
<221> NAME/KEY: misc_feature
<222> LOCATION: (24)
<223> OTHER INFORMATION: N at position 24 is inosine

<400> SEQUENCE: 2
ggggtcgcag acgccacaac gcantcaaca gtatcaaact aggagatcag aacaacgccc      60

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence:  Primer
```

```
<400> SEQUENCE: 3
ggagggaatc atatggatta caggcagctt caca                                    34

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence:  Primer

<400> SEQUENCE: 4
gcgcctggat ccactagttc agaaaaggcc tttttgagc cgt                           43

<210> SEQ ID NO 5
<211> LENGTH: 66
<212> TYPE: DNA
<213> ORGANISM: Artificial Sequence
<220> FEATURE:
<223> OTHER INFORMATION: Description of Artificial Sequence:  Synthetic
      substrate
<220> FEATURE:
<221> NAME/KEY: misc_feature
<222> LOCATION: (26)
<223> OTHER INFORMATION: N at position 26 can be a, t, c, or g

<400> SEQUENCE: 5
taccccagcg tctgcggtgt tgcgtnagtt gtcatagttt gatcctctag tcttgttgcg        60
ggttcc                                                                   66

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence:  Synthetic
      substrate
<220> FEATURE:
<221> NAME/KEY: misc_feature
<222> LOCATION: (24)
<223> OTHER INFORMATION: N at position 24 can be a, t, c, or g

<400> SEQUENCE: 6
ggggtcgcag acgccacaac gcantcaaca gtatcaaact aggagatcag aacaacgccc        60

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence:  Primer

<400> SEQUENCE: 7
ccccatagtg tattaacctt atgtgtgaca tgttc                                   35

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence:  Primer

<400> SEQUENCE: 8
ccccaaaatg gtcagagaaa cctttatctg tatc                                    34

<210> SEQ ID NO 9
<211> LENGTH: 27
```

```
<212> TYPE: DNA
<213> ORGANISM: Artificial Sequence
<220> FEATURE:
<223> OTHER INFORMATION: Description of Artificial Sequence: Primer

<400> SEQUENCE: 9
ccccgctgcc acttgcaaag tttcttc                                          27

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 10
ccccactctg aacggagctg gcaat                                            25

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 11
cccctgttca cttgtgccct gactttc                                          27

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 12
cccccagctg ctcaccatcg ctatc                                            25

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 13 cccccctctga ttcctcactg attgctctta                                      30

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 14
cccggccact gacaaccacc cttaac                                           26

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 15
```

-continued cccgcctcat cttgggcctg tgttatc    27

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 16
cccgtggatg ggtagtagta tggaagaaat    30

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 17
cccggacagg taggacctga tttccttac    29

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 18
ccccgcttct tgtcctgctt gcttac    26

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 19
cccgcatggt ggtgcacacc tatagtc    27

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 20
cccaagctgt tccgtcccag tagattac    28

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 21
cccctcattg gaacagaaag aaatggattt atc    33

<210> SEQ ID NO 22
<211> LENGTH: 35
<212> TYPE: DNA
<213> ORGANISM: Artificial Sequence

```
<220> FEATURE:
<223> OTHER INFORMATION: Description of Artificial Sequence:  Primer

<400> SEQUENCE: 22
cccctcttcc ctagtatgta aggtcaattc tgttc                              35

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence:  Primer

<400> SEQUENCE: 23
ccccacttcc attgaaggaa gcttctcttt c                                  31

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence:  Primer

<400> SEQUENCE: 24
ccccatctct gcaaggggga gtggaatac                                     29

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence:  Primer

<400> SEQUENCE: 25
cccccaaaat atgtctggat tggagaaagt ttc                                33

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence:  Primer

<400> SEQUENCE: 26 cccctggaa aagacttgct tggtactatc ttc                                 33

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence:  Primer

<400> SEQUENCE: 27
cccgaccgcg cgcgaagact ac                                            22

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence:  Primer

<400> SEQUENCE: 28 cccagggct tcagaccgtg ctatc                                          25
```

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 29
ccccaccggt gtggctcttt aacaac                                  26

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 30
cccctgacat caggcaaaaa ttgagaa                                 27

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 31
ccctagttgt tggcaaagcc tcttgttc                                28

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 32
cccaaactaa ggaaggaacc agtcctgtat c                            31

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 33
ccccatagtg tattaacctt atgtgtgaca tgttc                        35

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 34
ccccaaaatg gtcagagaaa cctttatctg tatc                         34

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 35
ccccgctgcc acttgcaaag tttcttc					27

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 36
ccccactctg aacggagctg gcaat					25

<210> SEQ ID NO 37
<211> LENGTH: 225
<212> TYPE: PRT
<213> ORGANISM: Thermotoga maritima

<400> SEQUENCE: 37

```
Met Asp Tyr Arg Gln Leu His Arg Trp Asp Leu Pro Pro Asp Glu Ala
 1               5                  10                  15

Ile Lys Val Gln Asn Glu Leu Arg Lys Lys Ile Lys Leu Thr Pro Tyr
            20                  25                  30

Glu Gly Glu Pro Glu Tyr Val Ala Gly Val Asp Leu Ser Phe Pro Gly
        35                  40                  45

Lys Glu Glu Gly Leu Ala Val Ile Val Val Leu Glu Tyr Pro Ser Phe
    50                  55                  60

Lys Ile Leu Glu Val Val Ser Glu Arg Gly Glu Ile Thr Phe Pro Tyr
65                  70                  75                  80

Ile Pro Gly Leu Leu Ala Phe Arg Glu Gly Pro Leu Phe Leu Lys Ala
                85                  90                  95

Trp Glu Lys Leu Arg Thr Lys Pro Asp Val Val Phe Asp Gly Gln
            100                 105                 110

Gly Leu Ala His Pro Arg Lys Leu Gly Ile Ala Ser His Met Gly Leu
        115                 120                 125

Phe Ile Glu Ile Pro Thr Ile Gly Val Ala Lys Ser Arg Leu Tyr Gly
    130                 135                 140

Thr Phe Lys Met Pro Glu Asp Lys Arg Cys Ser Trp Ser Tyr Leu Tyr
145                 150                 155                 160

Asp Gly Glu Glu Ile Ile Gly Cys Val Ile Arg Thr Lys Glu Gly Ser
                165                 170                 175

Ala Pro Ile Phe Val Ser Pro Gly His Leu Met Asp Val Glu Ser Ser
            180                 185                 190

Lys Arg Leu Ile Lys Ala Phe Thr Leu Pro Gly Arg Arg Ile Pro Glu
        195                 200                 205

Pro Thr Arg Leu Ala His Ile Tyr Thr Gln Arg Leu Lys Lys Gly Leu
    210                 215                 220

Phe
225
```

<210> SEQ ID NO 38
<211> LENGTH: 229
<212> TYPE: PRT
<213> ORGANISM: Pyrobaculum aerophilum

<400> SEQUENCE: 38

Met Ala Arg Leu Lys Leu Leu Lys Lys Phe Ser Pro Arg Leu Met Pro

```
              1               5                  10                 15
Pro Ile Asn Ile Glu Ala Ala Arg Arg Ile Gln Glu Arg Leu Ala Arg
                    20                  25                  30

Gln Val Thr Tyr Ala Pro Leu Pro Val Glu Thr Val Ala Gly Leu
            35                  40                  45

Asp Val Ala Tyr Ser Gly Ser Leu Ala Phe Gly Ala Ala Val Val Val
        50                  55                  60

Lys Arg Thr Thr Leu Glu Val Val Glu Thr Ala Cys Ser Val Ser Arg
65                  70                  75                  80

Ile Val Val Pro Tyr Val Pro Thr Phe Leu Ala Phe Arg Glu Leu Thr
                85                  90                  95

Pro Met Leu Arg Ala Tyr Ile Lys Leu Lys Ser Lys Pro Asp Val Ile
                100                 105                 110

Leu Val Asp Gly His Gly Val Ala His Pro Arg Arg Phe Gly Ile Ala
            115                 120                 125

Ser His Ile Gly Val Val Leu Lys Lys Pro Thr Ile Gly Val Ala Lys
        130                 135                 140

Ser Arg Leu Tyr Gly Glu Val Gly Asp Lys Leu Val Asp Pro Ala
145                 150                 155                 160

Thr Gly Glu Val Leu Ala Leu Ile Ile Lys Cys Gly Gly Lys Lys Tyr
                165                 170                 175

Val Ser Val Gly Ser Tyr Ala Thr Leu Asp Glu Ala Ala Gly Leu Val
                180                 185                 190

Ala Gln Leu Cys Lys Ser Gly Asp Val Tyr Pro Leu Arg Leu Ala His
            195                 200                 205

Glu Leu Ala Asn Lys Leu Lys Lys Ala His Leu Pro Asp Asp Lys Asp
        210                 215                 220

Arg Asp Ser Cys Pro
225

<210> SEQ ID NO 39
<211> LENGTH: 211
<212> TYPE: PRT
<213> ORGANISM: Pyrococcus horikoshii

<400> SEQUENCE: 39

Met Leu Glu Arg Ile Ala Asn Ile Gln Lys Lys Leu Ser Lys Ser Ile
1               5                   10                  15

Val Glu Arg Lys Ile Asn Glu Val Arg Lys Val Ala Ala Val Asp Val
                20                  25                  30

Ser Tyr Lys Glu Lys Ala Arg Ala Ala Leu Val Ile Thr Thr Phe
            35                  40                  45

Pro Glu Gly Glu Val Leu Lys Thr Lys Val Ile Glu Thr Thr Val Ser
        50                  55                  60

Phe Pro Tyr Ile Pro Thr Phe Phe Leu Arg Glu Thr Lys Pro Ile
65                  70                  75                  80

Leu Ile Ala Thr Lys Gly Glu Thr Phe Asp Val Leu Ile Val Glu Gly
                85                  90                  95

His Gly Lys Ala His Pro Arg Gly Tyr Gly Leu Ala Ser His Ile Gly
                100                 105                 110

Val Val Leu Arg Lys Pro Thr Ile Gly Val Ala Lys Arg Leu Leu Lys
            115                 120                 125

Asn Thr Pro Lys Asp Thr Tyr Lys Lys Val Gly Lys Val Tyr Val Ser
        130                 135                 140
```

-continued

```
Val Gly Asn Leu Ile Thr Leu Glu Asp Ala Thr Lys Ile Ile Arg Ala
145                 150                 155                 160

Ile Leu Asp Glu Ser Gly Tyr Pro Lys Pro Leu Lys Leu Ala Asp Lys
                165                 170                 175

Leu Ser Lys Gly Arg Ile Tyr Glu Val Lys Asn Thr Pro Ser Pro Asn
            180                 185                 190

Arg Ser Arg Lys Lys Arg Gly Asn Arg Gly Lys Asp Asn Asn Asn Ser
        195                 200                 205

Gln Gly Asn
    210

<210> SEQ ID NO 40
<211> LENGTH: 194
<212> TYPE: PRT
<213> ORGANISM: Pyrococcus abyssi

<400> SEQUENCE: 40

Met Leu Glu Lys Ile Ala Glu Val Gln Lys Lys Leu Ser Lys Arg Ile
1               5                   10                  15

Val Glu Lys Glu Val Arg Met Val Ser Lys Ile Ala Ala Val Asp Val
                20                  25                  30

Ser Tyr Lys Gly Asn Lys Ala Arg Val Ala Leu Val Ile Cys Ser Phe
            35                  40                  45

Pro Asp Cys Lys Val Leu Lys Thr Lys Val Leu Glu Thr Glu Val Ser
    50                  55                  60

Phe Pro Tyr Ile Pro Thr Phe Phe Leu Arg Glu Thr Arg Pro Ile
65                  70                  75                  80

Leu Leu Val Thr Lys Gly Glu Glu Phe Asp Val Leu Ile Val Glu Gly
                85                  90                  95

His Gly Lys Ala His Pro Arg Lys Tyr Gly Leu Ala Ser His Ile Gly
                100                 105                 110

Leu Ile Leu Gly Lys Pro Thr Ile Gly Val Ala Lys Lys Leu Leu Arg
            115                 120                 125

Gly Thr Pro Glu Asn Ser Tyr Arg Lys Val Gly Lys Ala Tyr Val Ser
        130                 135                 140

Val Gly Asn Met Ile Thr Leu Lys Asp Ala Val Arg Ile Ile Glu Lys
145                 150                 155                 160

Leu Leu Asp Gly Gly Tyr Pro Lys Pro Leu Lys Leu Ala Asp Lys Leu
                165                 170                 175

Ser Lys Gly Lys Ile Ser Glu Asp Glu Asn Thr Leu Pro Ser Asp Lys
            180                 185                 190

Thr Ser

<210> SEQ ID NO 41
<211> LENGTH: 182
<212> TYPE: PRT
<213> ORGANISM: Pyrococcus furiosus

<400> SEQUENCE: 41

Met Ile Asp Leu Arg Lys Leu Thr Glu Val Gln Arg Arg Leu Ser Arg
1               5                   10                  15

Lys Ile Val Glu Lys Pro Ile Asp Ile Ala Lys Val Lys Arg Val Gly
                20                  25                  30

Ala Val Asp Val Ser Tyr Lys Asn Asn Phe Ala Lys Ala Ala Phe Val
            35                  40                  45

Cys Val Glu Phe Pro Ser Gly Glu Ile Ile Lys Thr Lys Thr Ile Val
```

-continued

```
            50                  55                  60
Thr Thr Val Glu Phe Pro Tyr Ile Pro Thr Phe Phe Leu Arg Glu
 65                  70                  75                  80

Thr Lys Pro Ile Leu Leu Ala Val Lys Asp Glu Asn Phe Asp Val Leu
                 85                  90                  95

Leu Val Glu Gly His Gly Lys Ala His Pro Arg Arg Tyr Gly Leu Ala
                100                 105                 110

Ser His Ile Gly Val Ile Leu Ser Lys Pro Thr Ile Gly Val Ala Lys
                115                 120                 125

Arg Leu Leu Arg Gly Val Ser Lys Asp Thr Tyr Val Lys Val Gly Lys
    130                 135                 140

Ala Phe Val Ser Val Gly Asn Leu Ile Thr Leu Asn Asp Ala Val Arg
145                 150                 155                 160

Ile Val Glu Lys Leu Leu Asp Glu Asn Gly Tyr Pro Lys Pro Leu Asn
                165                 170                 175

Ile Ala Asp Lys Leu Ser
                180
```

<210> SEQ ID NO 42
<211> LENGTH: 221
<212> TYPE: PRT
<213> ORGANISM: Archaeoglobus fulgidus

<400> SEQUENCE: 42

```
Met Leu Gln Met Asn Leu Glu Glu Leu Arg Arg Ile Gln Glu Glu Met
  1               5                  10                  15

Ser Arg Ser Val Val Leu Glu Asp Leu Ile Pro Leu Glu Glu Leu Glu
                 20                  25                  30

Tyr Val Val Gly Val Asp Gln Ala Phe Ile Ser Asp Glu Val Val Ser
             35                  40                  45

Cys Ala Val Lys Leu Thr Phe Pro Glu Leu Glu Val Val Asp Lys Ala
     50                  55                  60

Val Arg Val Glu Lys Val Thr Phe Pro Tyr Ile Pro Thr Phe Leu Met
 65                  70                  75                  80

Phe Arg Glu Gly Glu Pro Ala Val Asn Ala Val Lys Gly Leu Val Asp
                 85                  90                  95

Asp Arg Ala Ala Ile Met Val Asp Gly Ser Gly Ile Ala His Pro Arg
                100                 105                 110

Arg Cys Gly Leu Ala Thr Tyr Ile Ala Leu Lys Leu Arg Lys Pro Thr
    115                 120                 125

Val Gly Ile Thr Lys Lys Arg Leu Phe Gly Glu Met Val Glu Val Glu
    130                 135                 140

Asp Gly Leu Trp Arg Leu Leu Asp Gly Ser Glu Thr Ile Gly Tyr Ala
145                 150                 155                 160

Leu Lys Ser Cys Arg Arg Cys Lys Pro Ile Phe Ile Ser Pro Gly Ser
                165                 170                 175

Tyr Ile Ser Pro Asp Ser Ala Leu Glu Leu Thr Arg Lys Cys Leu Lys
                180                 185                 190

Gly Tyr Lys Leu Pro Glu Pro Ile Arg Ile Ala Asp Lys Leu Thr Lys
    195                 200                 205

Glu Val Lys Arg Glu Leu Thr Pro Thr Ser Lys Leu Lys
    210                 215                 220
```

<210> SEQ ID NO 43
<211> LENGTH: 218

```
<212> TYPE: PRT
<213> ORGANISM: Aeropyrum pernix

<400> SEQUENCE: 43

Met Leu Gly Leu Asp Ala Ser Tyr Ser Ala Lys Asp Gly Val Gly Val
 1               5                  10                  15

Gly Ala Ala Val Leu Ile Ser Leu Glu Thr Leu Glu Pro Val Asp Cys
                20                  25                  30

Arg Val Tyr Ile Ser Arg Val Cys Ile Pro Tyr Ile Pro Gly Leu Leu
            35                  40                  45

Ala Phe Arg Glu Leu Ala Val Met Ala Pro Ala Ala Ala Leu Ser
    50                  55                  60

Ala Glu Ala Asp Val Val Met Val Asp Gly His Gly Ile Ala His Pro
65                  70                  75                  80

Arg Arg Phe Gly Ile Ala Ser His Val Gly Val Ile Leu Glu Arg Pro
                85                  90                  95

Ser Ile Gly Val Ala Lys Lys Leu Val Gly Thr Leu Val Glu Gly
                100                 105                 110

Pro Gly Gly Met Tyr Val Val Gln Asp Gly Glu Arg Leu Ala Ile Val
            115                 120                 125

Leu Gly Thr Arg Pro Arg Glu Val Tyr Val Ser Pro Gly His Arg Ile
130                 135                 140

Thr Leu Glu Glu Ala Ala Ser Ile Ala Arg Ala Thr Ile Arg Pro Gly
145                 150                 155                 160

Gly Trp Met Pro Glu Pro Thr Arg Leu Ala Asp Val Ile Ser Lys Ala
                165                 170                 175

Leu Lys Thr Ile Ile Gly Gly Gln Ser Leu Ile Asn Ser Ala Leu Ala
                180                 185                 190

Ser Leu Cys Arg Val Lys Leu Gly Pro Arg Leu Glu Glu Leu Glu Arg
            195                 200                 205

Pro Leu Arg Arg Ala Gly Leu Glu Val Glu
        210                 215

<210> SEQ ID NO 44
<211> LENGTH: 219
<212> TYPE: PRT
<213> ORGANISM: Clostridium acetobutylicum

<400> SEQUENCE: 44

Ala Ser Ser Lys Glu Glu Phe Gln Val Ile Gln Ser Ser Leu Val Lys
 1               5                  10                  15

Arg Ile Lys Leu Ile Ser Asp Phe Lys Glu Glu Asp Ile Lys Leu Cys
                20                  25                  30

Ala Gly Val Asp Leu Ala Tyr Trp Thr Lys Gly Glu Lys Gln Tyr Gly
            35                  40                  45

Val Cys Cys Ile Ile Val Ile Asp Tyr Asn Thr Gly Glu Ile Ile Glu
        50                  55                  60

Lys Ala Tyr Asp Tyr Gly Glu Ile Glu Val Pro Tyr Met Pro Gly Phe
65                  70                  75                  80

Leu Ala Phe Arg Glu Leu Pro Leu Val Ile Lys Thr Val Lys Leu
                85                  90                  95

Lys Asn Glu Pro Asp Ile Phe Met Phe Asp Gly Asn Gly Tyr Leu His
            100                 105                 110

Tyr Asn His Met Gly Ile Ala Thr His Ala Ser Phe Phe Leu Asn Lys
        115                 120                 125
```

```
Pro Thr Ile Gly Val Ala Lys Ser Tyr Leu Lys Val Ala Gly Val Asp
            130                 135                 140
Phe Glu Met Pro Glu Ser Phe Glu Gly Ala Phe Lys Asp Ile Val Ile
145                 150                 155                 160
Asn Glu Glu Val Tyr Gly Arg Val Leu Arg Thr Lys Lys Asp Val Lys
                165                 170                 175
Pro Ile Phe Val Ser Cys Gly Asn Tyr Ile Asp Leu Glu Thr Cys Thr
            180                 185                 190
Lys Ile Cys Ser Lys Leu Ile Asn Asn Asp Ser Arg Leu Pro Ile Thr
            195                 200                 205
Val Arg Leu Ala Asp Leu Glu Thr His Lys Arg
            210                 215

<210> SEQ ID NO 45
<211> LENGTH: 224
<212> TYPE: PRT
<213> ORGANISM: Yersinia pestis

<400> SEQUENCE: 45

Val Phe Asp Thr Lys Ala Leu Gln Ala Glu Gln Arg Gln Arg Ala Ser
  1               5                  10                  15
Glu Ile Ser Leu His Asp Gly Ile Asp Asn Gln Ser Val Arg Phe Ile
                 20                  25                  30
Ala Gly Ala Asp Val Gly Phe Glu Gln His Gly Glu Ile Thr Arg Ala
            35                  40                  45
Ala Ile Ala Ile Leu Arg Tyr Pro Ser Leu Ala Leu Val Glu Tyr Gln
        50                  55                  60
Val Ala Arg Val Ala Thr Ser Leu Pro Tyr Ile Pro Gly Leu Leu Ser
65                  70                  75                  80
Phe Arg Glu Tyr Pro Ala Leu Leu Ala Ala Trp Ala Gln Leu Gln Gln
                85                  90                  95
Arg Pro Asp Leu Ile Leu Val Asp Gly Gln Gly Ile Ala His Pro Arg
            100                 105                 110
Arg Leu Gly Val Ala Ser His Phe Gly Leu Leu Val Asp Val Pro Thr
        115                 120                 125
Ile Gly Val Ala Lys Ser Arg Leu Cys Gly Asp Phe Leu Pro Leu His
130                 135                 140
Gln Asp Val Gly Ala Val Gln Pro Leu Phe Asp Asn Asp Glu Gln Leu
145                 150                 155                 160
Gly Trp Val Trp Arg Ser Lys Ile Arg Cys Asn Pro Leu Phe Ile Ser
                165                 170                 175
Pro Gly His Arg Val Ser Val Gly Ser Ala Leu Ala Trp Val Gln Arg
            180                 185                 190
Cys Met Ala Gly Tyr Arg Leu Pro Glu Pro Thr Arg Trp Ala Asp Ala
        195                 200                 205
Ile Ala Ser Asn Arg Pro Gln Phe Gln Arg Trp Leu Arg Lys Asn Pro
    210                 215                 220

<210> SEQ ID NO 46
<211> LENGTH: 225
<212> TYPE: PRT
<213> ORGANISM: Escherichia coli

<400> SEQUENCE: 46

Met Ile Met Asp Leu Ala Ser Leu Arg Ala Gln Gln Ile Glu Leu Ala
  1               5                  10                  15
```

-continued

```
Ser Ser Val Ile Arg Glu Asp Arg Leu Asp Lys Asp Pro Pro Asp Leu
         20                  25                  30

Ile Ala Gly Ala Asp Val Gly Phe Glu Gln Gly Gly Glu Val Thr Arg
     35                  40                  45

Ala Ala Met Val Leu Leu Lys Tyr Pro Ser Leu Glu Leu Val Glu Tyr
 50                  55                  60

Lys Val Ala Arg Ile Ala Thr Thr Met Pro Tyr Ile Pro Gly Phe Leu
 65                  70                  75                  80

Ser Phe Arg Glu Tyr Pro Ala Leu Leu Ala Ala Trp Glu Met Leu Ser
                 85                  90                  95

Gln Lys Pro Asp Leu Val Phe Val Asp Gly His Gly Ile Ser His Pro
             100                 105                 110

Arg Arg Leu Gly Val Ala Ser His Phe Gly Leu Leu Val Asp Val Pro
         115                 120                 125

Thr Ile Gly Val Ala Lys Lys Arg Leu Cys Gly Lys Phe Glu Pro Leu
130                 135                 140

Ser Ser Glu Pro Gly Ala Leu Ala Pro Leu Met Asp Lys Gly Glu Gln
145                 150                 155                 160

Leu Ala Trp Val Trp Arg Ser Lys Ala Arg Cys Asn Pro Leu Phe Ile
                 165                 170                 175

Ala Thr Gly His Arg Val Ser Val Asp Ser Ala Leu Ala Trp Val Gln
             180                 185                 190

Arg Cys Met Lys Gly Tyr Arg Leu Pro Glu Pro Thr Arg Trp Ala Asp
         195                 200                 205

Ala Val Ala Ser Glu Arg Pro Ala Phe Val Arg Tyr Thr Ala Asn Gln
    210                 215                 220

Pro
225

<210> SEQ ID NO 47
<211> LENGTH: 238
<212> TYPE: PRT
<213> ORGANISM: Bacillus subtilis

<400> SEQUENCE: 47

Met Lys Val Phe Asp Val His Lys Phe Asp Met Lys Lys Glu Gln Asp
  1               5                  10                  15

Phe Leu Gln Val Gln Phe Asn Leu Lys Asn Arg Ile Asn Leu Ser Pro
             20                  25                  30

Thr Ile His Pro Asp Ser Ile Asn Thr Gly Ala Gly Val Asp Leu Ala
         35                  40                  45

Tyr Trp Glu Gln Asp Gly Glu Pro Tyr Gly Val Cys Cys Ile Ile Val
     50                  55                  60

Ile Asp Ala Asp Thr Lys Glu Val Ile Glu Lys Val His Ser Met Gly
 65                  70                  75                  80

Arg Ile Ser Val Pro Tyr Val Ser Gly Phe Leu Ala Phe Arg Glu Leu
                 85                  90                  95

Pro Leu Ile Ile Glu Ala Ala Lys Lys Leu Glu Thr Glu Pro Asp Val
             100                 105                 110

Phe Leu Phe Asp Gly Asn Gly Tyr Leu His Tyr Asn His Met Gly Val
         115                 120                 125

Ala Thr His Ala Ala Phe Phe Leu Gly Lys Pro Thr Ile Gly Ile Ala
    130                 135                 140

Lys Thr Tyr Leu Lys Ile Lys Gly Cys Asp Phe Val Thr Pro Glu Ile
145                 150                 155                 160
```

```
Glu Val Gly Ala Tyr Thr Asp Ile Ile Asp Gly Val Tyr Gly
                165                 170                 175

Arg Ala Leu Arg Thr Arg Asp Val Lys Pro Ile Phe Leu Ser Cys
            180                 185                 190

Gly Asn Tyr Ile Asp Leu Asp Ser Ser Tyr Gln Ile Thr Met Ser Leu
        195                 200                 205

Ile Asn Gln Glu Ser Arg Leu Pro Ile Pro Val Arg Leu Ala Asp Leu
    210                 215                 220

Glu Thr His Val Leu Arg Thr Phe Tyr Gln Lys Asn His Val
225                 230                 235
```

<210> SEQ ID NO 48
<211> LENGTH: 223
<212> TYPE: PRT
<213> ORGANISM: Salmonella typhimurium

<400> SEQUENCE: 48

```
Met Asp Leu Ala Ser Leu Arg Ala Gln Gln Ile Glu Leu Ala Ser Ser
1               5                   10                  15

Val Cys Arg Glu Asp Arg Leu Asp Lys Asp Pro Ala Phe Ile Gly
            20                  25                  30

Gly Ala Asp Val Gly Phe Glu Gln Gly Gly Glu Val Thr Arg Ala Ala
        35                  40                  45

Met Val Leu Leu Lys Tyr Pro Ser Leu Glu Leu Val Glu Tyr Lys Val
    50                  55                  60

Ala Arg Ile Ala Thr Thr Met Pro Tyr Ile Pro Gly Phe Leu Ser Phe
65                  70                  75                  80

Arg Glu Tyr Pro Ala Leu Leu Ala Ala Trp Glu Gln Leu Ser Gln Lys
                85                  90                  95

Pro Asp Leu Leu Phe Val Asp Gly His Gly Ile Ser His Pro Arg Arg
            100                 105                 110

Leu Gly Val Ala Ser His Phe Gly Leu Leu Val Asp Val Pro Thr Ile
        115                 120                 125

Gly Val Ala Lys Lys Arg Leu Cys Gly Lys Phe Glu Pro Leu Ser Ala
    130                 135                 140

Glu Pro Gly Ala Leu Ser Pro Leu Met Asp Lys Gly Glu Gln Leu Ala
145                 150                 155                 160

Trp Val Trp Arg Ser Lys Ala Arg Cys Asn Pro Leu Phe Ile Ala Thr
                165                 170                 175

Gly His Arg Val Ser Thr Asp Ser Ala Leu Ala Trp Val Gln Arg Cys
            180                 185                 190

Met Lys Gly Tyr Arg Leu Pro Glu Pro Thr Arg Trp Ala Asp Ala Val
        195                 200                 205

Ala Ser Gly Arg Pro Ala Phe Val Arg Trp Gln Glu Ile Gln Arg
    210                 215                 220
```

<210> SEQ ID NO 49
<211> LENGTH: 233
<212> TYPE: PRT
<213> ORGANISM: Streptomyces coelicolor

<400> SEQUENCE: 49

```
Met Thr Thr Val Ser Val Gln Ile Pro Ala Gly Trp Pro Ala Thr Glu
1               5                   10                  15

Glu Arg Ala Arg Ala Val Gln Asp Glu Leu Arg Ala Arg Val Val Leu
            20                  25                  30
```

Asp Glu Pro Gly Pro Pro Gly Thr Gly Arg Val Thr Gly Val Asp
             35                  40                  45

Val Ala Tyr Asp Asp Glu Arg Asp Val Val Ala Ala Ala Val Val
 50                  55                  60

Leu Asp Ala Gly Thr Leu Ala Val Val Ala Glu Ala Thr Ala Val Gly
 65                  70                  75                  80

Arg Ile Ser Phe Pro Tyr Val Pro Gly Leu Leu Ala Phe Arg Glu Ile
                 85                  90                  95

Pro Thr Val Leu Ala Ala Leu Glu Ala Leu Pro Cys Pro Pro Gly Leu
                100                 105                 110

Val Val Cys Asp Gly Tyr Gly Leu Ala His Pro Arg Arg Phe Gly Leu
            115                 120                 125

Ala Ser His Leu Gly Val Leu Thr Gly Leu Pro Thr Ile Gly Val Ala
    130                 135                 140

Lys Asn Pro Phe Thr Phe Thr His Asp Asp Pro Asp Thr Pro Arg Gly
145                 150                 155                 160

Ser Thr Ser Pro Leu Leu Ala Gly Ala Glu Glu Val Gly Arg Ala Val
                165                 170                 175

Arg Thr Arg Asp Gly Val Lys Pro Val Phe Val Ser Val Gly His Arg
                180                 185                 190

Val Gly Leu Gly Asn Ala Cys Ala His Thr Leu Ala Leu Thr Pro Ala
            195                 200                 205

Tyr Arg Leu Pro Glu Thr Thr Arg Arg Ala Asp Ala Leu Cys Arg Ala
    210                 215                 220

Ala Leu Arg Asp Ala Ala Tyr Arg Ala
225                 230

<210> SEQ ID NO 50
<211> LENGTH: 203
<212> TYPE: PRT
<213> ORGANISM: Artificial Sequence
<220> FEATURE:
<223> OTHER INFORMATION: Description of Artificial Sequence: Consensus
      sequence

<400> SEQUENCE: 50

Met Leu Asp Leu Leu Ala Arg Ala Val Gln Ile Glu Leu Ala Lys Ser
  1               5                  10                  15

Ile Val Leu Glu Asp Ile Val Asp Glu Val Glu Leu Val Ala Gly Val
                 20                  25                  30

Asp Val Ala Tyr Gly Gly Glu Val Gly Arg Ala Ala Ala Val Val Leu
             35                  40                  45

Asp Tyr Pro Ser Leu Glu Val Val Glu Thr Lys Val Ala Val Gly Arg
 50                  55                  60

Val Ser Phe Pro Tyr Ile Pro Gly Phe Leu Ala Phe Arg Glu Leu Pro
 65                  70                  75                  80

Pro Ile Leu Ala Ala Trp Lys Lys Leu Ser Glu Glu Pro Asp Val Val
                 85                  90                  95

Leu Val Asp Gly His Gly Ile Ala His Pro Arg Arg Leu Gly Leu Ala
                100                 105                 110

Ser His Ile Gly Leu Leu Leu Gly Lys Pro Thr Ile Gly Val Ala Lys
            115                 120                 125

Ser Arg Leu Cys Gly Thr Phe Leu Glu Asp Gly Ala Pro Leu Leu Asp
    130                 135                 140

Gly Gly Glu Gln Leu Gly Tyr Val Leu Arg Thr Lys Arg Cys Lys Pro

```
            145                 150                 155                 160
Ile Phe Val Ser Val Gly His Arg Ile Thr Leu Asp Ser Ala Leu Ala
                165                 170                 175

Ile Val Gln Ala Leu Leu Asp Gly Tyr Arg Leu Pro Glu Pro Thr Arg
            180                 185                 190

Leu Ala Asp Ala Leu Ala Lys Arg Arg Lys Ala
            195                 200
```